US008829248B2

(12) United States Patent
Barnicki et al.

(10) Patent No.: US 8,829,248 B2
(45) Date of Patent: *Sep. 9, 2014

(54) METHOD FOR RECOVERY AND RECYCLE OF RUTHENIUM HOMOGENEOUS CATALYSTS

(75) Inventors: Scott Donald Barnicki, Kingsport, TN (US); Jeffrey Scott Kanel, Kingsport, TN (US); Kenneth Wayne Hampton, Jr., Glimer, TX (US); Eduardo Gallas Cervo, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 469 days.

This patent is subject to a terminal disclaimer.

(21) Appl. No.: 13/208,399

(22) Filed: Aug. 12, 2011

(65) Prior Publication Data

US 2012/0046481 A1  Feb. 23, 2012

Related U.S. Application Data

(63) Continuation-in-part of application No. 12/889,065, filed on Sep. 23, 2010, now Pat. No. 8,466,328.

(60) Provisional application No. 61/374,850, filed on Aug. 18, 2010.

(51) Int. Cl.
| C07C 29/149 | (2006.01) |
| C07C 29/80  | (2006.01) |
| B01J 31/40  | (2006.01) |
| C07C 29/86  | (2006.01) |
| B01J 31/24  | (2006.01) |

(52) U.S. Cl.
CPC ............ *B01J 31/24* (2013.01); *B01J 31/4053* (2013.01); *C07C 29/86* (2013.01); *C07C 29/149* (2013.01); *B01J 2531/821* (2013.01); *B01J 31/2409* (2013.01); *B01J 2531/0238* (2013.01)
USPC .......................................... 568/864; 568/868

(58) Field of Classification Search
USPC ................................................. 568/864, 868
See application file for complete search history.

(56) References Cited

U.S. PATENT DOCUMENTS

| 2,152,852 A | 4/1939 | Loder |
| 2,153,064 A | 4/1939 | Larson |
| 2,211,624 A | 8/1940 | Loder et al. |
| 2,211,625 A | 8/1940 | Loder |
| 2,298,138 A | 10/1942 | Loder |
| 2,436,209 A | 2/1948 | Elgin |
| 2,443,482 A | 6/1948 | Shattuck |
| 3,333,924 A | 8/1967 | Hazen et al. |
| 3,751,453 A | 8/1973 | Kurkov et al. |
| 3,754,028 A | 8/1973 | Lapporte et al. |
| 3,801,627 A | 4/1974 | Kurkov et al. |
| 3,859,349 A | 1/1975 | Cody |
| 3,911,003 A | 10/1975 | Suzuki |
| 3,927,078 A | 12/1975 | Lapporte et al. |
| 3,948,977 A | 4/1976 | Suzuki |
| 3,948,986 A | 4/1976 | Suzuki |
| 4,016,208 A | 4/1977 | Suzuki |
| 4,052,452 A | 10/1977 | Scardigno et al. |
| 4,087,470 A | 5/1978 | Suzuki |
| 4,112,245 A | 9/1978 | Zehner et al. |
| 4,128,575 A | 12/1978 | Leupold et al. |
| 4,136,112 A | 1/1979 | Bakshi |
| 4,140,866 A | 2/1979 | Nielsen |
| 4,153,809 A | 5/1979 | Suzuki |
| 4,228,305 A | 10/1980 | Suzuki |
| 4,275,234 A | 6/1981 | Baniel et al. |
| 4,291,007 A | 9/1981 | Baniel |
| 4,308,397 A | 12/1981 | Suzuki |
| 4,366,333 A | 12/1982 | Wilkes |
| 4,409,395 A | 10/1983 | Miyazaki et al. |
| 4,431,486 A | 2/1984 | Balmat |
| 4,440,734 A | 4/1984 | Kougioumoutzakis |
| 4,501,917 A | 2/1985 | Schmidt et al. |
| 4,691,048 A | 9/1987 | Hughes et al. |
| 4,824,997 A | 4/1989 | Macfarlane et al. |
| 4,935,102 A | 6/1990 | Berg |
| 4,966,658 A | 10/1990 | Berg |
| 4,990,629 A | 2/1991 | Souma |
| 5,026,927 A | 6/1991 | Andrews et al. |

(Continued)

FOREIGN PATENT DOCUMENTS

| DE | 3133353 C2 | 3/1983 |
| EP | 0 114 657 B1 | 3/1987 |

(Continued)

OTHER PUBLICATIONS

Baniel, A., et al., "Acid-Base Couple Solvents in Recovery of Mineral Acids From Waste Streams", Proceedings of $2^{nd}$ International Conference on Separations Science and Technology, Oct. 1-4, 1989, pp. 667-674.

Hou-Yong, Sun, et al. "Reactive extraction of glycolic acid in high content solution with tri-n-octylamine" Journal of Chemical Engineering of Chinese Universities, Feb. 2007, vol. 21 pp. 26-30.

Co-pending U.S. Appl. No. 12/889,065, filed Sep. 23, 2010 Scott Donald Barnicki, et al.

(Continued)

*Primary Examiner* — Elvis O Price
(74) *Attorney, Agent, or Firm* — Jennifer R. Knight

(57) ABSTRACT

Disclosed is a process for the extractive recovery of a homogeneous ruthenium catalyst from the reaction product of the hydrogenation of glycolic acid, glycolate esters, and/or glycolic acid oligomers with an extractant comprising a hydrophobic solvent and an optional hydrophilic solvent. The ruthenium catalyst, which can include 1,1,1-tris(diaryl- or dialkylphosphinomethyl)alkane ligands, can be recovered from the hydrophobic extract phase by back extraction with a hydrophilic solvent and recycled to a process for the preparation of ethylene glycol by the hydrogenation of glycolic acid and glycolic acid derivatives.

38 Claims, 7 Drawing Sheets

(56) References Cited

U.S. PATENT DOCUMENTS

| | | | |
|---|---|---|---|
| 5,210,335 | A | 5/1993 | Schuster et al. |
| 5,214,219 | A | 5/1993 | Casale et al. |
| 5,276,181 | A | 1/1994 | Casale et al. |
| 5,423,955 | A | 6/1995 | Berg |
| 5,455,372 | A | 10/1995 | Hirai et al. |
| 5,723,662 | A | 3/1998 | Ebmeyer et al. |
| 5,932,772 | A | 8/1999 | Argyropoulos et al. |
| 5,952,530 | A | 9/1999 | Argyropoulos et al. |
| 6,252,121 | B1 | 6/2001 | Argyropoulos et al. |
| 6,291,725 | B1 | 9/2001 | Chopade et al. |
| 6,294,700 | B1 | 9/2001 | Kanel et al. |
| 6,303,829 | B1 | 10/2001 | Kanel et al. |
| 6,307,108 | B1 | 10/2001 | Argyropoulos et al. |
| 6,307,109 | B1 | 10/2001 | Kanel et al. |
| 6,307,110 | B1 | 10/2001 | Argyropoulos et al. |
| 6,310,260 | B1 | 10/2001 | Argyropoulos et al. |
| 6,376,723 | B2 | 4/2002 | Drent et al. |
| 7,122,698 | B2 | 10/2006 | Yoshida et al. |
| 7,164,040 | B2 | 1/2007 | Kuroda et al. |
| 7,223,885 | B2 | 5/2007 | Van Krieken |
| 7,439,391 | B2 | 10/2008 | Gallagher et al. |
| 7,615,671 | B2 | 11/2009 | Puckette et al. |
| 7,709,689 | B2 | 5/2010 | Kilner et al. |
| 7,772,423 | B2 | 8/2010 | Celik et al. |
| 8,466,328 | B2 | 6/2013 | Barnicki et al. |
| 2004/0222153 | A1 | 11/2004 | Baniel et al. |
| 2006/0160197 | A1 | 7/2006 | Li et al. |
| 2007/0123739 | A1 | 5/2007 | Crabtree et al. |
| 2008/0275277 | A1 | 11/2008 | Kalagias |
| 2009/0143612 | A1 | 6/2009 | Puckette et al. |
| 2011/0144388 | A1 | 6/2011 | Sun et al. |
| 2011/0166383 | A1 | 7/2011 | Sun et al. |
| 2012/0046481 | A1 | 2/2012 | Barnicki et al. |
| 2012/0046500 | A1 | 2/2012 | Barnicki et al. |
| 2012/0078010 | A1 | 3/2012 | Barnicki et al. |

FOREIGN PATENT DOCUMENTS

| | | |
|---|---|---|
| EP | 0 676 239 A2 | 10/1995 |
| EP | 1 679 331 A1 | 7/2006 |
| GB | 508383 A | 6/1939 |
| GB | 1499245 A | 1/1978 |
| GB | 2179337 A | 7/1986 |
| IL | 89044 A | 3/1993 |
| JP | 56100741 A | 8/1981 |
| JP | 56131546 A | 10/1981 |
| JP | 56133237 A | 10/1981 |
| JP | 5746934 A | 3/1982 |
| JP | 57040442 A | 3/1982 |
| JP | 57102837 A | 6/1982 |
| JP | 6228045 A | 8/1994 |
| JP | 1999147042 A | 6/1999 |
| JP | 2004131411 A | 4/2004 |
| RU | 1436453 A1 | 9/1996 |
| WO | WO 97/15543 A1 | 5/1997 |
| WO | WO 2006/069127 A1 | 6/2006 |
| WO | WO 2009/140850 A1 | 11/2009 |
| WO | WO 2012/040007 A2 | 3/2012 |
| WO | WO 2012/130316 A1 | 10/2012 |

OTHER PUBLICATIONS

USPTO Office Action for U.S. Appl. No. 13/431,358 dated Nov. 12, 2013.
Notification of Transmittal of the International Search Report and the Written Opinion of the International Search Authority with Mail Date of Aug. 13, 2013 for International Application No. PCT/US2013/033458.
Notification of Transmittal of the International Search Report and the Written Opinion of the International Search Authority with Mail Date of Jun. 25, 2013 for International Application No. PCT/US2013/033501.
Notification of Transmittal of the International Search Report and the Written Opinion of the International Search Authority with Mail Date of Aug. 16, 2013 for International Application No. PCT/US2013/033410.
Notification of Transmittal of the International Search Report and the Written Opinion of the International Search Authority with Mail Date of Jun. 21, 2013 for International Application No. PCT/US2013/033520.
Notification of Transmittal of the International Search Report and the Written Opinion of the International Search Authority with Mail Date of Jun. 21, 2013 for International Application No. PCT/US2013/033411.
Notification of Transmittal of the International Search Report and the Written Opinion of the International Search Authority with Mail Date of Jul. 8, 2013 for International Application No. PCT/US2013/033494.
Notification of Transmittal of the International Search Report and the Written Opinion of the International Search Authority with Mail Date of Jul. 12, 2013 for International Application No. PCT/US2013/033446.
Co-pending U.S. Appl. No. 13/896,706, filed May 17, 2013, Scott Donald Barnicki, et al.
USPTO Notice of Allowance for U.S. Appl. No. 12/889,065 dated Oct. 15, 2012.
Malinowski, J. J. "Evaluation of Liquid Extraction Potentials for Downstream Separation of 1,3-Propanediol", Biotechnology Techniques, vol. 18, No. 2 (Jan. 1, 1999), pp. 127-130.
Cox et al. "Mechanistic Studies in Strong Acids . . . ", Journal of Organic Chemistry, vol. 51, No. 19 (Sep. 1, 1986), pp. 3619-3624.
Li et al. "Aqueous Two-phase Extraction of 1,3-propanediol from Glycerol-based Fermentation Broths", Separation and Purification Technology Separation and Purification Technology, vol. 66, No. 3 (May 7, 2009), pp. 472-478.
USPTO Office Action dated Jul. 18, 2013 for U.S. Appl. No. 13/431,386.
USPTO Notice of Allowance for U.S. Appl. No. 13/431,358 dated Aug. 2, 2013.
USPTO Notice of Allowance for U.S. Appl. No. 12/889,045 dated Sep. 19, 2013.
USPTO Notice of Allowance for U.S. Appl. No. 13/896,706 dated Oct. 4, 2013.
Notification of Transmittal of the International Search Report and the Written Opinion of the International Search Authority with Mail Date of Mar. 15, 2012 for International Application No. PCT/US2011/051490.
Notification of Transmittal of the International Search Report and the Written Opinion of the International Search Authority with Mail Date of Nov. 28, 2011 for International Application No. PCT/US2011/047842.
Celik et al., "Synthesis of precursors to ethylene glycol from formaldehyde and methyl formate catalyzed by heteropoly acids", Journal of Molecular Catalysis A: Chemical 288, (2008), pp. 87-96.
Celik et al., "Vapor-phase carbonylation of dimethoxymethane of H-Faujasite", Angewandte. Chemie Int. Ed. 2009, 48, pp. 4813-4815.
Hou-Yong, Sun, et al. "Reactive extraction of glycolic acid in high content solution with tri-n-octylamine" Journal of Chemical Engineering of Chinese Universities vol. 21 pp. 26-30.
Bizek, Vladislav et al. "Amine Extraction of Hydroxycarboxylic Acids. 1. Extraction of Citric Acid with 1-Octanol/n-Heptane Solutions of Trialkylamine" Ind. Eng. Chem. Res. 1992, 31, 1554-1562.
Tamada, Janet A. et al. "Extraction of Carboxylic Acids with Amine Extractants. 1. Equilibria and Law of Mass Action Modeling" Ind. Eng. Chem. Res. 1990, 29, 1319-1326.
Smith, E. Lester "The Acid-Binding Properties of Long-Chain Aliphatic Amines" J.S.C.I., 67, Feb. 1948 pp. 48-51.
Walker, "Formaldehyde", Walker, ACS Monograph, Washington, DC., ACS, 1964, p. 95.
Eyal, A., et al. "Recovery and Concentration of Strong Mineral Acids from Dilute Solutions Through LLX III. A "Temperature Swing" Based Process" Solvent Extraction and Ion Exchange, 9 (2), 223-236 (1991).
Eyal, A.M., et al. "Recovery and Concentration of Strong Mineral Acids from Dilute Soltions Through LLX. I: Review of Parameters

(56) References Cited

OTHER PUBLICATIONS for Adjusting Extractant Properties and Analysis of Process Options" Solvent Extraction and Ion Exchange, 9 (2), 195-210 (1991).

Eyal, A.M., et al. "Recovery and Concentration of Strong Mineral Acids from Dilute Solutions Through LLX. II. Reversible Extraction with Branched-Chain Amines" Solvent Extraction and Ion Exchange, 9(2), 211-222 (1991).

Eyal, Aharon, et al. "Extraction of Strong Mineral Acids by Organic Acid-Base Couples", Ind. Eng. Chem. Process Des. Dev., (1982), vol. 21, No. 2, pp. 334-337.

"Handbook of Solvent Extraction" Krieger Publishing Company, Malabar, FL, 1991, pp. 275-501.

Treybal, Robert E. "Methods of Calculation II. Stagewise Contact, Multicomponent Systems", Liquid Extraction, $2^{nd}$ Edition, McGraw-Hill Book Company, New York. 1963, pp. 275-276.

Treybal, "Liquid Extraction," $2^{nd}$ Ed., McGraw-Hill Book Company, New York, NY, 1963, pp. 349-366.

Gerberich, H. Robert, et al., "Formaldehyde", Kirk-Othmer Encyclopedia of Chemical Technology, vol. 11, $4^{th}$ Edition, 1994, pp. 929-950.

Treybal, Robert E., Liquid Extraction, $2^{nd}$ Ed., McGraw Hill Book Company, 1963, pp. 248-252.

Lynch, Kathleen M., et al., "Improved Preparations of 3-Chloro-2(chloromethyl)-1-propene and 1,1-Dibromo-2,2-bis(chloromethyl)-cyclopropane: Intermediates in the Synthesis of [1.1.1]Propellane", J. Org. Chem, 60, (1995), pp. 4666-4668.

"Tray Design and Operation", Distillation Design, McGraw-Hill, New York (1992), Chapter 6, pp. 259-363.

"Packing Design and Operation", Distillation Design, McGraw-Hill, New York, (1992), Chapter 8, pp. 421-521.

Seader, J.D., Ph.D, et al., "Distillation", Perry's Handbook of Chemical Engineering, Section 13, $7^{th}$ Ed., McGraw-Hill Book Co. 1999.

Lee, Sang Young, et al., "Carbonylation of Formaldehyde over Ion Exchange Resin Catalysts. 1. Batch Reactor Studies", Ind. Eng. Chem. Res., 32, (1993), pp. 253-259.

Xu, Qiang, et al., "Preparation and Catalytic Application of Cationic Metal Carbonyls", Science and Technology in Catalysis, (2002), pp. 215-218.

Xu, Qiang, "Metal carbonyl cations: generation, characterization and catalytic application", Coordination Chemistry Reviews, 231, (2002), pp. 83-108.

Suzuki, S., et al., "Ethylene Glycol from Methanol and Synthesis Gas via Glycolic Acid", Catalytic Conversions of Synthesis Gas and Alcohols to Chemicals, (1984). pp. 221-247.

Wang, Zheng Bao, et al., Carbonylation of Formaldehyde with Carbon Monoxide over Cation-Exchange Resin Catalysts, Bull. Chem. Soc. Jpn., 72, (1999), pp. 1935-1940.

Sano, Tsunejo, et al., "Synthesis of 1,3-dioxolan-4-one from trioxane and carbon monoxide on HZSM-5 zeolite", Chem. Community, (1997), pp. 1827-1828.

Souma, Yoshie, "Carbonylation at Ambient Pressure in Strong Acids", Journal of Synthetic Organic Chemistry, vol. 41, No. 6, (1983), pp. 561-569.

Soma, Yoshie, et al., "Normal-Pressure CO Addition Reaction of Formaldehyde and Related Compounds on Copper Carbonyl Catalyst", Catalyst 23, (1981), pp. 48-50.

Li, Tao, et al., "Carbonylation of formaldehyde catalyzed by p-toluenesulfonic acid", Catalysis Today, 111, (2006), pp. 288-291.

Souma, Yoshie, et al., "Synthesis of tert.-Alkanoic acid catalyzed by $Cu(CO)^+_n$ and $Ag(CO)^+_2$ under atmospheric pressure", Catalysis Today, 36, (1997), pp. 91-97.

Hendriksen, Dan E., "Intermediates to Ethylene Glycol: Carbonylation of Formaldehyde Catalyzed by NAFION Solid Perfluorosulfonic Acid Resin", Prep. A.C.S. Div. Fuel Chem., 28, (1983), pp. 176-190.

Bhattacharyya, S.K., et al., "High-Pressure Synthesis of Glycolic Acid from Formaldehyde, Carbon Monoxide, and Water in Presence of Nickel, Cobalt, and Iron Catalysts", Advanced Catalysts, 9, (1957), pp. 625-635.

Baniel, A., et al., "Acid-Base Couple Solvents in Recovery of Mineral Acids From Waste Streams", Proceedings of $2^{nd}$ International Conference on Separations Science and Technology, pp. 667-674.

Wegescheider, Rud., et al., "Addition of Acid Anhydrides to Aldehydes and Ketones", Royal and Imperial University of Vienna, presented at the meeting of Nov. 4, 1909, pp. 1-47.

King, Walter D., et al. "The Acid-Catalyzed Reaction of Acetic Anhydride with Some Oxocanes", Journal of Applied Polymer Science, vol. 18, (1974) pp. 547-554.

He, Dehua, et al., "Condensation of formaldehyde and methyl formate to methyl glycolate and methyl methoxy acetate using heteropolyacids and their salts", Catalysis Today, 51, (1999), pp. 127-134.

Co-pending U.S. Appl. No. 12/889,045, filed Sep. 23, 2010, Scott Donald Barnicki, et al.

Co-pending U.S. Appl. No. 12/899,065, filed Sep. 23, 2010, Scott Donald Barnicki, et al.

Co-pending U.S. Appl. No. 13/431,335, filed Mar. 27, 2012, Scott Donald Barnicki, et al.

Co-pending U.S. Appl. No. 13,431,308, filed Mar. 27, 2012, Scott Donald Barnicki, et al.

Co-pending U.S. Appl. No. 13/431,358, filed Mar. 27, 2012, Scott Donald Barnicki, et al.

Co-pending U.S. Appl. No. 13/431,369, filed Mar. 27, 2012, Scott Donald Barnicki, et al.

Co-pending U.S. Appl. No. 13/431,402, filed Mar. 27, 2012, Scott Donald Barnicki, et al.

Co-pending U.S. Appl. No. 13/431,386, filed Mar. 27, 2012, Scott Donald Barnicki, et al.

Co-pending U.S. Appl. No. 13/491,954, filed Jun. 8, 2012 Mesfin Ejerssa Janka.

USPTO Notice of Allowance for U.S. Appl. No. 12/889,045 dated Jul. 18, 2012.

Asci, Yavuz Selim et al. "Extraction of Glycolic Acid from Aqueous Solutions by Amberlite LA-2 in Difference Diluent Solvents" J. Chem Eng. Data 2009, 54, 2791-2794.

Bonrath, et al.; "Sustainability, Methantrisulfonic Acid: A Highly Efficient Strongly Acidic Catalyst for Wagner-Meerwein Rearrangement, Friedel-Crafts Alkylation and Acylation Reactions"; Examples from Vitamin E Synthesis, 2009, 1, pp. 161-168.

USPTO Notice of Allowance for U.S. Appl. No. 13/896,706 dated Nov. 19, 2013.

USPTO Notice of Allowance for U.S. Appl. No. 13/431,386 dated Dec. 3, 2013.

USPTO Notice of Allowance for U.S. Appl. No. 12/889,045 dated Dec. 13, 2013.

USPTO Office Action for U.S. Appl. No. 13/431,369 dated Jan. 13, 2014.

USPTO Office Action for U.S. Appl. No. 13/431,402 dated Jan. 31, 2014.

USPTO Notice of Allowance for U.S. Appl. No. 13/896,706 dated Mar. 10, 2014.

USPTO Notice of Allowance for U.S. Appl. No. 13/431,335 dated Mar. 12, 2014.

METHOD FOR RECOVERY AND RECYCLE OF RUTHENIUM HOMOGENEOUS CATALYSTS

CROSS REFERENCES TO RELATED APPLICATIONS

This application is a Continuation-in-Part and claims the benefit of U.S. Non-Provisional application Ser. No. 12/889,065, filed Sep. 23, 2010-, (now U.S. Pat. No. 8,466,328) which claims the benefit of Provisional Application Ser. No. 61/374,850, filed Aug. 18, 2010, both of which are incorporated herein by reference in their entirety.

FIELD OF THE INVENTION

The invention generally relates to a process for separation of homogeneous catalysts from the reaction products of the hydrogenation of 1,2-dioxygenated organic compounds. More specifically, this invention relates to a process for the extractive recovery of a catalyst composition comprising ruthenium and a 1,1,1-tris(diaryl- or dialkylphosphinomethyl)alkane from a glycolic acid hydrogenation product. The recovered catalyst system may be recycled to a process for the hydrogenation of glycolic acid and/or derivatives thereof.

BACKGROUND OF THE INVENTION

Homogeneous ruthenium—phosphine catalysts are useful for the reduction of 1,2-dioxygenated organic compounds, such as alkyl oxalates, glycolic acid, and glycolate esters to ethylene glycol. In particular, catalysts containing ruthenium in combination with tridentate phosphorus ligands such as, for example, 1,1,1-tris(diphenylphosphinomethyl)ethane (also known as "triphos"), have been used for the reduction of glycolic acid to ethylene glycol. These catalyst systems, however, are expensive and their economical use requires efficient recovery of the metal and ligand from the reaction products.

Optimizing recovery of the catalyst system is a complex problem involving several factors such as, for example, thermal degradation of the catalyst, the efficiency of the catalyst recovery process, and the impact of reaction by-product build-up in the reactor on both the reaction and downstream by-product separation steps.

The entire reactor effluent can be processed to recover the catalyst system from the reaction products and by-products. Alternatively, the reactor effluent can be processed to remove at least a part of the reaction products, and all or part of the concentrated reactor effluent can be processed to recover the catalyst system. The smallest catalyst recovery stream occurs when the reactor effluent is concentrated and most of the concentrated reactor effluent returns to the reactor with a minor amount of the concentrated reactor effluent, a purge stream, being processed to remove the reaction-by products and recycle the catalyst system to the reactor.

Extraction is an attractive means to recover the catalyst system from the reactor effluent in that extraction can readily be accomplished at low temperatures, minimizing the thermal degradation of the catalyst components. Feeding the reactor effluent directly to the extractor allows for minimum thermal degradation, but requires any water added to the extractor to be separated from the ethylene glycol product. This can economically limit the amount of water that can be added to the extractor and reduce catalyst system recovery efficiency. Concentrating the reactor effluent before feeding it to the extractor allows for significant flexibility in the amount of water added to the extractor, but may increase the thermal degradation of the catalyst components. Furthermore, a concentration step typically will not remove polyols which when recycled to the reactor can form unwanted diols such as 1,2-propanediol and 1,2-butanediol.

A method for the efficient recovery of ruthenium-1,1,1-tris (diaryl- or dialkylphosphinomethyl)alkane catalyst compositions from glycolic acid hydrogenation effluent to maximize recovery of the catalyst system at the lowest cost to the overall process, considering both reaction and separation steps, for producing ethylene glycol is desired.

SUMMARY OF INVENTION

We have discovered that catalyst compositions comprising ruthenium and tridentate phosphorus ligands can be efficiently recovered from glycolic acid hydrogenation reaction products by an extraction process. One aspect of our invention, therefore, is a process for recovering a homogeneous catalyst, comprising (A) extracting a feed comprising
  (i) a glycolic acid hydrogenation effluent, comprising
    (a) about 10 to about 99 weight percent ethylene glycol, about 0.5 to about 50 weight percent water, and about 0.5 to about 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
    (b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes: and
  (ii) additional water whereby the feed comprises about 5 to about 50 weight percent water based on the total weight of the glycolic acid hydrogenation effluent and the additional water;
with a first extractant, comprising
  (i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
  (ii) optionally, a hydrophilic solvent;
to form a first raffinate phase comprising a major amount of the ethylene glycol and a minor amount of the catalyst composition contained in the glycolic acid hydrogenation effluent and a first extract phase comprising a major amount of the catalyst composition and a minor amount of the ethylene glycol contained in the glycolic acid hydrogenation effluent;
(B) separating the first raffinate phase and the first extract phase; and
(C) recovering the catalyst composition from the first extract phase of step (B) by:
  (i) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); or (ii) distilling the first extract phase of step (B) to form a distillate comprising a major amount of the hydrophobic solvent contained in the first extract phase of step (B) and a bottoms comprising a major amount of the catalyst composition contained in the first extract phase of step (B).

One aspect of our invention is a process for recovering a homogeneous catalyst, comprising
(A) extracting a feed comprising
   (i) a glycolic acid hydrogenation effluent, comprising
      (a) about 40 to about 99 weight percent ethylene glycol, about 0.5 to about 40 weight percent water, and about 0.5 to 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
      (b) a catalyst composition comprising ruthenium and 1,1,1-tris(diphenylphosphinomethyl)ethane: and
   (ii) additional water whereby the feed comprises about 5 to about 40 weight percent water based on the total weight of the glycolic acid hydrogenation effluent and the additional water;
   with a first extractant, comprising about 60 to 100 weight percent 2-ethylhexanol, pentanol, isobutyl isobutyrate, undecanone, methylisobutyl ketone, diisopropyl ether, or mixtures thereof and 0 to about 40 weight percent of a hydrocarbon having from 5 to 20 carbon atoms, each based on the total weight of the first extractant, to form a first raffinate phase comprising a major amount of the ethylene glycol and a minor amount of the catalyst composition contained in the glycolic acid hydrogenation effluent and a first extract phase comprising a major amount of the catalyst composition and a minor amount of the ethylene glycol contained in the glycolic acid hydrogenation effluent;
(B) separating the first raffinate phase and the first extract phase; and
(C) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); and
(D) combining the second raffinate phase of step (C) with the first extractant of step (A), or distilling the second raffinate phase of step (C) to produce a hydrophobic solvent distillate and combining the hydrophobic solvent distillate with the first extractant of step (A).

One aspect of our invention is a process for recovering a homogeneous catalyst, comprising
(A) contacting an aqueous mixture comprising glycolic acid, glycolate esters, methyl glycolate, oligomers of glycolic acid, or mixtures thereof, with hydrogen in the presence of a catalyst composition comprising ruthenium and 1,1,1-tris(diphenylphosphinomethyl)ethane to form a glycolic acid hydrogenation effluent comprising about 80 to about 95 weight percent ethylene glycol, about 0.5 to about 15 weight percent water, and about 0.5 to about 15 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent, and the catalyst composition;
(B) extracting a feed comprising the glycolic acid hydrogenation effluent and additional water whereby the feed comprises about 10 to about 30 weight percent water, based on the total of the glycolic acid hydrogenation effluent and the additional water, with a first extractant comprising about 60 to 100 weight percent 2-ethylhexanol and 0 to about 40 weight percent of a hydrocarbon having 5 to 20 carbon atoms, each based on the total weight of the first extractant, to form a first raffinate phase comprising a major amount of the ethylene glycol contained in the glycolic acid hydrogenation effluent and a first extract phase comprising a major amount of the catalyst composition contained in the glycolic acid hydrogenation effluent;
(C) separating the first raffinate phase and the first extract phase;
(D) extracting the first extract phase of step (C) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (C) and a second raffinate phase comprising a minor amount of the catalyst composition contained in the first extract phase of step (C); and
(E) combining the second extract phase of step (D) with the aqueous mixture of step (A).

One aspect of our invention is a process for recovering a homogeneous catalyst, comprising
(A) extracting a feed comprising
   (i) a glycolic acid hydrogenation effluent, comprising
      (a) about 0.5 to about 50 weight percent ethylene glycol, about 0.5 to about 50 weight percent water, and about 25 to 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
      (b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes: and
   (ii) additional water whereby the feed comprises about 5 to about 95 weight percent water based on the total weight of the glycolic acid hydrogenation effluent and the additional water;
   with a first extractant, comprising
      (i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
      (ii) optionally, a hydrophilic solvent;
   to form a first raffinate phase comprising a major amount of the one or more reaction by-products and a minor amount of the catalyst composition contained in the glycolic acid hydrogenation effluent and a first extract phase comprising a major amount of the catalyst composition and a minor amount of the one or more reaction by-products contained in the glycolic acid hydrogenation effluent;
(B) separating the first raffinate phase and the first extract phase; and (C) recovering the catalyst composition from the first extract phase of step (B) by:
  (i) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); or
  (ii) distilling the first extract phase of step (B) to form a distillate comprising a major amount of the hydrophobic solvent contained in the first extract phase of step (B) and a bottoms comprising a major amount of the catalyst composition contained in the first extract phase of step (B).

One aspect of our invention is a process for recovering a homogeneous catalyst, comprising
(A) extracting a feed comprising
  (i) a glycolic acid hydrogenation effluent, comprising
    (a) about 0.5 to about 30 weight percent ethylene glycol, about 0.5 to about 30 weight percent water, and about 40 to 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
    (b) a catalyst composition comprising ruthenium and 1,1,1-tris(diphenylphosphinomethyl)ethane: and
  (ii) additional water whereby the feed comprises about 10 to about 90 weight percent water based on the total weight of the glycolic acid hydrogenation effluent and the additional water;
  with a first extractant, comprising about 60 to 100 weight percent 2-ethylhexanol, butanol, pentanol, isobutyl isobutyrate, undecanone, methylisobutyl ketone, diisopropyl ether, or mixtures thereof, and 0 to about 40 weight percent of a hydrocarbon having 5 to 20 carbon atoms, each based on the total weight of the first extractant, to form a first raffinate phase comprising a major amount of the one or more reaction by-products and a minor amount of the catalyst composition contained in the glycolic acid hydrogenation effluent and a first extract phase comprising a major amount of the catalyst composition and a minor amount of the one or more reaction by-products contained in the glycolic acid hydrogenation effluent;
(B) separating the first raffinate phase and the first extract phase; and
(C) distilling the first extract phase of step (B) to form a distillate comprising a major amount of the hydrophobic solvent contained in the first extract phase of step (B) and a bottoms comprising a major amount of the catalyst composition contained in the first extract phase of step (B); and
(D) combining the distillate of step (C) with the first extractant of step (A).

One aspect of our invention is a process for recovering a homogeneous catalyst, comprising
(A) contacting an aqueous mixture comprising glycolic acid, glycolate esters, methyl glycolate, oligomers of glycolic acid, or mixtures thereof, with hydrogen in the presence of a catalyst composition comprising ruthenium and 1,1,1-tris(diphenylphosphinomethyl)ethane to form a glycolic acid hydrogenation product, concentrating the glycolic acid hydrogenation product to form a glycolic acid hydrogenation effluent comprising about 0.5 to about 20 weight percent ethylene glycol, about 0.5 to about 20 weight percent water, and about 70 to about 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent, and the catalyst composition;
(B) extracting a feed comprising the glycolic acid hydrogenation effluent and additional water whereby the feed comprises about 10 to about 85 weight percent water, based on the total weight of the glycolic acid hydrogenation effluent and the additional water, with a first extractant, comprising about 60 to 100 weight percent pentanol and about 0 to about 40 weight percent of a hydrocarbon having 5 to 20 carbon atoms, each based on the total weight of the first extractant, to form a first raffinate phase comprising a major amount of the one or more reaction by-products contained in the glycolic acid hydrogenation effluent and a first extract phase comprising a major amount of the catalyst composition contained in the glycolic acid hydrogenation effluent;
(C) separating the first raffinate and extract phases;
(D) distilling the first extract phase of step (C) to form a distillate comprising a major amount of the hydrophobic solvent contained in the first extract phase of step (C) and a bottoms comprising a major amount of the catalyst composition contained in the first extract phase of step (C); and
(E) combining the bottoms of step (C) with the aqueous mixture of step (A).

DETAILED DESCRIPTION

Figure 1:
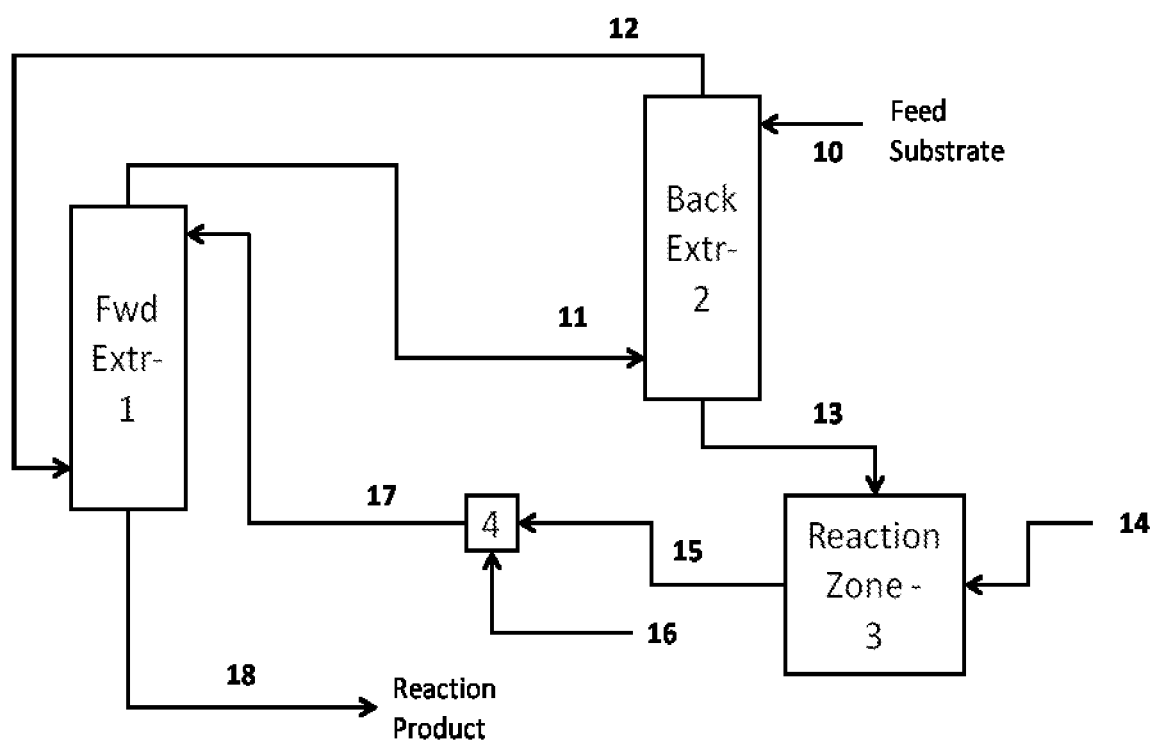
FIG. 1 is a schematic flow diagram for one embodiment of the invention in which a hydrogenated glycolic acid stream is subjected to a forward extraction with a hydrophobic solvent to produce a catalyst-rich extract that is back extracted with a hydrophilic solvent and returned to the hydrogenation reaction zone.

The present invention provides a method to recover and recycle homogeneous catalyst compositions comprising ruthenium and tridentate phosphorus ligands from glycolic acid hydrogenation products. In a general embodiment, therefore, our invention provides a process for recovering a homogeneous catalyst, comprising (A) extracting a feed comprising
  (i) a glycolic acid hydrogenation effluent, comprising
    (a) about 10 to about 99 weight percent ethylene glycol, about 0.5 to about 50 weight percent water, and about 0.5 to 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
    (b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes; and
  (ii) additional water whereby the feed comprises about 5 to about 50 weight percent water based on the total weight of the glycolic acid hydrogenation effluent and the additional water;
  with a first extractant, comprising
  (i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
  (ii) optionally, a hydrophilic solvent;
  to form a first raffinate phase comprising a major amount of the ethylene glycol and a minor amount of the catalyst composition contained in the glycolic acid hydrogenation effluent and a first extract phase comprising a major amount of the catalyst composition and a minor amount of the ethylene glycol contained in the glycolic acid hydrogenation effluent;
(B) separating the first raffinate phase and the first extract phase; and
(C) recovering the catalyst composition from the first extract phase of step (B) by:
  (i) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); or
  (ii) distilling the first extract phase of step (B) to form a distillate comprising a major amount of the hydrophobic solvent contained in the first extract phase of step (B) and a bottoms comprising a major amount of the catalyst composition contained in the first extract phase of step (B).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons," is intended to specifically include and disclose $C_1$ and $C_5$ hydrocarbons as well as $C_2$, $C_3$, and $C_4$ hydrocarbons.

Also, it is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the term "feed" is intended to have its commonly understood meaning in the liquid-liquid extraction art, that is the solution that contains the materials to be extracted or separated. In the present invention, one example of a feed is a reaction product or effluent from the hydrogenation of aqueous glycolic acid that typically comprises one or more of ethylene glycol, unreacted glycolic acid, mono- and diesters of glycolic acid with ethylene glycol, glycolic acid oligomers, esters of glycolic acid oligomers, other reaction by-products, and a homogeneous catalyst composition comprising ruthenium and a tridentate phosphine ligand comprising a 1,1,1-tris(diarylphosphinomethyl)alkane or 1,1,1-tris(dialkylphosphinomethyl)alkane. Another example of a feed is a catalyst-rich hydrophobic extract from the extraction of the glycolic acid hydrogenation reaction effluent that subsequently can be extracted with a hydrophilic solvent to recover the catalyst composition in a form suitable for recycle into the hydrogenation reaction without further purification. The feed, or glycolic acid hydrogenation effluent, also may contain various tridentate phosphine ligand degradation products formed in the reaction, and one or more solvents. The term "extraction solvent," as used herein, is intended to be synonymous with the term "extractant" or "solvent" and is intended to mean the immiscible liquid that is used in the extraction process to extract materials or solutes from the feed. In the present invention, one example of an extraction solvent is an alkanol, an alkyl containing 4 to 20 carbon atoms and at least one OH moiety, such as, 2-ethylhexanol or pentanol. The term "extract" is the immiscible liquid left from the extraction solvent after it has been contacted with the feed. The term "raffinate" is intended to mean the liquid phase left from the feed after it has been contacted with the extraction solvent. The term "wash solvent" is understood to mean a liquid used to wash or enhance the purity of the raffinate or extract phase. Similarly, separation can take place via distillation, a thermal method for separating liquids by evaporation and subsequent condensation of the vapor. The term "distillate," as used herein, refers the condensed vapor. The term "bottoms," as used herein, refers to the remaining liquid. In a continuous distillation process, the distillate stream exits the top of the distillation column and the bottoms stream exits the bottom of the distillation column.

The process of the invention provides for the recovery of a homogeneous ruthenium catalyst composition from a glycolic acid hydrogenation effluent. The term "glycolic acid hydrogenation effluent," as used herein, is understood to mean the liquid, reaction product resulting from contacting glycolic acid, one or more glycolate esters, glycolic acid oligomers, glycolate oligomer esters, or a mixture thereof with hydrogen in the presence of a homogeneous ruthenium catalyst under hydrogenation conditions of temperature and pressure to produce ethylene glycol. The glycolic acid hydrogenation effluent may be the liquid product directly from the reactor. The glycolic acid hydrogenation effluent also refers to the reaction products, reaction by-products, and the homogeneous ruthenium catalyst composition remaining after one or more intervening steps to remove at least a portion of the ethylene glycol product and/or concentrate the homogeneous ruthenium catalyst. The term "reaction by-products" includes by-products from side reactions, reaction intermediates, and unreacted feeds. Reaction by-products include, but are not limited to glycolic acid, glycolic acid oligomers, ethylene glycol oligomers, glycolate esters, 1,2-propanediol, 1,2-butanediol, and polyols. The term "glycolic acid," as used herein, is intended to include glycolic acid and any glycolic acid derivatives that may be present in the reaction of formaldehyde with carbon monoxide to produce glycolic acid or in the subsequent hydrogenation of glycolic acid to produce ethylene glycol. These glycolic acid derivatives include, but are not limited to, methyl glycolate, mono- and diglycolate esters of ethylene glycol, various oligomers of glycolic acid or glycolate esters, or mixtures thereof. The term "glycolate esters," as used herein, is understood to mean the ester formed between glycolic acid or one or more oligomers of glycolic acid and an alcohol, a diol, or a polyol. Examples of glycolate esters are the glycolate esters of ethylene glycol, which can be a monoester of ethylene glycol and glycolic acid or a glycolic acid oligomer, a diester of ethylene glycol and glycolic acid or a glycolic acid oligomer, or a mixture of mono- and diesters of ethylene glycol and glycolic acid or a glycolic acid oligomers. The term "glycolic acid oligomers" is intended to have its commonly understood meaning in the art, that is a dimer, trimer, or low molecular weight polymer of glycolic acid or a glycolic acid ester typically having 2 to about 20 repeating units. More typically, the glycolic acid oligomers can have 2 to about 6 repeating units. The term "ethylene glycol oligomers," as used herein, refers to diethylene glycol, triethylene glycol, and other low molecular weight polymers of ethylene glycol typically having 2 to about 20 repeating units. The term "polyol," as used herein, refers to species containing more than two OH moieties.

The glycolic acid hydrogenation effluent of the present invention can be produced by contacting glycolic acid, as defined above, with hydrogen at elevated pressures and temperatures in the presence of the homogeneous ruthenium catalyst compositions described herein. Thus, for example, ethylene glycol can be produced from glycolic acid, glycolate esters, oligomers of glycolic acid, esters of glycolic acid oligomers, or mixtures thereof. The glycolic acid may be obtained from any source known in the art such as, for example, from commercial sources. The term "homogeneous catalyst," as used herein refers to any ruthenium compound such as, for example, a ruthenium-phosphine coordination compound that is soluble or partly soluble in the reaction mixture. Similar processes have been described in the art such as, for example, as disclosed in U.S. Pat. No. 7,615,671. In addition to unreacted glycolic acid and hydrogenation catalyst components, the glycolic acid hydrogenation reaction product typically can comprise mono- and bis-glycolate esters of ethylene glycol, ethylene glycol oligomers, glycolic acid, glycolic acid oligomers typically having 2 to 6 glycolic acid repeating units, bis- and mono-esters of ethylene glycol and glycolic acid oligomers typically having two to six glycolic acid units, water, and ethylene glycol.

The term "major amount," as used herein, refers to greater than 50 weight percent. For example, if a major amount of the ethylene glycol in the feed leaves the extraction step in the raffinate, then greater than 50 weight percent of the ethylene glycol fed to the extractor exits the extractor in the reaffinate. The term, "minor amount," as used herein, refers to less than 50 weight percent.

The glycolic acid hydrogenation reaction is conducted for a period of time sufficient to produce the desired products while minimizing unwanted by-products. Persons having ordinary skill in the art will understand that reaction time will be dependent, in part, upon factors such as temperature, pressure, catalyst concentration, nature and proportion of starting materials, and the like. The reaction time will typically be within the range of from about one-half to about 200 hours or more. For example, the reaction time can be from less than about one to about 10 hours.

The hydrogenation of glycolic acid and the resulting glycolic acid hydrogenation effluent may comprise a solvent. The solvent can be water or a hydrophilic organic solvent. The term "hydrophilic," as used herein, is understood to mean that equal volumes of the solvent and water are completely miscible at the temperature of the reaction or extraction processes described herein. Similarly, the term "hydrophobic," is understood to mean that equal volumes of the solvent and water are immiscible or only partially miscible at the reaction or extraction temperature described herein. The solvent should dissolve the catalyst components and reactants, and should not act as a poison to the catalyst. Examples of hydrophilic organic solvents include lower alcohols, glycolic acid hydrogenation reaction starting materials, and glycolic acid hydrogenation reaction products. Some specific examples of hydrophilic organic solvents include methanol, ethanol, propanol, isopropanol, ethylene glycol, glycolic acid, glycolate esters, oligomers of glycolic acid and glycolate esters, 1,2-propylene glycol, 1,3-propylene glycol, 2-methyl-1,3-propanediol, neopentyl glycol, 2-ethylhexanol, 1,4-butanediol, diethylene glycol, triethylene glycol, glycerol, methoxy ethanol, and mixtures thereof.

Our process comprises extracting a glycolic acid hydrogenation effluent comprising about 10 to about 99 weight percent ethylene glycol, about 0.5 to about 50 weight percent water, and about 0.5 to about 40 weight percent of one or more reaction by-products; about 40 to about 99 weight percent ethylene glycol, about 0.5 to about 40 weight percent water, and about 0.5 to about 40 weight percent of one or more reaction by-products; or about 80 to about 95 weight percent ethylene glycol, about 1 to about 15 weight percent water, and about 1 to about 15 weight percent of one or more reaction by-products, each based on the total weight of the glycolic acid hydrogenation effluent. The one or more reaction by-products can be selected from glycolic acid, glycolic acid oligomers, ethylene glycol oligomers, glycolate esters, 1,2-propanediol, 1,2-butanediol, and polyols.

Further examples include a glycolic acid hydrogenation effluent comprising ethylene glycol in an amount ranging from about 10 to about 99 weight percent, about 10 to about 95 weight percent, about 10 to about 90 weight percent, about 10 to about 80 weight percent; about 20 to about 99 weight percent, about 20 to about 95 weight percent, about 20 to about 90 weight percent, about 20 to about 80 weight percent; about 30 to about 99 weight percent, about 30 to about 95 weight percent, about 30 to about 90 weight percent, about 30 to about 80 weight percent; about 40 to about 99 weight percent, about 40 to about 95 weight percent, about 40 to about 90 weight percent, about 40 to about 80 weight percent; about 50 to about 99 weight percent, about 50 to about 95 weight percent, about 50 to about 90 weight percent, about 50 to about 80 weight percent; about 75 to about 99 weight percent, about 75 to about 95 weight percent, about 75 to about 90 weight percent, about 75 to about 80 weight percent; about 80 to about 99 weight percent, about 80 to about 95 weight percent, about 80 to about 90 weight percent; about 85 to about 99 weight percent, about 85 to about 95 weight percent, or about 85 to about 90 weight percent, based on the total weight of the glycolic acid hydrogenation effluent.

Further examples include a glycolic acid hydrogenation effluent comprising water in an amount ranging from about 0.5 to about 50 weight percent, about 0.5 to about 40 weight percent, about 0.5 to about 30 weight percent, about 0.5 to about 25 weight percent, about 0.5 to about 20 weight percent, about 0.5 to about 15 weight percent, about 0.5 to about 10 weight percent; about 1 to about 50 weight percent, about 1 to about 40 weight percent, about 1 to about 30 weight percent, about 1 to about 25 weight percent, about 1 to about 20 weight percent, about 1 to about 15 weight percent, about 1 to about 10 weight percent; about 5 to about 50 weight percent, about 5 to about 40 weight percent, about 5 to about 30 weight percent, about 5 to about 25 weight percent, about 5 to about 20 weight percent, about 5 to about 15 weight percent, or about 5 to about 10 weight percent, based on the total weight of the glycolic acid hydrogenation effluent.

Further examples include a glycolic acid hydrogenation effluent comprising one or more reaction by-products selected from glycolic acid, glycolic acid oligomers, ethylene glycol oligomers, glycolate esters, 1,2-propanediol, 1,2-butanediol, and polyols in an amount ranging from about 0.5 to about 50 weight percent, about 0.5 to about 40 weight percent, about 0.5 to about 30 weight percent, about 0.5 to about 25 weight percent, about 0.5 to about 20 weight percent, about 0.5 to about 15 weight percent, about 0.5 to about 10 weight percent; about 1 to about 50 weight percent, about 1 to about 40 weight percent, about 1 to about 30 weight percent, about 1 to about 25 weight percent, about 1 to about 20 weight percent, about 1 to about 15 weight percent, about 1 to about 10 weight percent; about 5 to about 50 weight percent, about 5 to about 40 weight percent, about 5 to about 30 weight percent, about 5 to about 25 weight percent, about 5 to about 20 weight percent, about 5 to about 15 weight percent, or about 5 to about 10 weight percent, based on the total weight of the glycolic acid hydrogenation effluent.

The hydrogenation reaction may be conducted under moderate conditions using a variety of procedures known in the art. Typically, the hydrogen pressure over the reaction mixture can be about 3.5 to about 27 megapascals (MPa). Lower pressures will generally result in a slower rate of reaction. Higher pressures give a faster rate of reaction, but this is offset by higher operating costs. A typical temperature range for the hydrogenation reaction is about 150 to about 220° C. For example, the hydrogenation of glycolic acid can be carried out at a temperature of about 180 to about 210° C. and a pressure of about 6 to about 16 MPa. The hydrogen feed can comprise at least 95 mole % hydrogen or, in another example, greater than 99 mole % hydrogen.

Any of the known hydrogenation reactor designs or configurations may be used for the hydrogenation reaction to produce the glycolic acid hydrogenation product. For example, the process may be conducted in a batchwise manner in an autoclave by contacting the glycolic acid with hydrogen in the presence of the catalyst compositions described herein. It will be apparent to those skilled in the art that other reactor schemes may be used with this invention. For example, the hydrogenation reaction can be conducted in a plurality of reaction zones, in series, in parallel, or it may be conducted batchwise or continuously in a tubular plug flow reaction zone or series of such zones with recycle of unconsumed feed substrate materials if required. The reaction steps may be carried out by the incremental addition of one of the feed substrate materials to the other. Also, the reaction steps can be combined by the joint addition of the feed substrate materials.

The glycolic acid hydrogenation process and effluent thereof comprise a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes. The source of ruthenium is not particularly limiting and can be any ruthenium compound that is soluble in the hydrogenation reaction medium. Some non-limiting examples of ruthenium compounds include ruthenium salts, hydride complexes, carbonyl compounds, halides, oxides, phosphine complexes, and mixtures thereof. Suitable ruthenium salts include ruthenium carboxylates and acetylacetonates. For example, the ruthenium compound can comprise the acetonylacetonate or diacetate salts of a ruthenium coordination compound with any of the tridentate ligands set forth herein.

The tridentate ligand can comprise at least one phosphine selected from 1,1,1-tris(diarylphosphinomethyl)alkanes and 1,1,1-tris(dialkylphosphinomethyl)alkanes having the formula (I):

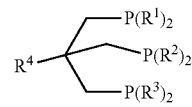

I wherein $R^4$ represents a substituted or unsubstituted, straight or branched chain alkyl radical having 1 to 40 carbon atoms or a substituted or unsubstituted cycloaliphatic radical containing 6 to 40 carbon atoms; and Fe, $R^2$, $R^3$ each independently may be a substituted or unsubstituted alkyl radical having 1 to 40 carbon atoms, an substituted or unsubstituted aryl radical having 6 to 20 carbon atoms, or a substituted or unsubstituted cycloaliphatic radical having 6 to 20 carbon atoms.

The alkyl radicals represented by Fe, $R^2$, $R^3$, and $R^4$ can be substituted with any group that does not interfere with the hydrogenation reaction such as, for example, hydroxyl, ether, halogen, sulfonic acid, carboxylic acid, and the like. Examples of substituted and unsubstituted alkyl radicals include, but are not limited to, methyl, ethyl, cyanomethyl, nitromethyl, hydroxymethyl, trityloxymethyl, propionyloxymethyl, aminomethyl, carboxymethyl, methoxymethyl, ethoxymethyl, butoxymethyl, t-butoxymethyl, acetoxymethyl, chloromethyl, bromomethyl, iodomethyl, 6-hydroxyhexyl, 2,4-dichloro(n-butyl), 2-amino(isopropyl), n-propyl, isopropyl, isobutyl, n-butyl, tertiary butyl, pentyl, hexyl, 2-ethylhexyl, octyl, decyl, and various isomers thereof.

Examples of substituted and unsubstituted cycloalkyl radicals include, but are not limited to, cyclopropyl, cyclobutyl, hydroxymethylcyclobutyl, cyclopentyl, cyclohexyl, cycloheptyl, 2-methylcyclopropyl, 4-methylcyclohexyl, 4-(isopropyl)-cyclohexylethyl or 2-methyl-cyclopropylpentyl, and the like. Examples of substituted and unsubstituted aryl radicals are phenyl, napthyl, anthracenyl, 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl, 4-hydroxyphenyl, 3-hydroxyphenyl, 2,4-dihydroxyphenyl, 4-cyanophenyl, 4-methylphenyl, 2,4-dimethylphenyl, 2-methylnaphthyl, 4-(isopropyl)phenyl, 4-ethylnaphthyl, 3-(n-propyl)phenyl, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl, 3- or 4-trifluoromethylphenyl, 3,4-di(hydroxymethyl)phenyl, 2-(aminomethyl)phenyl, and 3-(methylsulfonylamino)naphthyl.

Exemplary tridentate phosphine ligands include, but are not limited to, 1,1,1-tris(diphenylphosphinomethyl)methane, 1,1,1-tris(diphenylphosphinomethyl)ethane, (2-(butoxymethyl)-2-((diphenylphosphino)methyl)propane-1,3-diyl)bis(diphenylphosphine), (2-(benzyloxymethyl)-2-((diphenylphosphino)methyl)propane-1,3-diyl)bis(diphenylphosphine), 1,1,1-tris(diphenylphosphinomethyl)propane, 1,1,1-tris(diphenylphosphino-methyl)butane, 1,1,1-tris(diphenylphosphinomethyl)-2,2-dimethylpropane, 1,1,1-tris(diphenylphosphinomethyl)cyclohexane, 1,1,1-tris(dicyclohexylphosphinomethyl)ethane, 1,1,1-tris(dimethylphosphinomethyl)ethane, 1,1,1-tris(diethylphosphinomethyl)ethane, or mixtures thereof. For example, the tridentate phosphine can comprise 1,1,1-tris(diphenylphosphinomethyl)ethane (also known as "triphos"), represented by formula (II), 1,1,1-tris(diethylphosphinomethyl)ethane, represented by formula (III), (2-(butoxymethyl)-2-((diphenylphosphino)methyl)propane-1,3-diyl)bis(diphenylphosphine), represented by formula (IV), (2-(benzyloxymethyl)-2-((diphenylphosphino)methyl)propane-1,3-diyl)bis(diphenylphosphine), represented by formula (V), or a poly(alkylenoxymethyl)-2-((diphenylphosphino)methyl)propane-1,3-diyl)bis(diphenylphosphine), represented by formula (VI):

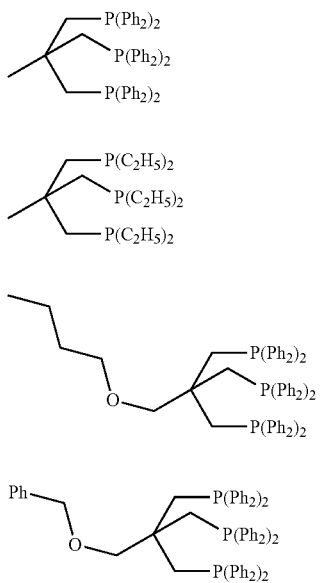

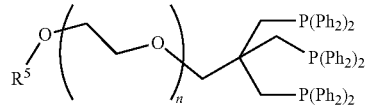

wherein n is 1 to 10 and $R^5$ is an alkyl or substituted alkyl group having 1 to 20 carbon atoms.

In another example, the catalyst composition can comprise a tridentate ligand comprising 1,1,1-tris(diphenylphosphinomethyl)ethane, (2-(butoxymethyl)-2-((diphenylphosphino)methyl)propane-1,3-diyl)bis(diphenylphosphine), (2-(benzyloxymethyl)-2-((diphenylphosphino)methyl)propane-1,3-diyl)bis(diphenylphosphine), or mixtures thereof. In another embodiment, the tridentate ligand can comprise 1,1,1-tris(diphenylphosphinomethyl)ethane.

The phosphorus ligands represented by formulas (IV), (V), and (VI) can show higher solubility in the extraction solvents disclosed herein for the process of the invention in comparison to ligands (II) and (III). These ligands can be readily prepared, as shown in the chemical equations given below, by the reaction of pentaerythritol (VII) with thionyl chloride in presence of pyridine to produce pentaerythrityl tetrachloride (IX) and pentaerythrityl trichlorohydrin (VIII) as disclosed in Mondanaro, K.; Lynch, M.; Dailey, W. *J. Org. Chem.*, 1995, 60, 4666-4668. Compound (VIII) can be reacted with n-butyl bromide in presence of potassium hydroxide (KOH) at low temperature to give 1-(3-Chloro-2,2-bis(chloromethyl)propoxy)butane (X). Compound (X) can then be reacted with 3 equivalents of lithium diphenylphosphide (LiPPh$_2$) in diethoxy methane solvent to form (IV). Persons skilled in the art will recognize that similar steps may be used to prepare compounds (V) and (VI).

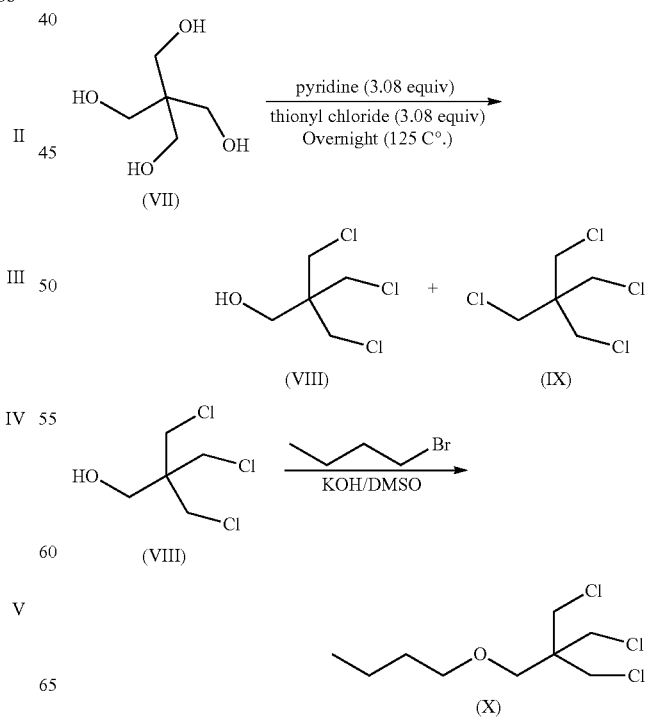

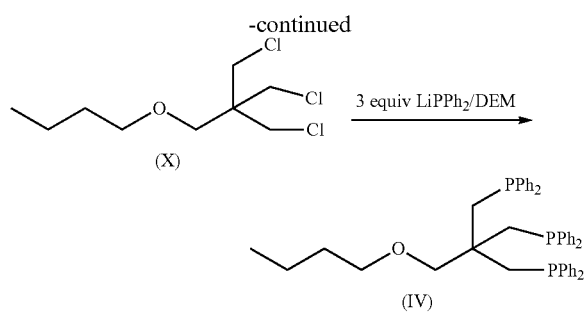

Compounds (IV), (V), and (VI) can be purified by reaction with a limiting amount of tris(triphenylphosphine)ruthenium dichloride (($Ph_3P)_3RuCl_2$) in toluene to produce Cl-bridged complexes of these compounds. These bridged complexes can be isolated by crystallization in high purity and yield.

The concentration of the ruthenium and the tridentate ligand in the glycolic acid hydrogenation reaction mixture or product can vary over a wide range. In general, Ru concentrations (as the free metal) can be in the range of from about 1 part per million to about 10,000 parts per million. For example, Ru concentrations in the range of from about 10 parts per million to about 1,000 parts per million can be used. In another example, the Ru concentration can be 20 parts per million to about 200 parts per million. Typically, a gram mole ligand:gram atom ruthenium ratio of at least 1:1 is maintained in the reaction mixture. More typically, the ratio ranges from 1:1 to 20:1 or 3:1 to 5:1.

The feed can comprise water from the glycolic acid hydrogenation effluent as well as additional water which can be added to aid in the extraction. The feed composition, based on the total weight of the glycolic acid hydrogenation effluent and the additional water, may comprise water in a range from about 1 to about 60 weight percent, about 1 to about 50 weight percent, about 1 to about 40 weight percent, about 1 to about 30 weight percent; about 5 to about 60 weight percent, about 5 to about 50 weight percent, about 5 to about 40 weight percent, about 5 to about 30 weight percent, about 5 to about 20 weight percent; about 10 to about 60 weight percent, about 10 to about 50 weight percent, about 10 to about 40 weight percent, about 10 to about 30 weight percent, or about 10 to about 20 weight percent.

The glycolic acid hydrogenation effluent is contacted with a first extractant that comprises at least one hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof. Some representative examples of hydrophobic solvents include, but are not limited to, 2-ethylhexanol, butanol, pentanol, hexanol, heptanol, octanol, nonanol, decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof. In another example, the hydrophobic solvent comprises 2-ethylhexanol, butanol, pentanol, isobutyl isobutyrate, undecanone, methylisobutyl ketone, diisopropyl ether, or mixtures thereof. For example, in one embodiment of our inventive process, the hydrophobic extraction solvent comprises 2-ethylhexanol. It is understood that an alkanol is intended to encompass all isomers of that alcohol, for example, butanol refers to n-butanol, isobutanol, sec-butanol, and/or tert-butanol.

Mixtures of one or more different hydrophobic solvents may be employed if desired. The amount of hydrophobic extraction solvent employed is not critical to the subject invention and need only be that amount sufficient to extract the catalyst complex from the glycolic acid hydrogenation effluent for any given process and to ensure the formation of two immiscible liquid phases throughout the extraction zones. In general, the amount of hydrophobic extraction solvent employed may range from about 5 percent by weight up to about 500 percent by weight or more based on the total weight of the extractor feed which is the glycolic acid hydrogenation effluent and any additional water. The use of the high percentage of hydrophobic extraction solvent may be necessary, for example, when there are only a limited number of stages in a countercurrent extraction process.

The first extractant may optionally comprise a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having 2 to 6 carbon atoms, acetic acid, formic acid, α-hydroxy carboxylic acids having from 4 to 6 carbon atoms, glycolic acid oligomers having 2 to 6 repeat units, glycolate esters, and mixtures thereof. For purposes of this invention, one or more glycolic acid hydrogenation products or reactants may be used as the hydrophilic solvent. In general, the amount of hydrophilic solvent employed may range from about 1 weight percent, based on the total weight of the extractant, to about 60 weight percent. Some additional weight percent ranges of the hydrophilic solvent are about 1 to about 50 weight percent and about 1 to about 40 weight percent.

As noted above, the optional, hydrophilic solvent used in the first extractant can be a hydrophilic component present in the glycolic acid hydrogenation effluent. For example, in the hydrogenation of glycolate esters to produce ethylene glycol, the optional, hydrophilic extraction solvent can comprise ethylene glycol. In another example, the hydrophilic solvent can comprise one or more glycolate esters as described hereinabove. The optional hydrophilic solvent can be introduced to the extraction process at one or more different locations. In one embodiment, for example, the optional hydrophilic solvent can be added to the first extractant. In another embodiment, the hydrophilic solvent can be added to the first extractant directly, to the glycolic acid hydrogenation effluent, or to the extractor containing a mixture of the extractant and glycolic acid hydrogenation effluent. In another embodiment, the hydrophilic solvent can be introduced into the extractor as a separate feed. In yet another embodiment, the extractor may be operated as a fractional extractor with one or more hydrophilic extraction solvent feed points. In still another embodiment, for example, the hydrophilic extraction solvent for the forward extraction zone can be water. In still another embodiment, sufficient water can be added to the extractor to produce a water content in the a first raffinate phase exiting the forward extraction zone of about 0 to 60 weight percent water or, in another example about 5 to 35 weight percent water, based on the total weight of the first raffinate phase.

The ratio of the hydrophilic and hydrophobic solvents used in the process of the invention can depend on the composition of the glycolic acid hydrogenation effluent. For example, as the concentration of the hydrophilic or hydrophobic solvents in the glycolic acid hydrogenation effluent becomes lower, it may be required to increase the ratio of the hydrophobic extraction solvent to the glycolic acid hydrogenation effluent, the ratio of the hydrophilic extraction solvent to the glycolic acid hydrogenation effluent, or both. Generally, the volume ratio of either the hydrophilic or hydrophobic extraction solvent to the glycolic acid hydrogenation effluent may be changed within a range of from about 20:1 to about 1:20.

The hydrophobic solvent of the first extractant may further comprise a hydrocarbon to modify the physical and transport properties of the extractant. The hydrocarbon can have from 5 to 20 carbon atoms. Some representative examples of hydrocarbons include hexane, heptane, octane, decane, benzene, toluene, xylenes, methyl napththalenes, isoparaffinic mixed hydrocarbons having a boiling range between 90 and 325° C., and mixtures thereof. For example, the hydrocarbon may comprise isoparaffinic mixed hydrocarbons having boiling ranges between about 90 and about 325° C., as exemplified by the ISOPAR™ solvents, such as ISOPAR C (boiling point range of 98 to 104° C.), Isopar E (boiling point range of 118 to 137° C.), ISOPAR G (boiling point range of 160 to 176° C.), ISOPAR H (boiling point range of 178 to 188° C.), ISOPAR K (boiling point range of 178 to 197° C.), ISOPAR L (boiling point range of 189 to 207° C.), ISOPAR C (boiling point range of 223 to 254° C.), and ISOPAR V (boiling point range of 273 to 312° C.).

In some aspects of the invention, the hydrocarbon can be lower boiling than the other hydrophobic solvent components and, thus, can be readily separated from the other components by distillation. If more than one hydrophobic solvent is used as the first extractant, these solvents may or may not form azeotropic mixtures under distillation conditions employed.

The extraction of the glycolic acid hydrogenation effluent can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal extractors (e.g., those produced by Robatel, Luwesta, deLaval, Dorr Oliver, Bird, CINC, and Podbielniak), and other miscellaneous extractors (e.g., emulsion phase contactor, electrically enhanced extractors, and membrane extractors). A description of these devices can be found in the "Handbook of Solvent Extraction," Krieger Publishing Company, Malabar, Fla., 1991, pp. 275-501. The various types of extractors may be used alone or in any combination.

The extraction may be conducted in one or more stages. The number of extraction stages can be selected in consideration of capital costs, achieving high extraction efficiency, ease of operability, and the stability of the starting materials and reaction product to the extraction conditions. The extraction also can be conducted in a batch or continuous fashion. In a continuous mode, the extraction may be carried out in a co-current manner, a counter-current manner, or as a fractional extraction in which multiple solvents and/or solvent feed points are used to help facilitate the separation. The extraction process also can be conducted in a plurality of separation zones that can be in series or in parallel.

The extraction typically can be carried out at a temperature of about 10 to about 120° C. For example, the extraction can be conducted at a temperature of about 30 to about 80° C. The desired temperature range may be constrained further by the boiling point of the extractant components. Generally, it is undesirable to operate the extraction under conditions where the extractant boils. In one embodiment, the extractor can be operated to establish a temperature gradient across the extractor in order to improve the mass transfer kinetics or decantation rates.

The glycolic acid hydrogenation effluent and extractant can be contacted by fractional extraction methods such as, for example, by fractional countercurrent extraction. As used herein, the term "fractional countercurrent extraction" is intended to include, but is not limited to, a method for separating a feed stream, e.g., glycolic acid hydrogenation effluent, containing two or more substances by charging the feed stream to a countercurrent extraction process between the points where two immiscible solvents are charged to the extraction process. The two immiscible solvents should be immiscible over the entire temperature range of the extraction process. This method is sometimes referred to as "double solvent extraction." Fractional countercurrent extraction can involve the use of a cascade of stages, extracting solvents and solution to be extracted entering at opposite ends of the cascade with the feed phase and hydrophobic extractant phase flowing counter currently. Some example fractional countercurrent extraction configurations may be found in Treybal, *Liquid Extraction,* 2nd Edition, McGraw-Hill Book Company, New York. 1963, pp. 275-276.

When conducted in a fractional extraction mode, the hydrophobic extraction solvent typically can be added to the extraction zone at a point closer to the end of the extractor where the first raffinate phase exits the extraction zone and further away from the optional hydrophilic extraction solvent feed point. The mass feed ratio of the hydrophilic solvent contained in the glycolic acid hydrogenation effluent and the hydrophilic extraction solvent added directly to the forward extraction zone typically can be between about 0 and 1.5. In another example, the mass feed ratio can be between about 0.05 to 0.45.

The extraction of the glycolic acid hydrogenation effluent produces a first raffinate phase comprising a major amount of the ethylene glycol contained in the glycolic acid hydrogenation effluent and a first extract phase comprising a major amount of the catalyst composition in the glycolic acid hydrogenation effluent. The first raffinate phase and the first extract phase may be separated by any phase separation technology known in the art. The phase separation techniques can be accomplished in the extractor or in a separate liquid-liquid separation device. Suitable liquid-liquid separation devices include, but are not limited to, coalescers, cyclones and centrifuges. Typical equipment that can be used for liquid-liquid phase separation devices are described in the *Handbook of Separation process Technology*, ISBN 0-471-89558-X, John Wiley & Sons, Inc., 1987.

The percent Ru recovered in the forward extraction step is the amount of Ru in the first extract phase divided by the amount of Ru in the extractor feed times 100. Thus, in one aspect of our invention the Ru recovery of the forward extraction step is greater than 80 percent, greater than 90 percent, greater than 95 percent, or greater than 99 percent.

The catalyst composition in the first extract phase can be separated from the extractant by either extraction or distillation. The catalyst composition can be back-extracted from the first extract phase into a hydrophilic solvent that subsequently can be used directly as a reactant in the glycolic acid hydrogenation reaction. Thus, our process also comprises extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase. Typically, the concentration of Ru in the second extract phase can be about 10 parts per million to about 10,000 parts per million or, in another example, about 20 parts per million to about 200 parts per million, and recycled to the glycolic acid hydrogenation reaction without further concentration of the catalyst. In one aspect of our invention the ruthenium is recovered from the first extract phase into the second extract phase at a level of greater than 80 percent, greater than 90 percent, greater than 95 percent, or greater than 99 percent.

Alternatively, the extractant can be distilled from the catalyst composition of the first extract phase and the remaining catalyst composition can be recycled to the glycolic acid hydrogenation reaction. Thus, our process also comprises distilling the first extract phase of step (B) to form a distillate comprising a major amount of the hydrophobic solvent contained in the first extract phase of step (B) and a bottoms comprising a major amount of the catalyst composition contained in the first extract phase of step (B).

The distillation operation of the instant invention may be carried out in batch or continuous modes of operation, with any gas/liquid contacting device known in the art suitable for distillation practice. The gas/liquid contacting equipment of the distillation operation may include, but is not limited to, cross-flow sieve, valve, or bubble cap trays, structured packings such as Mellapak®, Metpak®, Rombopak®, Flexipak®, Gempak®, Goodloe®, Sulzer, Koch-Sulzer, York-Twist® or random or dumped packing, such as berl saddles, Intalox saddles, Raschig rings, Pall rings, Hy-Pak® rings, Cannon packing, and Nutter rings. These and other types of suitable gas/liquid contacting equipment are described in Kister, H. Z. Distillation Design, McGraw-Hill, New York (1992), Chapters 6 and 8.

The second extract phase or bottoms can be passed to a process for the preparation of ethylene glycol by hydrogenation of glycolic acid, glycolate esters, glycolic acid oligomers, or mixtures thereof. The second raffinate phase or distillate can be recycled to the first extraction by combining the second raffinate phase or distillate with the first extractant. The second raffinate phase can be distilled prior to recycle to produce a hydrophobic solvent distillate that is subsequently combined with the extractant of step (A). Thus, in another embodiment, the process of the invention can further comprise combining the second raffinate phase of step (C) with the first extractant of step (A), distilling the second raffinate phase of step (C) to produce a hydrophobic solvent distillate and combining the hydrophobic solvent distillate with the first extractant of step (A), or combining the distillate of step (C) with the first extractant of step (A).

The weight ratio of the second extractant to the first extract phase of step (B) of our inventive process can be about 0.05:1 to about 2:1. Further examples of weight ratios of the second extractant to the first extract phase are about 0.1:1 to 2:1 and about 0.1:1 to about 1:1.

The extraction process can be conducted at a temperature of about 10 to about 120° C. For example, in one embodiment of the invention, steps (A), (B) and the extraction of step (C) of the invention are carried out at a temperature of about 30 to about 80° C.

In another embodiment of our process, the second extractant can comprise mono- and diglycolate esters of ethylene glycol. In another example, the catalyst composition can comprise 1,1,1-tris(diphenylphosphinomethyl)ethane, the first extractant can comprise a hydrophobic solvent comprising 2-ethylhexanol and heptane, and the second extractant can comprise mono- and diglycolate esters of ethylene glycol.

The extraction step (C) also can be carried out by any extraction means known in the art such, for example, by fractional extraction methods. For example, the catalyst composition can recovered by extracting the first extract phase of step (B), and step (A) and/or step (C) can be carried out by fractional countercurrent extraction.

One aspect of our invention is a process for recovering a homogeneous catalyst, comprising
(A) extracting a feed comprising
 (i) a glycolic acid hydrogenation effluent, comprising
  (a) about 40 to about 99 weight percent ethylene glycol, about 0.5 to about 40 weight percent water, and about 0.5 to 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
  (b) a catalyst composition comprising ruthenium and 1,1,1-tris(diphenylphosphinomethyl)ethane: and
 (ii) additional water whereby the feed comprises about 5 to about 40 weight percent water based on the total weight of the glycolic acid hydrogenation effluent and the additional water;
 with a first extractant, comprising about 60 to 100 weight percent 2-ethylhexanol, pentanol, isobutyl isobutyrate, undecanone, methylisobutyl ketone, diisopropyl ether, or mixtures thereof and 0 to about 40 weight percent of a hydrocarbon having from 5 to 20 carbon atoms, each based on the total weight of the first extractant, to form a first raffinate phase comprising a major amount of the ethylene glycol and a minor amount of the catalyst composition contained in the glycolic acid hydrogenation effluent and a first extract phase comprising a major amount of the catalyst composition and a minor amount of the ethylene glycol contained in the glycolic acid hydrogenation effluent;
(B) separating the first raffinate phase and the first extract phase; and
(C) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); and
(D) combining the second raffinate phase of step (C) with the first extractant of step (A), or distilling the second raffinate phase of step (C) to produce a hydrophobic solvent distillate and combining the hydrophobic solvent distillate with the first extractant of step (A).

It is understood that the above process comprises the various embodiments of the glycolic acid hydrogenation effluent, the catalyst composition, the first extractant, the second extractant, equipment used to carry out the extractions, and the first and second extract phases steps as described previously. For example, the glycolic acid hydrogenation product can comprise about 40 to about 99 weight percent ethylene glycol, about 0.5 to about 40 weight percent water, and about 0.5 to 40 weight percent of the one or more reaction by-products noted above. In another example, the glycolic acid hydrogenation effluent can comprise about 80 to about 95 weight percent ethylene glycol, about 1 to about 15 weight percent water, and about 1 to about 15 weight percent of one or more reaction by-products described above, and the above catalyst composition. The feed can comprise about 5 to about 40 weight percent water based on the total weight of the glycolic acid hydrogenation effluent and the additional water. In another example, the feed can comprise about 10 to about 30 weight percent water based on the total weight of the glycolic acid hydrogenation effluent and the additional water.

The first extractant comprises about 60 to 100 weight percent 2-ethylhexanol, butanol, pentanol, isobutyl isobutyrate, undecanone, methylisobutyl ketone, diisopropyl ether, or mixtures thereof and 0 to about 40 weight percent of a hydrocarbon having 5 to 20 carbon atoms, each based on the total weight of the first extractant. Some representative examples of hydrocarbons include hexane, heptane, octane, decane, benzene, toluene, xylenes, methyl napththalenes, and mixtures thereof. For example, the hydrophobic solvent can comprise 2-ethylhexanol and heptane.

As noted previously, the extraction of the glycolic acid hydrogenation effluent can be carried out by any means known in the art to intimately contact two immiscible liquid phases and to separate the resulting phases after the extraction procedure. For example, the extraction can be carried out using columns, centrifuges, mixer-settlers, and miscellaneous devices. The various types of extractors may be used alone or in any combination.

The extraction may be conducted in one or more stages. The extraction also can be conducted in a batch or continuous fashion. In a continuous mode, the extraction may be carried out in a co-current manner, a counter-current manner, or as a fractional extraction in which multiple solvents and/or solvent feed points are used to help facilitate the separation. Further, the extraction process of this invention can be conducted in a plurality of separation zones in series or in parallel. The extraction typically can be carried out at a temperature of about 10 to about 120° C. The glycolic acid hydrogenation effluent and extractant can be contacted by fractional extraction methods such as, for example, by fractional countercurrent extraction as described above.

The extraction produces a first raffinate phase comprising a major amount of the ethylene glycol contained in the glycolic acid hydrogenation effluent and a first extract phase comprising a major amount of the catalyst composition in the glycolic acid hydrogenation effluent. The raffinate and extract phases may be separated by any phase separation technology known in the art as described hereinabove.

The catalyst composition can be back-extracted from the first extract phase into a solvent mixture that subsequently can be used directly as a reactant in the glycolic acid hydrogenation reaction. Thus, our process also comprises extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase.

The second extract phase can be passed to a process for the preparation of ethylene glycol by hydrogenation of glycolic acid, glycolate esters, glycolic acid oligomers, or mixtures thereof. The second raffinate phase can be recycled to the first extraction by combining the second raffinate phase with the first extractant. The second raffinate phase can be distilled prior to recycle to produce a hydrophobic solvent distillate that is subsequently combined with the extractant of step (A). Thus, in another embodiment, the process of the invention can further comprise combining the second raffinate phase of step (C) with the first extractant of step (A), or distilling the second raffinate phase of step (C) to produce a hydrophobic solvent distillate and combining the hydrophobic solvent distillate with the first extractant of step (A).

In one embodiment of our process, the glycolic acid hydrogenation effluent comprises ethylene glycol, ruthenium and at least one phosphine selected from 1,1,1-tris(diarylphosphinomethyl)alkanes and 1,1,1-tris(dialkylphosphinomethyl)alkanes, water, and one or more reaction by-products. The glycolic acid hydrogenation effluent is fed to the forward extraction zone, wherein the glycolic acid hydrogenation effluent is contacted in a countercurrent extraction column with a hydrophobic solvent extractant. The hydrophobic solvent comprises 2-ethylhexanol or pentanol, and a hydrocarbon solvent. Water is optionally added to the forward extractor as the hydrophilic solvent as necessary to improve the extractor performance based on physical and transport properties as well as the equilibrium. The hydrophilic raffinate phase comprises a majority of the ethylene glycol. The hydrophobic solvent to feed ratio and staging is adjusted such that the amount of phosphine-Ru catalyst composition lost with the hydrophilic raffinate phase is economically acceptable and does not require a subsequent recovery step. The hydrophobic extract phase may be then fed to a back extraction zone, wherein the hydrophobic extract phase can be contacted in a countercurrent extraction column with a hydrophilic extractant, comprising the feed substrate to the reaction zone, i.e., glycolic acid, mono and bis glycolates of ethylene glycol, oligomers of glycolic acid, and the like. An additional second hydrophobic solvent optionally can be added to the back extractor as necessary to improve the extractor performance. This second hydrophobic solvent may comprise a hydrocarbon having 5 to 20 carbon atoms such as, for example, hexane, heptane, octane, decane, benzene, toluene, xylenes, methyl napththalenes, or mixtures thereof. The second hydrophobic solvent to feed ratio and staging is adjusted such that the amount of phosphine-Ru catalyst complex lost with the second raffinate phase is economically acceptable and does not require a subsequent recovery step. The second extract phase from the back extraction zone is suitable to charge to the hydrogenation reactor directly after it exits the back extraction zone. The second raffinate phase is suitable for recycle to the forward extraction zone as the hydrophobic solvent.

Optionally, an additional hydrophobic solvent may be employed to modify the physical and transport properties of the hydrophobic extractant mixture prior to introduction into the back extraction zone. This additional hydrophobic solvent can be the same as the optional, second hydrophobic solvent employed in the forward extraction zone. The optional addition of the second hydrophobic extraction solvent can be used to remove any unwanted relatively hydrophobic components from the hydrophilic extraction phase of the back extractor zone. In one embodiment, the second hydrophobic extraction solvent is not required, and the second extractor is operated as a traditional extractor instead of as a fractional extractor.

Alternatively, the back extraction zone may be operated in a fractional extraction mode with the additional second hydrophobic solvent added at a feed point closer to the end of the extractor where the raffinate stream exits than the feed point of the hydrophobic extract phase from the forward extraction zone. Preferably the mass feed ratio of the additional second hydrophobic solvent to the hydrophobic extract phase from the forward extraction zone is between 0 and 1.5, more preferably about 0.05 to 0.45.

In one embodiment the glycolic acid hydrogenation effluent comprises about 80 to about 95 weight percent ethylene glycol, about 1 to about 15 weight percent water, and about 1 to about 15 weight percent of the one or more reaction by-products, and wherein the feed comprises about 10 to about 30 weight percent water based on the total weight of the glycolic acid hydrogenation effluent and the additional water. In another embodiment the hydrophobic solvent comprises 2-ethylhexanol and heptane, and further comprising passing the second extract phase of step (C) to a process for the preparation of ethylene glycol by hydrogenation of glycolic acid, glycolate esters, glycolic acid oligomers, or mixtures thereof to ethylene glycol.

As noted above, the process of the invention can comprise recycling the recovered catalyst composition to a process for the preparation of ethylene glycol by hydrogenation of glycolic acid, glycolate esters, glycolic acid oligomers, or mixtures thereof. Thus, another embodiment of our invention is a process for recovering a homogeneous catalyst, comprising (A) contacting an aqueous mixture comprising glycolic acid, glycolate esters, methyl glycolate, oligomers of glycolic acid, or mixtures thereof, with hydrogen in the presence of a catalyst composition comprising ruthenium and 1,1,1-tris(diphenylphosphinomethyl)ethane to form a glycolic acid hydrogenation effluent comprising about 80 to about 95 weight percent ethylene glycol, about 0.5 to about 15 weight percent water, and about 0.5 to about 15 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent, and the catalyst composition;

(B) extracting a feed comprising the glycolic acid hydrogenation effluent and additional water whereby the feed comprises about 10 to about 30 weight percent water, based on the total weight of the glycolic acid hydrogenation effluent and the additional water, with a first extractant comprising about 60 to 100 weight percent 2-ethylhexanol and 0 to about 40 weight percent of a hydrocarbon having 5 to 20 carbon atoms, each based on the total weight of the first extractant, to form a first raffinate phase comprising a major amount of the ethylene glycol contained in the glycolic acid hydrogenation effluent and a first extract phase comprising a major amount of the catalyst composition contained in the glycolic acid hydrogenation effluent;

(C) separating the first raffinate phase and the first extract phase;

(D) extracting the first extract phase of step (D) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (C) and a second raffinate phase comprising a minor amount of the catalyst composition contained in the first extract phase of step (C); and (E) combining the second extract phase of step (C) with the aqueous mixture of step (A).

It is understood that the above process comprises the various embodiments of the glycolic acid hydrogenation effluent, the catalyst composition, the first extractant, the second extractant, equipment used to carry out the extractions, and the first and second extract phases steps as described previously. For example, the glycolic acid hydrogenation product can comprise about 80 to about 95 weight percent, based on the total weight of the glycolic acid hydrogenation product, ethylene glycol, about 0.5 to about 15 weight percent water, and about 0.5 to about 15 weight percent of one or more reaction by-products described above, and the above catalyst composition.

The first extractant can comprise about 60 to 100 weight percent, based on the total weight of the first extractant, 2-ethylhexanol and about 0 to about 40 weight percent of a hydrocarbon having 5 to 20 carbon atoms. Some representative examples of hydrocarbons include hexane, heptane, octane, decane, benzene, toluene, xylenes, methyl napththalenes, and mixtures thereof. For example, the hydrophobic solvent can comprise 2-ethylhexanol and heptane.

The extraction produces a first raffinate phase comprising a major amount of the ethylene glycol contained in the glycolic acid hydrogenation effluent and a first extract phase comprising a major amount of the catalyst composition in the glycolic acid hydrogenation effluent. The raffinate and extract phases may be separated by any phase separation technology known in the art as described hereinabove.

The catalyst composition can be back-extracted from the first extract phase into a solvent mixture that subsequently can be used directly as a reactant in the glycolic acid hydrogenation reaction. Thus, our process also comprises extracting the first extract phase of step (C) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (C) and a second raffinate phase comprising a minor amount of the catalyst composition contained in the first extract phase.

The second extract phase can be passed to a process for the preparation of ethylene glycol by hydrogenation of glycolic acid, glycolate esters, glycolic acid oligomers, or mixtures thereof. The second raffinate phase can be recycled to the first extraction by combining the second raffinate phase with the first extractant. The second raffinate phase can be distilled prior to recycle to produce a hydrophobic solvent distillate that is subsequently combined with the extractant of step (B). Thus, in another embodiment, the process of the invention can further comprise combining the second raffinate phase of step (D) with the first extractant of step (B), or distilling the second raffinate phase of step (D) to produce a hydrophobic solvent distillate and combining the hydrophobic solvent distillate with the first extractant of step (B).

In an embodiment of our invention the glycolic acid hydrogenation effluent is concentrated with at least a portion of the ethylene glycol and water removed from the one or more reaction by-products and catalyst composition. The concentration step can be performed by any means known in the art, such as, for example, distillation. The majority of the concentrated glycolic acid hydrogenation effluent is recycled back to the glycolic acid hydrogenation reactor. A portion of the concentrated glycolic acid hydrogenation effluent is processed to remove at least a portion of the one or more reaction by-products and recover the catalyst composition to be recycled to the glycolic acid hydrogenation reactor.

Thus, one aspect of our invention is a process for recovering a homogeneous catalyst, comprising (A) extracting a feed comprising
  (i) a glycolic acid hydrogenation effluent, comprising
    (a) about 0.5 to about 50 weight percent ethylene glycol, about 0.5 to about 50 weight percent water, and about 25 to 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
    (b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes: and
(ii) additional water whereby the feed comprises about 5 to about 95 weight percent water based on the total weight of the glycolic acid hydrogenation effluent and the additional water;
with a first extractant, comprising
(i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
(ii) optionally, a hydrophilic solvent;
to form a first raffinate phase comprising a major amount of the one or more reaction by-products and a minor amount of the catalyst composition contained in the glycolic acid hydrogenation effluent and a first extract phase comprising a major amount of the catalyst composition and a minor amount of the one or more reaction by-products contained in the glycolic acid hydrogenation effluent;
(B) separating the first raffinate phase and the first extract phase; and
(C) recovering the catalyst composition from the first extract phase of step (B) by:
(i) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); or
(ii) distilling the first extract phase of step (B) to form a distillate comprising a major amount of the hydrophobic solvent contained in the first extract phase of step (B) and a bottoms comprising a major amount of the catalyst composition contained in the first extract phase of step (B).

It is understood that the above process comprises the various embodiments of the catalyst composition, the first extractant, the second extractant, equipment used to carry out the extractions, the first and second extract phase steps, and the distillation as described previously. For example, the catalyst composition ruthenium and a tridentate ligand comprising at least one phosphine selected from 1,1,1-tris(diarylphosphinomethyl)alkanes and 1,1,1-tris(dialkylphosphinomethyl)alkanes as described above.

Our process comprises extracting a glycolic acid hydrogenation effluent comprising about 0.5 to about 50 weight percent ethylene glycol, about 0.5 to about 50 weight percent water, and about 25 to about 99 weight percent of one or more reaction by-products; about 0.5 to about 30 weight percent ethylene glycol, about 0.5 to about 30 weight percent water, and about 40 to about 99 weight percent of the one or more reaction by-products; or about 0.5 to about 20 weight percent ethylene glycol, about 0.5 to about 20 weight percent water, and about 70 to about 99 weight percent of the one or more reaction by-products, based on the total weight of the glycolic acid hydrogenation effluent.

Further examples include a glycolic acid hydrogenation effluent comprising ethylene glycol in an amount ranging from about 0.5 to about 50 weight percent, about 0.5 to about 40 weight percent, about 0.5 to about 30 weight percent, about 0.5 to about 20 weight percent; about 1 to about 50 weight percent, about 1 to about 40 weight percent, about 1 to about 30 weight percent, about 1 to about 20 weight percent; about 5 to about 50 weight percent, about 5 to about 40 weight percent, about 5 to about 30 weight percent, about 5 to about 20 weight percent; about 10 to about 50 weight percent, about 10 to about 40 weight percent, about 10 to about 30 weight percent, or about 10 to about 20 weight percent, based on the total weight of the glycolic acid hydrogenation effluent.

Further examples include a glycolic acid hydrogenation effluent comprising water in an amount ranging from about 0.5 to about 50 weight percent, about 0.5 to about 40 weight percent, about 0.5 to about 30 weight percent, about 0.5 to about 20 weight percent; about 1 to about 50 weight percent, about 1 to about 40 weight percent, about 1 to about 30 weight percent, about 1 to about 20 weight percent; about 5 to about 50 weight percent, about 5 to about 40 weight percent, about 5 to about 30 weight percent, about 5 to about 20 weight percent; about 10 to about 50 weight percent, about 10 to about 40 weight percent, about 10 to about 30 weight percent, or about 10 to about 20 weight percent, based on the total weight of the glycolic acid hydrogenation effluent.

Further examples include a glycolic acid hydrogenation effluent comprising one or more reaction by-products selected from glycolic acid, glycolic acid oligomers, ethylene glycol oligomers, glycolate esters, 1,2-propanediol, 1,2-butanediol, and polyols, in an amount ranging from about 10 to about 99 weight percent, about 10 to about 95 weight percent, about 10 to about 90 weight percent, about 10 to about 80 weight percent; about 20 to about 99 weight percent, about 20 to about 95 weight percent, about 20 to about 90 weight percent, about 20 to about 80 weight percent; about 30 to about 99 weight percent, about 30 to about 95 weight percent, about 30 to about 90 weight percent, about 30 to about 80 weight percent; about 40 to about 99 weight percent, about 40 to about 95 weight percent, about 40 to about 90 weight percent, about 40 to about 80 weight percent; about 50 to about 99 weight percent, about 50 to about 95 weight percent, about 50 to about 90 weight percent, about 50 to about 80 weight percent; about 70 to about 99 weight percent, about 70 to about 95 weight percent, about 70 to about 90 weight percent, about 70 to about 80 weight percent; about 80 to about 99 weight percent, about 80 to about 95 weight percent, about 80 to about 90 weight percent, about 85 to about 99 weight percent, about 85 to about 95 weight percent, or about 85 to about 90 weight percent, based on the total weight of the glycolic acid hydrogenation effluent.

The feed can comprise water from the glycolic acid hydrogenation effluent as well as additional water which can be added to aid in the extraction. The feed composition, based on the total weight of the glycolic acid hydrogenation effluent and the additional water, may comprise water in a range from about 5 to about 95 weight percent, about 5 to about 90 weight percent, about 5 to about 85 weight percent, about 5 to about 75 weight percent; about 10 to about 95 weight percent, about 10 to about 90 weight percent, about 10 to about 85 weight percent, about 10 to about 75 weight percent; about 25 to about 95 weight percent, about 25 to about 90 weight percent, about 25 to about 85 weight percent, or about 25 to about 75 weight percent.

The glycolic acid hydrogenation effluent is contacted with a first extractant that comprises at least one hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof. Some representative examples of hydrophobic solvents include, but are not limited to, 2-ethylhexanol, butanol, pentanol, hexanol, heptanol, octanol, nonanol, decanol, tetradecanol isomers, methyl isobutylketone, methyl isopropylketone, isobutylisobutyrate, ethyl acetate, n-butyl acetate, isobutylacetate, isopropylacetate, n-propyl acetate, diispropylether, dibutylether, tertiary-amyl methyl ether, 2-ethylhexanoic acid, and mixtures thereof. In another example, the hydrophobic solvent comprises 2-ethylhexanol, butanol, pentanol, isobutyl isobutyrate, undecanone, methylisobutyl ketone, diisopropyl ether, or mixtures thereof. For example, in one embodiment of our inventive process, the hydrophobic extraction solvent comprises 2-ethylhexanol. It is understood that an alkanol is intended to encompass all isomers of that alcohol, for example, butanol refers to n-butanol, isobutanol, sec-butanol, and/or tert-butanol.

Mixtures of one or more different hydrophobic solvents may be employed if desired. The hydrophobic solvent of the first extractant may further comprise a hydrocarbon to modify the physical and transport properties of the extractant. The hydrocarbon can have from 5 to 20 carbon atoms. Some representative examples of hydrocarbons include hexane, heptane, octane, decane, benzene, toluene, xylenes, methyl napththalenes, isoparaffinic mixed hydrocarbons having a boiling range between 90 and 325° C., and mixtures thereof. The amount of hydrophobic extraction solvent employed is not critical to the subject invention and need only be that amount sufficient to extract the catalyst complex from the glycolic acid hydrogenation effluent for any given process and to ensure the formation of two immiscible liquid phases throughout the extraction zones. In general, the amount of hydrophobic extraction solvent employed may range from about 5 percent by weight up to about 500 percent by weight or more based on the total weight of the extractor feed which is the glycolic acid hydrogenation effluent and any additional water. The use of the high percentage of hydrophobic extraction solvent may be necessary, for example, when there are only a limited number of stages in a countercurrent extraction process.

As noted previously, the extraction of the glycolic acid hydrogenation effluent can be carried out by any means known in the art to intimately contact two immiscible liquid phases and to separate the resulting phases after the extraction procedure. For example, the extraction can be carried out using columns, centrifuges, mixer-settlers, and miscellaneous devices. The various types of extractors may be used alone or in any combination.

The extraction may be conducted in one or more stages. The extraction also can be conducted in a batch or continuous fashion. In a continuous mode, the extraction may be carried out in a co-current manner, a counter-current manner, or as a fractional extraction in which multiple solvents and/or solvent feed points are used to help facilitate the separation. Further, the extraction process of this invention can be conducted in a plurality of separation zones in series or in parallel. The extraction typically can be carried out at a temperature of about 10 to about 120° C. The glycolic acid hydrogenation effluent and extractant can be contacted by fractional extraction methods such as, for example, by fractional countercurrent extraction as described above.

The catalyst composition in the first extract phase can be separated from the extractant by either extraction or distillation. The catalyst composition can be back-extracted from the first extract phase into a hydrophilic solvent that subsequently can be used directly as a reactant in the glycolic acid hydrogenation reaction. Thus, our process also comprises extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase. Typically, the concentration of Ru in the second extract phase can be about 10 parts per million to about 10,000 parts per million or, in another example, about 20 parts per million to about 200 parts per million, and recycled to the glycolic acid hydrogenation reaction without further concentration of the catalyst. In one aspect of our invention the ruthenium is recovered from the first extract phase into the second extract phase at a level of greater than 80 percent, greater than 90 percent, greater than 95 percent, or greater than 99 percent.

Alternatively, the extractant can be distilled from the catalyst composition of the first extract phase and the remaining catalyst composition can be recycled to the glycolic acid hydrogenation reaction. Thus, our process also comprises distilling the first extract phase of step (B) to form a distillate comprising a major amount of the hydrophobic solvent contained in the first extract phase of step (B) and a bottoms comprising a major amount of the catalyst composition contained in the first extract phase of step (B). The distillation can be performed by any means known in the art such as described herein above.

The second extract phase or bottoms can be passed to a process for the preparation of ethylene glycol by hydrogenation of glycolic acid, glycolate esters, glycolic acid oligomers, or mixtures thereof. The second raffinate phase or distillate can be recycled to the first extraction by combining the second raffinate phase or distillate with the first extractant. The second raffinate phase can be distilled prior to recycle to produce a hydrophobic solvent distillate that is subsequently combined with the extractant of step (A). Thus, in another embodiment, the process of the invention can further comprise combining the second raffinate phase of step (C) with the first extractant of step (A), distilling the second raffinate phase of step (C) to produce a hydrophobic solvent distillate and combining the hydrophobic solvent distillate with the first extractant of step (A), or combining the distillate of step (C) with the first extractant of step (A). In one embodiment, the catalyst composition is recovered by extracting the first extract phase of step (B), and step (A) and/or step (C) are carried out by fractional countercurrent extraction.

In one embodiment of our process, the glycolic acid hydrogenation effluent comprises ethylene glycol, ruthenium and at least one phosphine selected from 1,1,1-tris(diarylphosphinomethyl)alkanes and 1,1,1-tris(dialkylphosphinomethyl)alkanes, water, and one or more reaction by-products. The glycolic acid hydrogenation effluent is fed to the forward extraction zone, wherein the glycolic acid hydrogenation effluent is contacted in a countercurrent extraction column with a hydrophobic solvent extractant. The hydrophobic solvent comprises 2-ethylhexanol or pentanol, and a hydrocarbon solvent. Water is optionally added to the forward extractor as the hydrophilic solvent as necessary to improve the extractor performance based on physical and transport properties as well as the equilibrium. The hydrophilic raffinate phase comprises a majority of the one or more reaction by-products. The hydrophobic solvent to feed ratio and staging is adjusted such that the amount of phosphine-Ru catalyst composition lost with the hydrophilic raffinate phase is economically acceptable and does not require a subsequent recovery step. The hydrophobic extract phase may be then fed to a back extraction zone, wherein the hydrophobic extract phase can be contacted in a countercurrent extraction column with a hydrophilic extractant, comprising the feed substrate to the reaction zone, i.e., glycolic acid, mono and bis glycolates of ethylene glycol, oligomers of glycolic acid, and the like. An additional second hydrophobic solvent optionally can be added to the back extractor as necessary to improve the extractor performance. This second hydrophobic solvent may comprise a hydrocarbon having 5 to 20 carbon atoms such as, for example, hexane, heptane, octane, decane, benzene, toluene, xylenes, methyl napththalenes, or mixtures thereof. The second hydrophobic solvent to feed ratio and staging is adjusted such that the amount of phosphine-Ru catalyst complex lost with the second raffinate phase is economically acceptable and does not require a subsequent recovery step. The second extract phase from the back extraction zone is suitable to charge to the hydrogenation reactor directly after it exits the back extraction zone. The second raffinate phase is suitable for recycle to the forward extraction zone as the hydrophobic solvent.

Optionally, an additional hydrophobic solvent may be employed to modify the physical and transport properties of the hydrophobic extractant mixture prior to introduction into the back extraction zone. This additional hydrophobic solvent can be the same as the optional, second hydrophobic solvent employed in the forward extraction zone. The optional addition of the second hydrophobic extraction solvent can be used to remove any unwanted relatively hydrophobic components from the hydrophilic extraction phase of the back extractor zone. In one embodiment, the second hydrophobic extraction solvent is not required, and the second extractor is operated as a traditional extractor instead of as a fractional extractor.

Alternatively, the back extraction zone may be operated in a fractional extraction mode with the additional second hydrophobic solvent added at a feed point closer to the end of the extractor where the raffinate stream exits than the feed point of the hydrophobic extract phase from the forward extraction zone. Preferably the mass feed ratio of the additional second hydrophobic solvent to the hydrophobic extract phase from the forward extraction zone is between 0 and 1.5, more preferably about 0.05 to 0.45.

In another embodiment of our process, the catalyst composition is recovered by extracting the first extract phase of step (B) and the second extractant comprises mono- and diglycolate esters of ethylene glycol. In one example, the tridentate ligand comprises 1,1,1-tris(diphenylphosphinomethyl)ethane, the hydrophobic solvent comprises pentanol and heptane, and the catalyst composition is recovered by distilling the first extract phase of step (B). In another embodiment, the process comprises passing the second extract phase or the bottoms of step (C) to a process for the preparation of ethylene glycol by hydrogenation of glycolic acid, glycolate esters, glycolic acid oligomers, or mixtures thereof to ethylene glycol.

One aspect of our invention is a process for recovering a homogeneous catalyst, comprising
(A) extracting a feed comprising
 (i) a glycolic acid hydrogenation effluent, comprising
  (a) about 0.5 to about 30 weight percent ethylene glycol, about 0.5 to about 30 weight percent water, and about 40 to 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
  (b) a catalyst composition comprising ruthenium and 1,1,1-tris(diphenylphosphinomethyl)ethane: and
 (ii) additional water whereby the feed comprises about 10 to about 90 weight percent water based on the total weight of the glycolic acid hydrogenation effluent and the additional water;
 with a first extractant, comprising about 60 to 100 weight percent 2-ethylhexanol, butanol, pentanol, isobutyl isobutyrate, undecanone, methylisobutyl ketone, diisopropyl ether, or mixtures thereof, and 0 to about 40 weight percent of a hydrocarbon having 5 to 20 carbon atoms, each based on the total weight of the first extractant, to form a first raffinate phase comprising a major amount of the one or more reaction by-products and a minor amount of the catalyst composition contained in the glycolic acid hydrogenation effluent and a first extract phase comprising a major amount of the catalyst composition and a minor amount of the one or more reaction by-products contained in the glycolic acid hydrogenation effluent;
(B) separating the first raffinate phase and the first extract phase; and
(C) distilling the first extract phase of step (B) to form a distillate comprising a major amount of the hydrophobic solvent contained in the first extract phase of step (B) and a bottoms comprising a major amount of the catalyst composition contained in the first extract phase of step (B); and
(D) combining the distillate of step (C) with the first extractant of step (A).

It is understood that the above process comprises the various embodiments of the glycolic acid hydrogenation effluent, the catalyst composition, the first extractant, equipment used to carry out the extraction, the first extract phases step, and the distillation as described previously. For example, the glycolic acid hydrogenation effluent can comprise from about 0.5 to about 30 weight percent ethylene glycol, about 0.5 to about 30 weight percent water, and about 40 to 99 weight percent of one or more reaction by-products. In another example, the glycolic acid hydrogenation effluent can comprise from about 0.5 to about 20 weight percent ethylene glycol, about 0.5 to about 20 weight percent water, and about 70 to about 99 weight percent of the one or more reaction by-products, each based on the total weight of the glycolic acid hydrogenation effluent and the feed comprises about 10 to about 86 weight percent water based upon the total of the glycolic acid hydrogenation effluent and additional water. In one example, the hydrophobic solvent comprises pentanol and heptane and the bottoms is passed to a process for the preparation of ethylene glycol by hydrogenation of glycolic acid, glycolate esters, glycolic acid oligomers, or mixtures thereof to ethylene glycol.

One aspect of our invention is a process for recovering a homogeneous catalyst, comprising
(A) contacting an aqueous mixture comprising glycolic acid, glycolate esters, methyl glycolate, oligomers of glycolic acid, or mixtures thereof, with hydrogen in the presence of a catalyst composition comprising ruthenium and 1,1,1-tris(diphenylphosphinomethyl)ethane to form a glycolic acid hydrogenation product, concentrating the glycolic acid hydrogenation product to form a glycolic acid hydrogenation effluent comprising about 0.5 to about 20 weight percent ethylene glycol, about 0.5 to about 20 weight percent water, and about 70 to about 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent, and the catalyst composition;

(B) extracting a feed comprising the glycolic acid hydrogenation effluent and additional water whereby the feed comprises about 10 to about 85 weight percent water, based on the total weight of the glycolic acid hydrogenation effluent and the additional water, with a first extractant, comprising about 60 to 100 weight percent pentanol and about 0 to about 40 weight percent of a hydrocarbon having 5 to 20 carbon atoms, each based on the total weight of the first extractant, to form a first raffinate phase comprising a major amount of the one or more reaction by-products contained in the glycolic acid hydrogenation effluent and a first extract phase comprising a major amount of the catalyst composition contained in the glycolic acid hydrogenation effluent;

(C) separating the first raffinate phase and the first extract phase;

(D) distilling the first extract phase of step (C) to form a distillate comprising a major amount of the hydrophobic solvent contained in the first extract phase of step (C) and a bottoms comprising a major amount of the catalyst composition contained in the first extract phase of step (C); and (E) combining the bottoms of step (D) with the aqueous mixture of step (A).

It is understood that the above process comprises the various embodiments of the glycolic acid hydrogenation effluent, the catalyst composition, the first extractant, equipment used to carry out the extraction, the first extract phase step, and the distillation as described previously. For example, the glycolic acid hydrogenation effluent can comprise about 0.5 to about 20 weight percent ethylene glycol, about 0.5 to about 20 weight percent water, and about 70 to about 99 weight percent of one or more reaction by-products, each based on the total weight of the glycolic acid hydrogenation effluent and the catalyst composition, as described above.

The first extractant can comprise about 60 to 100 weight percent pentanol and about 0 to about 40 weight percent of a hydrocarbon having 5 to 20 carbon atoms, each based on the total weight of the first extractant. Some representative examples of hydrocarbons include hexane, heptane, octane, decane, benzene, toluene, xylenes, methyl napththalenes, and mixtures thereof. For example, the hydrophobic solvent can comprise pentanol and heptane.

The extraction produces a first raffinate phase comprising a major amount of the one or more reaction by-products contained in the glycolic acid hydrogenation effluent and a first extract phase comprising a major amount of the catalyst composition in the glycolic acid hydrogenation effluent. The raffinate and extract phases may be separated by any phase separation technology known in the art as described hereinabove.

The first extract phase can be distilled with the hydrophobic solvent leaving the distillation step in the distillate and the catalyst composition leaving in the bottoms. The distillate can be recycled to the extractant of step (B). The bottoms can optionally be mixed with the feed to the glycolic acid hydrogenation reaction and be fed to the glycolic acid hydrogenation reaction.

The efficiency of the extraction process of the invention can be measured by a partition coefficient of the Ruthenium, abbreviated herein as "P(Ru)," which is defined as the concentration of the Ru in the hydrophobic phase divided by the concentration of the Ru in the hydrophilic phase. The partition coefficient may be determined by analysis of metal content by known methods such as, for example, X-ray or ICP analysis.

When the Ru is partitioned between the hydrophilic phase and the hydrophobic phase by the forward extraction process of the invention, the P(Ru) value can be maintained at a level greater than about 1, preferably greater than about 2, and more preferably greater than about 4, depending on the efficiency of the extraction process. If the P(Ru) value is high, Ru will preferentially distribute into the hydrophobic phase.

Similarly, the efficiency of this extraction process also can be measured by a partition coefficient of one or more products or reaction by-products present in the glycolic acid hydrogenation product effluent, abbreviated herein as "P(PROD)." P(PROD) is defined as the concentration of the one or more products in the hydrophobic phase divided by the concentration of the one or more products in the hydrophilic phase.

When the one or more desired products or reaction by-products are partitioned between the hydrophilic phase and the hydrophobic phase by the forward extraction process of this invention, the P(PROD) value of the products can be maintained at a level less than about 1, preferably less than about 0.75, and more preferably less than about 0.5, depending on the efficiency of the extraction process. If this P(PROD) value is low, the products will preferentially distribute into the hydrophilic phase.

The extraction factor ("EF") defining selectivity of the hydrophobic phase for the Ru with respect to the one or more products is a partition coefficient ratio, EF=P(Ru)/P(PROD). The EF value for this ratio can be maintained at a level greater than about 2.5. Other values of EF include greater than about 3.0 and greater than about 3.5. If this EF value is high, the extraction selectivity will be high.

FIGS. 1 through 6 represent six, non-limiting embodiments of the instant invention, described herein in detail. In a first embodiment of the invention as laid out in FIG. 1, the effluent stream 15 from Reaction Zone 3, comprising a glycolic acid hydrogenation reaction product, Ru tridentate phosphine ligand complex, and reaction by-products, is optionally combined in Mixing Zone 4 with hydrophilic solvent stream 16, to produce stream 17. Stream 17 is fed counter currently to Forward Extractor 1, wherein the stream is intimately contacted with hydrophobic solvent stream 12. Two products exit the Forward Extractor 1, the hydrophilic raffinate product stream 18 depleted of catalyst and ligand, and the catalyst-ligand laden, hydrophobic extract stream 11. The catalyst-rich stream 11 is fed counter currently to a second extraction zone, Back Extractor 2, wherein the stream is intimately contacted with the hydrophilic feed substrate mixture 10, which typically contains a mixture of glycolic acid, mono- and bis-glycolate esters of ethylene glycol, glycolic acid or glycolate ester oligomers, and water. Two products are withdrawn from the Back Extractor 2, the raffinate stream 12 comprising the lean recycle solvent to Forward Extractor 1, and the extract stream 13, comprising a portion of the feed substrate and recovered catalyst-ligand complex. Extract stream 13 passes to Reaction Zone 3 for transformation into products ultimately exiting the process via stream 18. Any remaining feed substrate needed to meet production requirements in stream 18, but not required for the back extraction of the catalyst enters, Reaction Zone 3 via conduit 14.

At times it may be advantageous to modify physical and transport properties the of the hydrophobic solvent stream between the forward and back extraction steps in order to enhance selectivity or recovery of the catalyst-ligand complex in either or both extraction steps. Such a modification may be accomplished by the addition or removal of one or more components comprising the hydrophobic extractant mixture as laid out in the embodiment of the instant invention illustrated in FIG. 2. The effluent stream 15 from Reaction Zone 3, comprising a hydrophilic reaction product, metal catalyst-ligand complex, and reaction by-products, is optionally combined in Mixing Zone 4 with hydrophilic solvent stream 16, to produce stream 17. Stream 17 is fed counter currently to Forward Extractor 1 wherein the stream is intimately contacted with hydrophobic solvent stream 20. Two products exit the Forward Extractor 1, the hydrophilic raffinate product stream 18 depleted of catalyst and ligand, and the catalyst-ligand laden extract stream 11. The catalyst-rich stream 11 is combined with additional hydrophobic solvent species of stream 19 in Mixing Zone 5, and then fed counter currently to a second extraction zone, Back Extractor 2, wherein the stream is intimately contacted with the hydrophilic feed substrate mixture 10. Two products are withdrawn from the Back Extractor 2. The raffinate stream 12 comprising the lean hydrophobic recycle solvent is conveyed to Separation Zone 6, wherein the additional hydrophobic solvent species of stream 19 are recovered and the original hydrophobic solvent composition of stream 20 is recycled to Forward Extractor 1. The other product of Back Extractor 2, extract stream 13, comprising a portion of the feed substrate and recovered catalyst-ligand complex, passes to Reaction Zone 3 for transformation into products. The reaction products ultimately exit the process via stream 18. Any remaining feed substrate needed to meet production requirements in stream 18, but not required for the back extraction of the catalyst enters, Reaction Zone 3 via conduit 14.

In the previously described first and second embodiments of the instant invention, conventional extraction, i.e., extractions involving a single solvent feed point, are utilized for the forward and back extraction zones. It may be advantageous, however, to operate the forward or back extraction zones as fractional countercurrent extractions in which additional hydrophobic solvent components or hydrophilic solvent components are introduced as separate feeds. In a third embodiment of the invention as set forth in FIG. 3, the effluent stream 15 from Reaction Zone 3, comprising a glycolic acid hydrogenation reaction product, metal catalyst-ligand complex, and reaction by-products, is optionally combined in Mixing Zone 4 with hydrophilic solvent stream 16, to produce stream 17. Stream 17 is fed counter currently to Forward Extractor 1 wherein the stream is intimately contacted with hydrophobic solvent stream 12. When operated as a fractional extractor, an additional hydrophilic solvent stream 21, which may comprise the same or similar components to stream 16, is introduced into Forward Extractor 1 above stream 17. Two products exit the Forward Extractor 1, the hydrophilic raffinate product stream 18 depleted of catalyst and ligand, and the catalyst-ligand laden extract stream 11. The purpose of feed stream 21 is to further reduce losses of reaction products into stream 11. The catalyst-rich stream 11 is fed counter currently to a second extraction zone, Back Extractor 2, wherein the stream is intimately contacted with the hydrophilic feed substrate mixture 10. Two products are withdrawn from the Back Extractor 2, the raffinate stream 12 comprising the lean recycle solvent to Forward Extractor 1, and the extract stream 13, comprising a portion of the feed substrate (which typically contains a mixture of glycolic acid, mono- and bis-glycolate esters of ethylene glycol, glycolic acid or glycolate ester oligomers, and water) and recovered catalyst-ligand complex. Extract stream 13 passes to Reaction Zone 3 for transformation into products ultimately exiting the process via stream 18. Any remaining feed substrate needed to meet production requirements in stream 18, but not required for the back extraction of the catalyst, enters Reaction Zone 3 via conduit 14.

Figure 4:
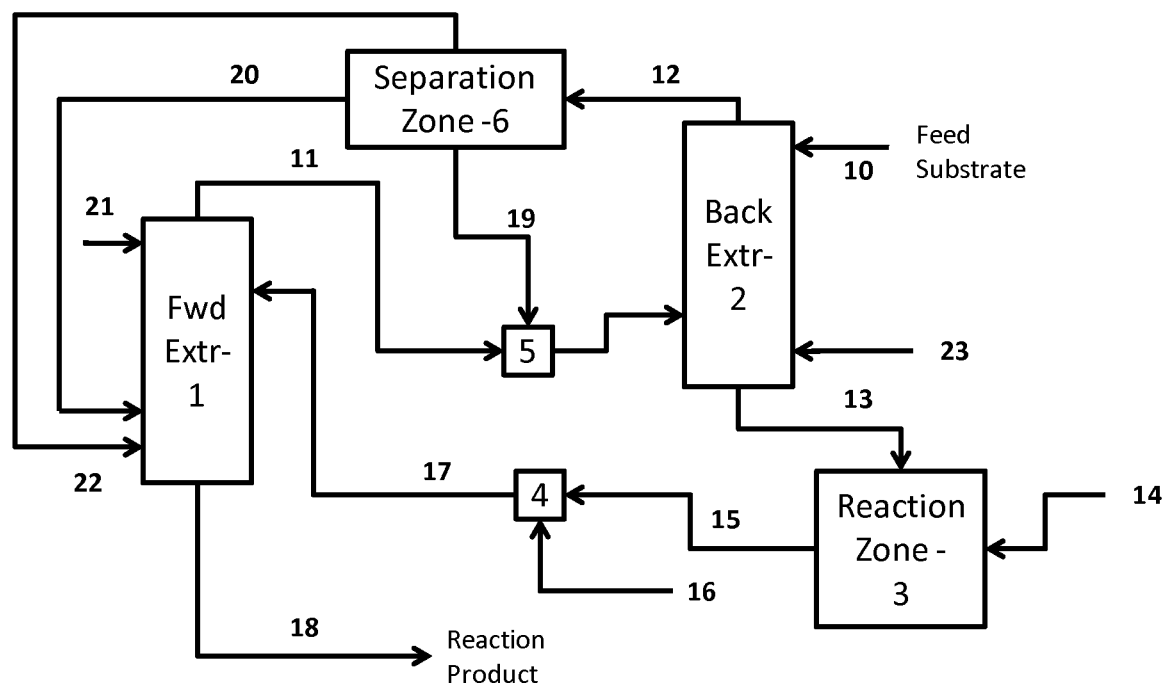
FIG. 4 is a schematic flow diagram for yet another embodiment of the invention in which the extraction process illustrated in FIG. 2 is further modified by additional fractional extraction streams.

The above embodiment may be further modified by additional fractional extraction streams as laid out in the fourth embodiment of the instant invention, FIG. 4. The effluent stream 15 from Reaction Zone 3, comprising a glycolic acid hydrogenation reaction product, metal catalyst-ligand complex, and reaction by-products, is optionally combined in Mixing Zone 4 with hydrophilic solvent stream 16, to produce stream 17. Stream 17 is fed counter currently to Forward Extractor 1 wherein the stream is intimately contacted with hydrophobic solvent stream 20. When operated as a fractional extractor, an additional hydrophilic solvent stream 21, which may comprise the same or similar components to stream 16, is introduced into Forward Extractor 1 above stream 17. An additional hydrophobic solvent stream 22 may be introduced below feed 21. Two products exit the Forward Extractor 1, the hydrophilic raffinate product stream 18 depleted of catalyst and ligand, and the catalyst-ligand laden extract stream 11. The purposes of feed streams 21 and 22 are to further reduce losses of reaction products into stream 11 and to prevent carryover of hydrophobic components into reaction product 18 respectively. The catalyst-rich stream 11 is combined with additional hydrophobic solvent species of stream 19 in Mixing Zone 5, and then fed counter currently to a second extraction zone, Back Extractor 2, wherein the stream is intimately contacted with the hydrophilic feed substrate mixture 10, which typically contains a mixture of glycolic acid, mono- and bis-glycolate esters of ethylene glycol, glycolic acid or glycolate ester oligomers, and water. Additional hydrophobic solvent components may be added via stream 23 to Back Extractor 2 in fractional extraction mode. Two products are withdrawn from the Back Extractor 2. The raffinate stream 12 comprising the lean recycle solvent is conveyed to Separation Zone 6, wherein the additional hydrophobic solvent species of streams 19, 20, and 22 are recovered and the original hydrophobic solvent composition of stream 20 is recycled to Forward Extractor 1. The other product of Back Extractor 2, extract stream 13, comprising a portion of the feed substrate and recovered catalyst-ligand complex, passes to Reaction Zone 3 for transformation into products. The reaction products ultimately exit the process via stream 18. Any remaining feed substrate needed to meet production requirements in stream 18, but not required for the back extraction of the catalyst, enters Reaction Zone 3 via conduit 14.

Figure 5:
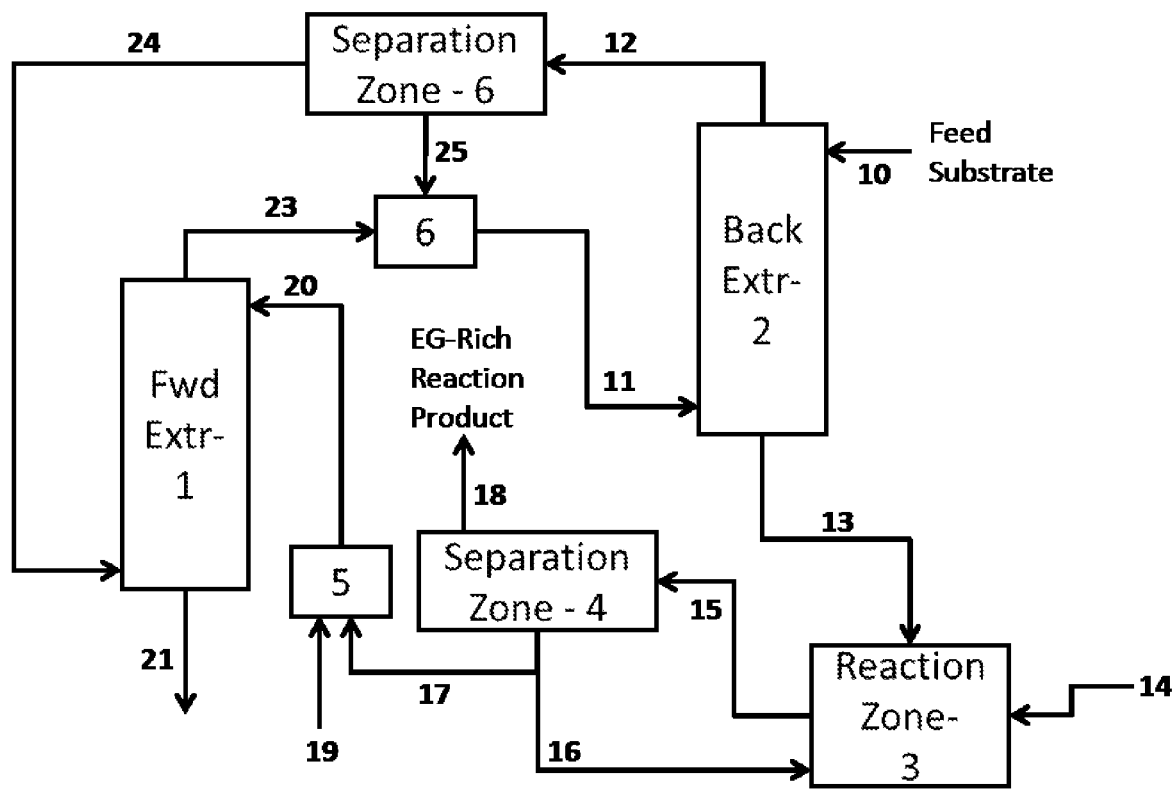
FIG. 5 is a schematic flow diagram for yet another embodiment of the invention in which a glycolic acid hydrogenation product is first fractionated into an ethylene glycol rich stream and a concentrated glycolic acid hydrogenation effluent, and the glycolic acid hydrogenation effluent is subject to the extraction process of FIG. 2.

In the embodiment illustrated by FIG. 5, the effluent stream 15 from Reaction Zone 3, comprising a glycolic acid hydrogenation reaction product, Ru tridentate phosphine ligand complex, and reaction by-products, is first fractionated in Separation Zone 4, where an EG-rich reaction product stream 18 is produced. EG-lean stream 16, containing the catalyst complex and reaction by-products, is recycled back to Reaction Zone 3. EG-lean stream 17 is optionally combined in Mixing Zone 5 with hydrophilic solvent stream 19, to produce stream 20. Stream 20 is fed countercurrently to Forward Extractor 1, wherein the stream is intimately contacted with hydrophobic solvent stream 24. Two products exit the Forward Extractor 1, the hydrophilic raffinate product stream 21 depleted of catalyst and ligand and rich in reaction by-products, and the catalyst-ligand laden, hydrophobic extract stream 23. The catalyst-rich stream 23 is optionally combined with additional hydrophobic solvent species of stream 25 in Mixing Zone 6 to form stream 11 which is fed countercurrently to a second extraction zone, Back Extractor 2, wherein the stream is intimately contacted with the hydrophilic feed substrate mixture 10. Two products are withdrawn from the Back Extractor 2. The raffinate stream 12 comprising the lean hydrophobic recycle solvent is conveyed to Separation Zone 6, wherein the additional hydrophobic solvent species of stream 25 are recovered and the original hydrophobic solvent composition of stream 24 is recycled to Forward Extractor 1. The other product of Back Extractor 2, extract stream 13, comprising a portion of the feed substrate and recovered catalyst-ligand complex, passes to Reaction Zone 3 for transformation into products. The reaction products ultimately exit the process via stream 18. Any remaining feed substrate needed to meet production requirements in stream 18, but not required for the back extraction of the catalyst enters Reaction Zone 3 via conduit 14.

Figure 6:
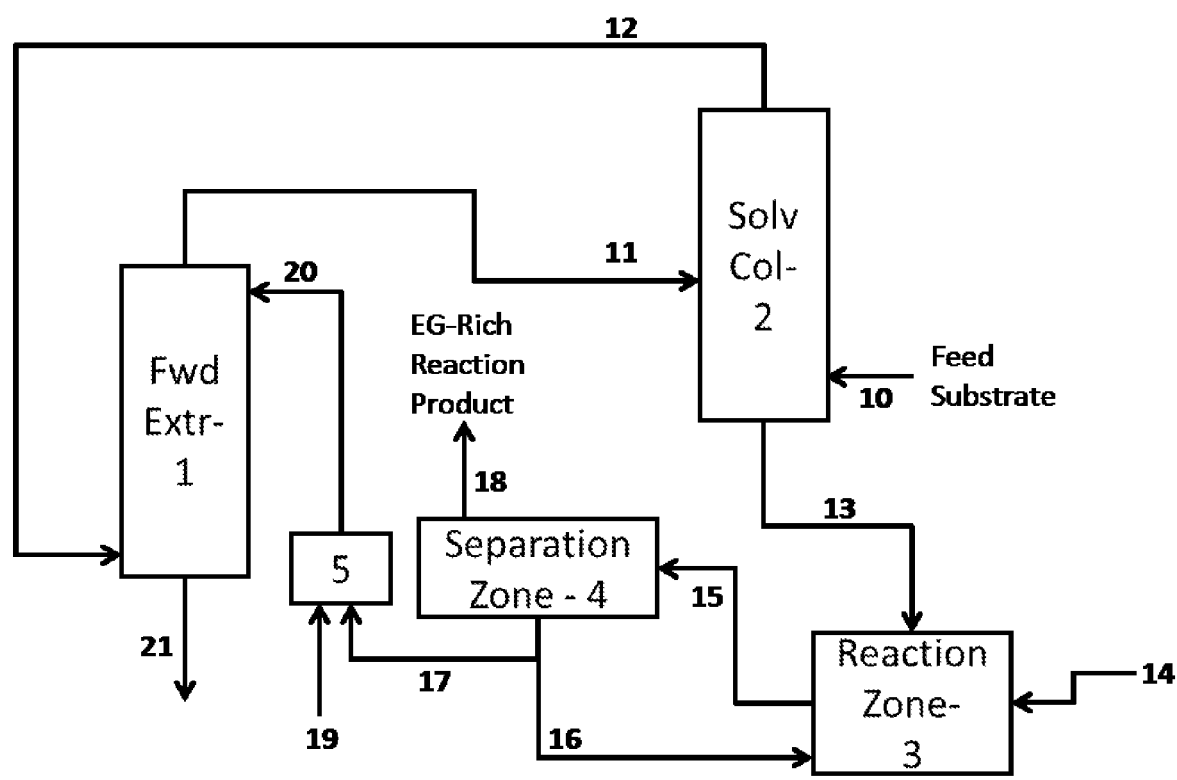
FIG. 6 is a schematic flow diagram for another embodiment of the invention in which the back extraction process illustrated in FIG. 5 is replaced with a distillation column.

In the embodiment illustrated in FIG. 6, the effluent stream 15 from Reaction Zone 3, comprising a glycolic acid hydrogenation reaction product, Ru tridentate phosphine ligand complex, and reaction by-products, is first fractionated in Separation Zone 4, where an EG-rich reaction product stream 18 is produced. EG-lean stream 16, containing the catalyst complex and reaction by-products, is recycled back to Reaction Zone 3. EG-lean stream 17 is optionally combined in Mixing Zone 5 with hydrophilic solvent stream 19, to produce stream 20. Stream 20 is fed countercurrently to Forward Extractor 1, wherein the stream is intimately contacted with hydrophobic solvent stream 12. Two products exit the Forward Extractor 1, the hydrophilic raffinate product stream 21 depleted of catalyst and ligand and rich in reaction by-products, and the catalyst-ligand laden, hydrophobic extract stream 11. The catalyst-rich stream 11 is then fed to a distillation column, Solvent Column 2, where the hydrophilic feed substrate mixture 10 may also be fed to the column. Two products are withdrawn from Solvent Column 2. The distillate, stream 12, comprising the lean hydrophobic solvent is recycled to Forward Extractor 1. The bottoms, stream 13, comprising a portion of the feed substrate and recovered catalyst-ligand complex, passes to Reaction Zone 3 for transformation into products. Any remaining feed substrate needed to meet production requirements in stream 18, but not required for the distillation step, enters Reaction Zone 3 via conduit 14.

Non-Limiting Embodiments

Embodiment A is a process for recovering a homogeneous catalyst, comprising
(A) extracting a feed comprising
(i) a glycolic acid hydrogenation effluent, comprising
(a) about 10 to about 99 weight percent ethylene glycol, about 0.5 to about 50 weight percent water, and about 0.5 to about 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
(b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes: and
(ii) additional water whereby the feed comprises about 5 to about 50 weight percent water based on the total weight of the glycolic acid hydrogenation effluent and the additional water;
with a first extractant, comprising
(i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
(ii) optionally, a hydrophilic solvent;
to form a first raffinate phase comprising a major amount of the ethylene glycol and a minor amount of the catalyst composition contained in the glycolic acid hydrogenation effluent and a first extract phase comprising a major amount of the catalyst composition and a minor amount of the ethylene glycol contained in the glycolic acid hydrogenation effluent;
(B) separating the first raffinate phase and the first extract phase; and
(C) recovering the catalyst composition from the first extract phase of step (B) by:
(i) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); or
(ii) distilling the first extract phase of step (B) to form a distillate comprising a major amount of the hydrophobic solvent contained in the first extract phase of step (B) and a bottoms comprising a major amount of the catalyst composition contained in the first extract phase of step (B).

The process of Embodiment A wherein the glycolic acid hydrogenation effluent comprises about 40 to about 99 weight percent ethylene glycol, about 0.5 to about 40 weight percent water, and about 0.5 to about 40 weight percent of one or more reaction by-products; or about 80 to about 95 weight percent ethylene glycol, about 1 to about 15 weight percent water, and about 1 to about 15 weight percent of one or more reaction by-products.

The process of Embodiment A or Embodiment A with one or more of the intervening features, wherein the feed comprises about 10 to about 30 weight percent water based on the total weight of the glycolic acid hydrogenation effluent and the additional water.

The process of Embodiment A or Embodiment A with one or more of the intervening features, wherein the tridentate ligand comprises 1,1,1-tris(diphenylphosphinomethyl)methane, 1,1,1-tris(diphenylphosphinomethyl)ethane, (2-(butoxymethyl)-2-((diphenylphosphino)methyl)propane-1,3-diyl)bis(diphenylphosphine), (2-(benzyloxymethyl)-2-((diphenylphosphino)methyl)propane-1,3-diyl)bis(diphenylphosphine), 1,1,1-tris(diphenylphosphinomethyl)propane, 1,1,1-tris(diphenylphosphinomethyl)butane, 1,1,1-tris(diphenylphosphinomethyl)-2,2-dimethylpropane, 1,1,1-tris(diphenylphosphinomethyl)cyclohexane, 1,1,1-tris(dicyclohexylphosphinomethyl)ethane, 1,1,1-tris(dimethylphosphinomethyl)ethane, 1,1,1-tris(diethylphosphinomethyl)ethane, or mixtures thereof.

The process of Embodiment A or Embodiment A with one or more of the intervening features, wherein the tridentate ligand comprises 1,1,1-tris(diphenylphosphinomethyl)ethane.

The process of Embodiment A or Embodiment A with one or more of the intervening features, wherein the hydrophobic solvent is selected from 2-ethylhexanol, butanol, pentanol, hexanol, heptanol, octanol, nonanol, decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof.

The process of Embodiment A or Embodiment A with one or more of the intervening features, wherein the hydrophobic solvent further comprises a hydrocarbon having from 5 to 20 carbon atoms.

The process of Embodiment A or Embodiment A with one or more of the intervening features, wherein the hydrophobic solvent further comprises a hydrocarbon having from 5 to 20 carbon atoms and the hydrocarbon is selected from hexane, heptane, octane, decane, benzene, toluene, xylenes, methyl napththalenes, isoparaffinic mixed hydrocarbons having a boiling range between 90 and 325° C., and mixtures thereof.

The process of Embodiment A or Embodiment A with one or more of the intervening features, wherein the first extractant comprises a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having from 2 to 6 carbon atoms, acetic acid, formic acid, α-hydroxy carboxylic acids having from 4 to 6 carbon atoms, glycolic acid oligomers having from 2 to 6 repeat units, polyol and diol esters of glycolic acid, and mixtures thereof.

The process of Embodiment A or Embodiment A with one or more of the intervening features, wherein the catalyst composition is recovered by extracting the first extract phase of step (B), and wherein the second extractant comprises mono- and diglycolate esters of ethylene glycol.

The process of Embodiment A or Embodiment A with one or more of the intervening features, wherein the catalyst composition is recovered by extracting the first extract phase of step (B), and wherein the second extractant comprises mono- and diglycolate esters of ethylene glycol, and wherein the tridentate ligand comprises 1,1,1-tris(diphenylphosphinomethyl)ethane and the hydrophobic solvent comprises 2-ethylhexanol and heptane.

The process of Embodiment A or Embodiment A with one or more of the intervening features, further comprising passing the second extract phase or the bottoms of step (C) to a process for the preparation of ethylene glycol by hydrogenation of glycolic acid, glycolate esters, glycolic acid oligomers, or mixtures thereof to ethylene glycol.

The process of Embodiment A or Embodiment A with one or more of the intervening features, further comprising combining the second raffinate phase of step (C) with the first extractant of step (A), distilling the second raffinate phase of step (C) to produce a hydrophobic solvent distillate and combining the hydrophobic solvent distillate with the first extractant of step (A), or combining the distillate of step (C) with the first extractant of step (A).

The process of Embodiment A or Embodiment A with one or more of the intervening features, wherein the catalyst composition is recovered by extracting the first extract phase of step (B), and wherein step (A) and/or step (C) are carried out by fractional countercurrent extraction.

The process of Embodiment A or Embodiment A with one or more of the intervening features, therein the first extractant comprises about 60 to 100 weight percent 2-ethylhexanol, pentanol, isobutyl isobutyrate, undecanone, methylisobutyl ketone, diisopropyl ether, or mixtures thereof and 0 to about 40 weight percent of a hydrocarbon having from 5 to 20 carbon atoms, each based on the total weight of the first extractant.

The process of Embodiment A or Embodiment A with one or more of the intervening features, wherein the recovering of the catalyst composition from the first extract of step (B) is by extracting the first extract of step (B).

Embodiment B is a process for recovering a homogeneous catalyst, comprising
(A) extracting a feed comprising
  (i) a glycolic acid hydrogenation effluent, comprising
    (a) about 0.5 to about 50 weight percent ethylene glycol, about 0.5 to about 50 weight percent water, and about 25 to 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of the glycolic acid hydrogenation effluent; and
    (b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes: and
  (ii) additional water whereby the feed comprises about 5 to about 95 weight percent water based on the total weight of the glycolic acid hydrogenation effluent and the additional water;
  with a first extractant, comprising
  (i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
  (ii) optionally, a hydrophilic solvent;
  to form a first raffinate phase comprising a major amount of the one or more reaction by-products and a minor amount of the catalyst composition contained in the glycolic acid hydrogenation effluent and a first extract phase comprising a major amount of the catalyst composition and a minor amount of the one or more reaction by-products contained in the glycolic acid hydrogenation effluent;
(B) separating the first raffinate phase and the first extract phase; and
(C) recovering the catalyst composition from the first extract phase of step (B) by:
  (i) extracting the first extract phase of step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase of step (B) and a second raffinate phase comprising a minor amount of the catalyst composition contained in the first extract phase of step (B); or
  (ii) distilling the first extract phase of step (B) to form a distillate comprising a major amount of the hydrophobic solvent contained in the first extract phase of step (B) and a bottoms comprising a major amount of the catalyst composition contained in the first extract phase of step (B).

The process of Embodiment B or Embodiment B with one or more of the intervening features, wherein the glycolic acid hydrogenation effluent comprises about 0.5 to about 30 weight percent ethylene glycol, about 0.5 to about 30 weight percent water, and about 40 to about 99 weight percent of the one or more reaction by-products; or about 0.5 to about 20 weight percent ethylene glycol, about 0.5 to about 20 weight percent water, and about 70 to about 99 weight percent of the one or more reaction by-products The process of Embodiment B or Embodiment B with one or more of the intervening features, wherein the feed comprises about 10 to about 85 weight percent water based on the total weight of the glycolic acid hydrogenation effluent and the additional water.

The process of Embodiment B or Embodiment B with one or more of the intervening features, wherein the tridentate ligand comprises 1,1,1-tris(diphenylphosphinomethyl)methane, 1,1,1-tris(diphenylphosphinomethyl)ethane, (2-(butoxymethyl)-2-((diphenylphosphino)methyl)propane-1,3-diyl)bis(diphenylphosphine), (2-(benzyloxymethyl)-2-((diphenylphosphino)methyl)propane-1,3-diyl)bis(diphenylphosphine), 1,1,1-tris(diphenylphosphinomethyl)propane, 1,1,1-tris(diphenylphosphinomethyl)butane, 1,1,1-tris(diphenylphosphinomethyl)-2,2-dimethylpropane, 1,1,1-tris(diphenylphosphinomethyl)cyclohexane, 1,1,1-tris(dicyclohexylphosphinomethyl)ethane, 1,1,1-tris(dimethylphosphinomethyl)ethane, 1,1,1-tris(diethylphosphinomethyl)ethane, or mixtures thereof.

The process of Embodiment B or Embodiment B with one or more of the intervening features, wherein the tridentate ligand comprises 1,1,1-tris(diphenylphosphinomethyl)ethane.

The process of Embodiment B or Embodiment B with one or more of the intervening features, wherein the hydrophobic solvent is selected from 2-ethylhexanol, butanol, pentanol, hexanol, heptanol, octanol, nonanol, decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof.

The process of Embodiment B or Embodiment B with one or more of the intervening features, wherein the hydrophobic solvent further comprises a hydrocarbon having from 5 to 20 carbon atoms.

The process of Embodiment B or Embodiment B with one or more of the intervening features, wherein the hydrophobic solvent further comprises a hydrocarbon having from 5 to 20 carbon atoms selected from hexane, heptane, octane, decane, benzene, toluene, xylenes, methyl napththalenes, isoparaffinic mixed hydrocarbons having a boiling range between 90 and 325° C., and mixtures thereof.

The process of Embodiment B or Embodiment B with one or more of the intervening features, wherein the first extractant comprises a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having from 2 to 6 carbon atoms, acetic acid, formic acid, α-hydroxy carboxylic acids having from 4 to 6 carbon atoms, glycolic acid oligomers having from 2 to 6 repeat units, polyol and diol esters of glycolic acid, and mixtures thereof.

The process of Embodiment B or Embodiment B with one or more of the intervening features, wherein the catalyst composition is recovered by extracting the first extract phase of step (B), and wherein the second extractant comprises mono- and diglycolate esters of ethylene glycol.

The process of Embodiment B or Embodiment B with one or more of the intervening features, wherein the tridentate ligand comprises 1,1,1-tris(diphenylphosphinomethyl)ethane and the hydrophobic solvent comprises pentanol and heptane, and wherein the catalyst composition is recovered by distilling the first extract phase of step (B).

The process of Embodiment B or Embodiment B with one or more of the intervening features, further comprising passing the second extract phase or the bottoms of step (C) to a process for the preparation of ethylene glycol by hydrogenation of glycolic acid, glycolate esters, glycolic acid oligomers, or mixtures thereof to ethylene glycol.

The process of Embodiment B or Embodiment B with one or more of the intervening features, further comprising combining the second raffinate phase of step (C) with the first extractant of step (A), distilling the second raffinate phase of step (C) to produce a hydrophobic solvent distillate and combining the hydrophobic solvent distillate with the first extractant of step (A), or combining the distillate of step (C) with the first extractant of step (A).

The process of Embodiment B or Embodiment B with one or more of the intervening features, wherein the catalyst composition is recovered by extracting the first extract phase of step (B), and wherein step (A) and/or step (C) are carried out by fractional countercurrent extraction The process of Embodiment B or Embodiment B with one or more of the intervening features, wherein the first extractant comprises about 60 to 100 weight percent 2-ethylhexanol, butanol, pentanol isobutyl isobutyrate, undecanone, methylisobutyl ketone, diisopropyl ether, or mixtures thereof, and 0 to about 40 weight percent of a hydrocarbon having from 5 to 20 carbon atoms, each based on the total weight of the first extractant.

The process of Embodiment B or Embodiment B with one or more of the intervening features, wherein the hydrophobic solvent comprises pentanol and heptane, and the recovering of the catalyst composition is by distillation, and further comprising passing the bottoms to a process for the preparation of ethylene glycol by hydrogenation of glycolic acid, glycolate esters, glycolic acid oligomers, or mixtures thereof to ethylene glycol.

The invention is further illustrated by the following examples.

EXAMPLES

General—Analyses of glycolic acid hydrogenation products, feeds for extraction, and various extraction phases were carried out by gas chromatography ("GC") using the following procedure. The components from the glycolic acid hydrogenation reaction were first reacted with BSTFA [N,O-bis(trimethylsilyl)trifluoroacetamide] in the presence of pyridine to the corresponding TMS-derivatives including water, which were then separated and quantified by an internal standard (decane) wt % calibrated GC method. The sample to derivatization reagent (BSTFA and pyridine) ratio was 0.1 g:1 ml:0.2 ml in a GC vial, which was heated at 80° C. for 30 minutes to ensure complete derivatization. The GC method used a DB-1301 capillary column or equivalent (6% cyanopropylphenyl/94% dimethylpolysiloxane stationary phase, 60 meters×0.32 mm ID×1.0 um film thickness), a split injector (280° C.), a flame ionization detector (300° C.), helium carrier gas at a constant linear velocity of 27 cm/sec (a Shimadzu GC 2010 or equivalent) or at an initial column head pressure of 17 psi, an oven temperature program of 80° C. initial temp for 6 min, 4° C./min temp ramp rate to 150° C. for 0 min and 10° C./min temp ramp rate to 290° C. for 17.5 min final hold time. A 1-ul aliquot of the prepared sample solution was injected with a split ratio of 40:1. The method provided quantification range of 0.01-100 wt % for each analyte within its separation capability.

Reactor effluent samples were analyzed for ruthenium and phosphorus levels using one of two methods, X-Ray or ICP.

The first method uses a wavelength dispersive x-ray fluorescence (WDXRF) semi-quantitative application called UNIQUANT™ (UQ). UQ affords standardless XRF analysis of samples. The data were mathematically corrected for matrix differences between calibration standards and samples as well as absorption and enhancement effects; i.e. inter-element effects. Instrument conditions for Ru analysis were: Line, $L_\alpha$; kV, 60; mA, 50; Filter, none; Collimator Spacing (mm), 700; Crystal, Ge III-C; Peak Angle (2q), 95.7818 (+offset, 1.6678); Detector, flow; PHD Lower, 32; PHD Upper, 73; Collimator Mask (mm), 37; Peak time (s), 164 (+offset Time (s), 68). Instrument conditions for P analysis were: Line, $K_\alpha$; kV, 60; mA, 50; Filter, none; Collimator Spacing (mm), 700; Crystal, Ge IIII-C; Peak Angle (2q), 133.2764 (+offset, 1.7556); Detector, flow; PHD Lower, 30; PHD Upper, 69; Collimator Mask (mm), 30; Peak time (s), 40 (+offset Time (s), 10).

The second method used detecting Ru and phosphorus was inductively coupled plasma-optical emission spectroscopy (ICP-OES). Approximately 0.5 grams of a sample was weighed into a glass vial. For an internal standard, 0.1 mL of 1000 µg/mL scandium solution was added using a micropipette. The sample was diluted to a volume of 10 mL in a solution of 90 weight percent DMF, 5 weight percent water, and 5 weight percent hydrochloric acid. The sample solution was mixed well and transferred to a centrifuge tube for loading into the autosampler. Analysis was run on a Thermo iCAP 6500 ICP-OES. The instrument was calibrated using certified standards both for calibration and internal standardization. The fluorescent intensity for Ru was measured at 240.272 nm and Sc (361.383 nm) was chosen as the internal standard.

Recovery of a species in extraction is the amount of the species in the extract phase divided by the amount of species in the feed, times 100.

For all extraction examples the partition coefficient for component A is defined as follows:

$$P(A) = \frac{\text{Weight Percent } A \text{ in Hydrophobic phase}}{\text{Weight Percent } A \text{ in Hydrophilic } (EG\text{-rich}) \text{ Phase}}$$

Selectivity between components A and B is defined as:

$$S(AB)=P(A)/P(B)$$

Throughout the examples, the following abbreviations are used in the Tables:

| Compound | Abbreviation |
|---|---|
| 1,1,1-tris(diphenylphosphinomethyl)ethane (Structure II) | Triphos |
| (2-(butoxymethyl)-2-((diphenylphosphino)methyl)propane-1,3-diyl)-bis(diphenylphosphine) (Structure (IV)) | BuO-triphos |
| 1,1,1-tris(diethylphosphinomethyl)ethane (Structure III) | Ethyl-triphos |
| Glycolic Acid | GA |
| Ethylene glycol | EG |
| 1,2-Butanediol | BDO |
| 1,2-Propanediol | PDO |
| 2-Ethylhexanol | 2-EH |
| Ethyl Acetate | EA |
| Isobutyl isobutyrate | IBIB |
| Methyl isobutyl ketone | MIBK |
| Methyl propyl ketone | MPK |
| Diisopropyl ether | DIPE |
| 1-Hexanol | Hexanol |
| 1-Pentanol | Pentanol |
| 1-Butanol | Butanol |

Hydrogenation reactor effluents, F-1 through F-7, were prepared as follows. Generally F-1 through F-3 were prepared in once-through autoclave equipment, and F-4 through F-7 were prepared on pilot-plant scale equipment. Either glycolic acid or a mixture of glyolic acid and glycolate esters was hydrogenated. In the preparation of F-1 through F-4 the ruthenium phosphine catalyst complex was added to the reactor. In the preparation of F-5 through F-7, ruthenium was added to the process as Ruthenium(III) acetylacetonate and phosphorus was added to the process as 1,1,1-tris(diphenylphosphinomethyl)ethane such that the Triphos-Ru catalyst was produced in situ. One skilled in the art recognizes that these catalyst preparation procedures are both commonly used and can be used interchangeably (i.e., no difference in catalyst performance would be expected based on whether the catalyst was prepared in situ). The phosphine ligands for F2-F4 were purchased and the Ru complex made by standard means. The phosphine ligand for the BuO-triphos-Ru catalyst used to make Feed 1 was made using a procedure which follows the reaction steps given in the description and is given below.

BuO-triphos-Ru Catalyst preparation: Step 1—Preparation of (2-(butoxymethyl)-2-((diphenylphosphino)methyl)propane-1,3-diyl)bis(diphenylphosphine) (IV)—Synthesis of pentaerythrityl trichlorohydrin (IX)— A five liter three neck round-bottom flask equipped with an overheard stirrer, a condenser (with a nitrogen purge and a Vigreux column to scrub off any sulfur dioxide), a "Y" connector, with a thermocouple in one side and an addition funnel in the other, was charged with 417 g (3.00 mol) of pentaerythritol and 730 g (9.24 mol) of pyridine. With vigorous stirring, 1134 g (9.24 mol) of thionyl chloride was charged dropwise over a period of 3 hours and 45 minutes and the mixture was heated to 125° C. and held at 125° C. overnight. The brown-yellow solution was cooled to room temperature and 2 L of cold, deionized water was charged with stirring. The precipitate was filtered and washed with 2.5 L of cold, deionized water. The vacuum-dried crude product, (459.7 g), a 1:3.1 mixture of pentaerythrityl trichlorohydrin (VIII) and pentaerythrityltetrachloride (IX) as determined by NMR, was separated using fractional distillation under reduced pressure and recrystallized from cyclohexane to yield 253.5 g of (8). $^1$-H NMR of 8 (CDCl$^3$): δ 3.74 (s, 3H); 3.66 (s, 6H); 1.72 (br, 1H). $^{13}$C{1H} NMR of 8 (CDCl$^3$): δ 61.2, 46.7, 44.0 ppm.

Step 2—Synthesis of 1-(3-Chloro-2,2-bis(chloromethyl)propoxy)butane (X). A 300 mL four neck round-bottom flask equipped with an overheard stirrer, a condenser (with a nitrogen purge) and a thermocouple was charged with 10 g (0.050 mol) of (VIII), 21.68 g (0.16 mol) of 1-bromobutane and 52.50 mL of anhydrous DMSO. The flask was cooled in an ice/water bath and 12.72 g (0.21 mol) of finely ground KOH was charged with vigorous stirring. When no further exotherm was observed, the reaction mixture was heated to 60° C. for 3 hours with stirring. After cooling to room temperature, 225 mL of deionized water was charged slowly. The aqueous phase was extracted with dichloromethane (50 mL) four times. The combined organic layers were washed with 250 mL of 2M HCl, 2×150 mL of deionized water and then dried over Na$_2$SO$_4$. After filtration, the solvent was removed using a rotary evaporator. Product (X) was obtained as a faint yellow liquid. Yield: 11.20 g (0.042 mol, 80%). $^1$H NMR (CDCl$_3$): δ 3.65 (s, 6H); 3.46 (s, 2H); 3.44 (t, 2H); 1.56 (m, 2H); 1.36 (m, 2H); 0.92 (m, 3H). $^{13}$C{1H} NMR (CDCl$_3$): δ 71.4, 68.0, 46.2, 44.5, 31.6, 19.3, 13.8 ppm.

Step 3—Synthesis of (2-(butoxymethyl)-2-((diphenylphosphino)methyl)propane-1,3-diyl)bis(diphenylphosphine) (IV)—A 500 mL three neck round-bottom flask containing 283 g (0.30 mol) of a diethoxymethane (DEM) solution of lithium diphenylphosphide was cooled to −78° C. using a dry ice/acetone bath. To this solution, 23.75 g (0.10 mol) of compound (X) was charged over a period of 30 minutes with an Argon purge. After all of compound (X) was charged, the acetone/dry ice bath was removed, the mixture was allowed to warm to room temperature, and stirred overnight. All volatiles were removed under vacuum, and the residue was extracted with 50 mL of toluene two times. The extract was washed with 50 mL of deionized water three times. The organic phase was dried over $Na_2SO_4$, filtered, and the volatiles were removed under vacuum. 49.5 g (about 74% crude yield and 92% purity) of sticky solid was obtained after drying overnight under vacuum. $^{31}P\{1H\}$ NMR ($CDCl_3$): δ −26.3 ppm (s). $^1H$ NMR ($CDCl_3$): δ 7.50-7.34 (m, 30H); 3.29 (s, 2H); 2.85 (t, 2H); 2.71 (s, 6H); 1.24 m (5H); 0.90 (t, 3H). $^{13}C\{1H\}$ NMR ($CDCl_3$): δ 139.9 (d), 132.9 (d), 128.0 (s), 76.1 (q), 70.3 (s), 42.5 (q), 38.2 (m), 31.4 (s), 19.2 (s), 14.0 (s) ppm.

Preparation of glycolic acid/ester feed and extractant mixture—(referred to henceforth as, "glycolic acid/ester feed" or "glycolic acid/ester extractant"). Several batches of glycolic acid/ester feed were prepared and used in the examples that follow. The ratio of the molar equivalent of EG to glycolic acid was maintained between 1 equivalent of EG to 2 equivalents of glycolic acid and 1.1 equivalents of EG to 2 equivalents of glycolic acid. An example preparation and typical composition are described. A mixture of glycolic acid and glycolate esters was prepared by heating a mixture of 4000 g of glycolic acid and 1795 grams of ethylene glycol at a temperature of about 100 to about 150° C. under atmospheric pressure while removing the water with a Dean-Stark trap. After approximately 860 g of water were removed, the reaction pressure was lowered to 25 torr and the reaction was continued until a total of 947 g of water were collected. Mixtures of glycolic acid and glycolate esters prepared according to this procedure typically contained about 2 wt % ethylene glycol, about 4 wt % glycolic acid, about 2 wt % glycolic acid dimer, about 32 wt % glycolic acid monoesters of ethylene glycol (about 23 wt % glycolic acid monomer ester of EG, about 8 wt % glycolic acid dimer monoester of EG, and about 2 wt % glycolic acid trimer monoester of EG), and about 60 wt % bis-glycolate esters of EG (about 19 wt % glycolic acid monomer diester of EG, about 11 wt % glycolic acid dimer/glycolic acid monomer diester of EG, about 4 wt % glycolic acid trimer/glycolic acid monomer diester of EG, and about 30 wt % higher glycolic acid oligomer diesters of EG). Because the higher molecular weight glycolic acid oligomer diesters could not be detected by the gas chromatographic method described above, the weight percentages shown for these compounds were estimated by subtracting the total weight percentages of the components detected by GC from 100 wt %. The glycolic acid and ester mixtures prepared by this procedure were used as the glycolic acid/ester feed for glycolic acid hydrogenation reaction which produced F-1 through F-5 and as the glycolic acid/ester extractant for back-extracting the ruthenium catalyst compositions from the various hydrophobic extracts in examples set forth below.

Feed 1: Hydrogenation of Glycolic Acid and Glycolate Esters—A mixture comprising 70 ml ethylene glycol, and 6 mL of the glycolic acid/ester feed, 5 weight percent water, and (2-(butoxymethyl)-2-((diphenylphosphino)methyl)propane-1,3-diyl)bis(diphenylphosphine) ruthenium diacetate (referred to herein as "BuO-triphos-Ru catalyst;" ligand IV) at a concentration of 100 ppm Ru metal was loaded into a high pressure Hastelloy C autoclave. The autoclave, nominally 100 mL volume, was fitted with a Rushton turbine impeller, baffles, thermowell, and gas inlet tube. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 124.1 bars gauge (1800 psig). After the initial charge, a stock solution of the glycolic acid/ester feed containing 5 weight percent water and BuO-triphos-Ru catalyst at a concentration of 100 ppm Ru metal was fed for five hours at a rate of 0.4 mL/min. After five hours, the feed rate was cut to 0.197 mL/min (feed substrate rate of 0.192 ml/min, and the catalyst rate of 0.005 mL/min). Aliquots of reactor material were taken off every five minutes to maintain the liquid level at approximately 71-72.5 mL. The cumulative reactor effluent, F-1, composition is given in Table 1.

Feed 2: Hydrogenation of Glycolic Acid and Glycolate Esters—A mixture containing the glycolic acid/ester feed, water, and $(triphos)Ru(OAc)_2$ (referred to as "Triphos-Ru catalyst;" ligand II) at a concentration of 115 ppm Ru metal was fed continuously at a rate of 0.4 mL/min to a high pressure Hastelloy C autoclave. The ratio of glycolic acid/ester feed to water was adjusted to achieve 7.5 weight percent to 10 weight percent water in the reactor feed. The autoclave, nominally 100 mL volume, was fitted with a hollow shaft Rushton turbine impeller (for gas introduction and dispersion), baffles, thermowell, gas inlet tube, and sip tube to maintain liquid level at approximately 71 mL and to provide an exit for product effluent. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 168.9 bars gauge (2450 psig). The reactor effluent was collected in a Hastelloy vessel. Conditions were maintained for at least 24 hours to establish steady state operation. The reactor effluent, F-2, composition is given in Table 1.

Feed 3: Hydrogenation of Glycolic Acid and Esters—A mixture containing the glycolic acid/ester feed, water, and $(ethyl-triphos)Ru(OAc)_2$, the catalyst with ligand III, at a concentration of about 270 ppm Ru metal was fed continuously at a rate of 0.4 mL/min to a high pressure Hastelloy C autoclave. The ratio of EG diglycolate esters to water was adjusted to achieve less than 1 weight percent water in the feed. The autoclave, nominally 100 mL volume, was fitted with a hollow shaft Rushton turbine impeller (for gas introduction and dispersion), baffles, thermowell, gas inlet tube, and sip tube to maintain liquid level at approximately 71 mL and to provide an exit for product effluent. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 168.9 bars gauge (2450 psig). The reactor effluent was collected in a Hastelloy vessel. Conditions were maintained for at least 24 hours to ensure steady state operation. The reactor effluent, F-3, composition is given in Table 1.

Feed 4: Hydrogenation of Glycolic Acid and Esters—The reactor effluent of Feed 4 was produced in a pilot plant by hydrogenating the glycolic acid/ester feed. A concentration step, located downstream of the hydrogenation reactor, separated out part of the EG and water from the glycolic acid hydrogenation product to thereby create a glycolic acid hydrogenation effluent comprising reaction by-products, catalyst, and the remaining EG and water. Most of the concentrated glycolic acid hydrogenation effluent was recycled back to the reactor. F-4 was a purge stream off the concentrated glycolic acid hydrogenation effluent. The composition of F-4 is given in Table 1. F-4 was made in a different pilot plant than the one used to make F-5 through F-7.

Feed 5: Hydrogenation of Glycolic Acid and Esters—The reactor effluent of Feed 5 was produced in a pilot plant by hydrogenating the glycolic acid/ester feed (89 weight percent) and water (11 weight percent). The reactor was initially charged with the catalyst and substrate. The reactor was pressurized to 1000 psig with hydrogen and allowed to react; the pressure decreased to 800 psig; the reactor was pressurized back to 1000 psig. The reaction temperature was 190° C. After pressure cycled 11 times, the pressure was reduced to 100 psig and material was stripped from the reactor. The reactor was recharged with feed (no additional catalyst) and the process was repeated a second time. F-5 was the remaining liquid in the reactor. The composition of F-5 is given in Table 1.

Feed 6: Hydrogenation of Glycolic Acid—The reactor effluent of Feed 6 was produced in a pilot plant by hydrogenating a 67 wt % glycolic acid in water feed. The catalyst was charged to the reactor. The glycolic acid and hydrogen feed were fed continuously while ethylene glycol and water were continuously removed from the reactor (i.e., flashed from the reactor) at a reactor temperature of 220° C. and pressure of 800 psig. The reaction was run for 200 hours. F-6 was the liquid remaining in the reactor. The composition of F-6 is given in Table 1.

Feed 7: Hydrogenation of Glycolic Acid—The reactor effluent of Feed 7 was produced in a pilot plant by hydrogenating a 67 wt % glycolic acid in water feed. The reactor was initially charged with the catalyst and substrate. The reactor was pressurized to 1000 psig with hydrogen and allowed to react; the pressure decreased to 800 psig; the reactor was pressurized back to 1000 psig. The reactor temperature was 190° C. After pressure cycled 10 times, the pressure was reduced to 100 psig and material was stripped from the reactor. The reactor was recharged with feed (no additional catalyst) and the process was repeated a second time. F-7 was the remaining liquid in the reactor. The composition of F-7 is given in Table 1.

A summary of the feed compositions is given in Table 1. Note the feeds were often diluted with water in the Examples before being subject to extraction. Table 1 lists the undiluted feed composition.

TABLE 1

Undiluted Feed Compositions

| | | Feed | | | | | | |
|---|---|---|---|---|---|---|---|---|
| | | F-1 | F-2 | F-3 | F-4 | F-5 | F-6 | F-7 |
| | Ligand | IV | II | III | II | II | II | II |
| | Ru (ppm) | 27.9 | 111.0 | 260.5 | 526.0 | 75.8 | 93.6 | 162.0 |
| | Ph (ppm) | 23.5 | 111.0 | | 486.0 | 90.0 | 151.0 | 149.0 |
| GC Results, wt % | H2O | 4.51 | 9.43 | 0.70 | 9.90 | 3.17 | 11.10 | 30.26 |
| | EG | 85.23 | 85.71 | 99.30 | 59.27 | 6.68 | 17.22 | 19.14 |
| | DEG | 0.35 | 0.11 | | 0.16 | 1.39 | 5.12 | 1.22 |
| | TEG | | | | | 0.21 | 2.13 | 0.07 |
| | G1 | 0.27 | 0.39 | | 4.11 | 9.37 | 5.05 | 24.54 |
| | G2 | 0.01 | 0.03 | | 0.07 | 1.88 | 0.38 | 0.82 |
| | G3 | | | | | 0.23 | 0.71 | 0.01 |
| | HGEgH | 3.39 | 1.77 | | 23.45 | 28.98 | 33.15 | 17.50 |
| | HGEg2H | 0.02 | | | 0.03 | 3.51 | 5.50 | 0.61 |
| | HGEgG'H | 0.24 | 0.19 | | 0.49 | 8.85 | 4.55 | 0.91 |
| | HG2EgH | 0.26 | 0.21 | | 0.59 | 5.28 | 2.76 | 0.43 |
| | HGEg2G'H | | | | | 2.00 | 1.67 | 0.08 |
| | HG2EgG'H | 0.10 | 0.09 | | 0.02 | 2.98 | 0.66 | 0.04 |
| | Other Knowns | 0.61 | 0.23 | | 0.11 | 3.31 | 1.02 | 1.37 |
| | Unknowns | 1.10 | 1.59 | | 0.13 | 5.99 | 5.68 | 2.38 |
| | Total | 96.08 | 99.75 | | 98.34 | 83.85 | 96.69 | 99.38 |

For Table 1 - G1 is glycolic acid, G2, 3, 4, are G1'smers, HGEgH is an ester of G1 and EG, HGEGG'H is an ester of G1, EG, and Glycolate Example 1

This example illustrates the effect of different hydrophobic solvent compositions on the forward and back extraction of the ruthenium catalyst complexes and ethylene glycol. In Experiments 1-1 to 1-11, water was added to Feed 2 (F-2) to give a water content of 30 weight percent. The resulting mixtures were contacted with a hydrophobic solvent mixture in the composition and S/F ratio specified in Table 2A. Each mixture was held at 60° C., allowed to separate into two clear phases. An identical procedure was repeated for Experiments 1-12 to 1-22, using Feed 1 (F-1). The resulting partition coefficients and selectivities are summarized in Table 2A.

An identical procedure was repeated for Experiment 1-23, except using Feed 4 (F-4), diluted to comprise 37 weight percent water. The resulting partition coefficients and selectivities are summarized in Table 2A.

A portion of the top phase, the extract, of each extraction Experiment 1-1 to 1-22, Experiments 1-24 to 1-45, respectively, was next contacted with the glycolic acid/ester extractant at the solvent-feed (S/F) ratio specified in Table 2B. The extract from Experiment 1-23 was split into two portions. Part of one portion was contacted with the glycolic and/ester extractant, Experiment 1-46. Heptane was added to the other portion such that the composition was 30 wt % heptane and the resulting mixture was contacted with the glycolic and/ester extractant, Experiment 1-47. Each mixture was held at 60° C., allowed to separate into two clear phases. The resulting partition coefficients are summarized in Table 2B.

TABLE 2A

Extraction of Glycolic Acid Hydrogenation Effluent

| Ex. | Solvent 1 (wt %) | Solvent 2 (wt %) | Ligand | S/F Ratio | P(Ru) | P(EG) | Select. Ru/EG |
|---|---|---|---|---|---|---|---|
| *F-2 diluted to 30 wt % water* | | | | | | | |
| 1-1 | 2-Ethylhexanol (100%) | | II | 1.00 | 2.80 | 0.16 | 17.5 |
| 1-2 | IBIB (100%) | | II | 1.00 | 0.14 | 0.01 | 13.8 |
| 1-3 | Undecanones (100%) | | II | 1.00 | 0.08 | 0.01 | 8.2 |
| 1-4 | MIBK (100%) | | II | 1.00 | 0.18 | 0.06 | 3.1 |
| 1-5 | DIPE (100%) | | II | 1.00 | 0.02 | 0.00 | 8.3 |
| 1-6 | Heptane (100%) | | II | 1.00 | 0.03 | 0.00 | ∞ |
| 1-7 | 2-Ethylhexanol (90%) | Heptane (10%) | II | 1.00 | 2.01 | 0.13 | 15.5 |
| 1-8 | IBIB (90%) | Heptane (10%) | II | 1.00 | 0.16 | 0.01 | 28.9 |
| 1-9 | Undecanones (89%) | Heptane (11%) | II | 1.01 | 0.10 | 0.01 | 14.6 |
| 1-10 | MIBK (90%) | Heptane (10%) | II | 1.00 | 0.14 | 0.02 | 5.7 |
| 1-11 | DIPE (90%) | Heptane (10%) | II | 1.01 | 0.04 | 0.00 | 17.1 |
| *F-1 diluted to 30 wt % water* | | | | | | | |
| 1-12 | 2-Ethylhexanol (100%) | | IV | 1.00 | 8.17 | 0.16 | 51.1 |
| 1-13 | IBIB (100%) | | IV | 1.00 | 0.09 | 0.01 | 11.4 |
| 1-14 | Undecanones (100%) | | IV | 1.00 | 1.79 | 0.01 | 189.1 |
| 1-15 | MIBK (100%) | | IV | 1.00 | 0.13 | 0.04 | 3.2 |
| 1-16 | DIPE (100%) | | IV | 1.00 | 0.07 | 0.00 | 22.2 |
| 1-17 | Heptane (100%) | | IV | 1.00 | 0.04 | 0.00 | ∞ |
| 1-18 | 2-Ethylhexanol (90%) | Heptane (10%) | IV | 1.00 | 9.86 | 0.12 | 82.2 |
| 1-19 | IBIB (90%) | Heptane (10%) | IV | 1.01 | 0.19 | 0.01 | 21.0 |
| 1-20 | Undecanones (91%) | Heptane (9%) | IV | 1.09 | 0.49 | 0.01 | 61.8 |
| 1-21 | MIBK (90%) | Heptane (10%) | IV | 1.00 | 0.32 | 0.02 | 15.1 |
| 1-22 | DIPE (90%) | Heptane (10%) | IV | 1.00 | 0.10 | 0.00 | 43.0 |
| *F-4 diluted to 37 wt % water* | | | | | | | |
| 1-23 | 2-Ethylhexanol (100%) | | II | 1.00 | 1.27 | 0.15 | 8.48 |

TABLE 2B

Recovery of Catalyst from First Extract with Glycolic Acid/Ester Extractant

| Ex. | Solvent 1 (wt %) | Solvent 2 (wt %) | Ligand Structure | S/F Ratio | P (Ru) |
|---|---|---|---|---|---|
| *First Extract from F-2 diluted to 30 wt % water extraction* | | | | | |
| 1-24 | 2-Ethylhexanol (100%) | | II | 1.00 | 0.41 |
| 1-25 | IBIB (100%) | | II | 1.00 | 1.22 |
| 1-26 | Undecanones (100%) | | II | 1.00 | 0.21 |
| 1-27 | MIBK (100%) | | II | 1.00 | 0.30 |
| 1-28 | DIPE (100%) | | II | 1.00 | 0.45 |
| 1-29 | Heptane (100%) | | II | 1.00 | 1.30 |
| 1-30 | 2-Ethylhexanol (90%) | Heptane (10%) | II | 1.00 | 0.23 |
| 1-31 | IBIB (90%) | Heptane (10%) | II | 1.00 | 1.24 |
| 1-32 | Undecanones (89%) | Heptane (11%) | II | 1.00 | 0.44 |
| 1-33 | MIBK (90%) | Heptane (10%) | II | 1.00 | 0.86 |
| 1-34 | DIPE (90%) | Heptane (10%) | II | 1.00 | 0.55 |
| *First extract from F-1 diluted to 30 wt % water extraction* | | | | | |
| 1-35 | 2-Ethylhexanol (100%) | | IV | 1.00 | 3.03 |
| 1-36 | IBIB (100%) | | IV | 1.00 | 0.66 |
| 1-37 | Undecanones (100%) | | IV | 1.00 | one phase |
| 1-38 | MIBK (100%) | | IV | 1.00 | 0.14 |
| 1-39 | DIPE (100%) | | IV | 1.00 | 6.94 |
| 1-40 | Heptane (100%) | | IV | 1.00 | 0.00 |
| 1-41 | 2-Ethylhexanol (90%) | Heptane (10%) | IV | 1.00 | 1.12 |
| 1-42 | IBIB (90%) | Heptane (10%) | IV | 1.01 | 0.75 |
| 1-43 | Undecanones (91%) | Heptane (9%) | IV | 1.00 | 1.90 |
| 1-44 | MIBK (90%) | Heptane (10%) | IV | 1.01 | 0.18 |
| 1-45 | DIPE (90%) | Heptane (10%) | IV | 1.00 | 9.57 |
| *First extract from F-4 diluted to 37 wt % water extraction* | | | | | |
| 1-46 | 2-Ethylhexanol | | II | 1.00 | 0.42 |
| 1-47 | 2-Ethylhexanol | Heptane (30%) | II | 1.00 | 7.06 |

Example 2

This example illustrates the effect of water content in the glycolic acid hydrogenation effluent feed mix and the effect of hydrocarbon content of the extractant on extraction of the BuO-triphos-Ru catalyst, ethylene glycol, 1,2-butanediol (BDO), and 1,2-propanediol (PDO). In Experiments 2-1 to 2-20, water was added to Feed 1 (F-1) to give the water content specified in Table 3. In addition, 1 weight percent (on an undiluted reactor effluent basis) each of BDO and PDO was added to Feed 1 (F-1). The resulting mixtures were contacted with a solvent mixture comprising 2-ethylhexanol and heptane in the composition and S/F ratio specified in Table 3. Each mixture was held at 60° C., allowed to separate into two clear phases. The ruthenium, phosphine, ethylene glycol, 1,2-propanediol, and 1,2-butanediol partition coefficients (abbreviated as P(Ru), P(Phos), P(EG), P(PDO), and P(BDO)) are summarized in Table 3.

TABLE 3

Extraction of F-1 with 2-EH and Heptane

| Ex. | S/F Ratio | Wt % Water in Feed Mix | Wt % Heptane in Solvent Mix | P(Ru) | P(Phos) | P(EG) | P(PDO) | P(BDO) |
|---|---|---|---|---|---|---|---|---|
| 2-1 | 0.99 | 9.89% | 0.0% | 3.24 | 4.16 | 0.46 | 0.63 | 0.87 |
| 2-2 | 1.00 | 14.00% | 0.0% | 2.40 | 6.41 | 0.31 | 0.50 | 0.79 |
| 2-3 | 0.99 | 23.71% | 0.0% | 5.51 | 8.46 | 0.21 | 0.37 | 0.68 |
| 2-4 | 1.00 | 33.25% | 0.0% | 8.17 | 48.73 | 0.16 | 0.31 | 0.63 |
| 2-5 | 1.00 | 9.89% | 10.0% | 2.05 | 2.31 | 0.32 | 0.48 | 0.72 |
| 2-6 | 0.99 | 14.00% | 10.0% | 2.01 | 2.40 | 0.23 | 0.39 | 0.65 |
| 2-7 | 1.01 | 23.71% | 10.0% | 3.30 | 6.55 | 0.16 | 0.31 | 0.58 |
| 2-8 | 1.00 | 33.25% | 10.0% | 9.86 | 12.78 | 0.12 | 0.25 | 0.53 |
| 2-9 | 1.00 | 9.89% | 15.1% | 1.45 | 1.75 | 0.26 | 0.41 | 0.64 |
| 2-10 | 1.01 | 14.00% | 15.1% | 1.96 | 2.44 | 0.20 | 0.35 | 0.58 |
| 2-11 | 1.00 | 23.71% | 15.1% | 3.71 | 5.06 | 0.14 | 0.27 | 0.53 |
| 2-12 | 1.00 | 33.25% | 15.1% | 4.93 | 21.89 | 0.11 | 0.23 | 0.48 |
| 2-13 | 1.00 | 9.89% | 20.0% | 1.26 | 1.21 | 0.22 | 0.36 | 0.58 |
| 2-14 | 0.99 | 14.00% | 20.0% | 1.64 | 1.92 | 0.18 | 0.31 | 0.54 |
| 2-15 | 1.01 | 23.71% | 20.0% | 3.70 | 6.10 | 0.13 | 0.25 | 0.49 |
| 2-16 | 0.99 | 33.25% | 20.0% | 5.15 | 11.07 | 0.10 | 0.21 | 0.45 |
| 2-17 | 0.99 | 9.89% | 30.0% | 0.87 | 1.07 | 0.16 | 0.27 | 0.45 |
| 2-18 | 1.00 | 14.00% | 30.0% | 1.10 | 1.57 | 0.14 | 0.25 | 0.45 |
| 2-19 | 1.00 | 23.71% | 30.0% | 3.74 | 3.26 | 0.10 | 0.20 | 0.39 |
| 2-20 | 1.00 | 33.25% | 30.0% | 3.82 | 14.56 | 0.08 | 0.17 | 0.37 |

Example 3

This example illustrates the effect of water content in the glycolic acid hydrogenation effluent feed mix and the effect of hydrocarbon content of the extractant on extraction of the Triphos-Ru catalyst, ethylene glycol, 1,2-butanediol (BDO), and 1,2-propanediol (PDO). In Experiments 3-1 to 3-20, water was added to Feed 2 (F-2) to give the water content specified in Table 4A. In addition, 1 weight percent (on an undiluted reactor effluent basis) each of BDO and PDO was added to Feed 2 (F-2). The resulting mixtures were contacted with a solvent mixture comprising 2-ethylhexanol and heptane in the composition and S/F ratio specified in Table 4A.

Each mixture was held at 60° C. and allowed to separate into two clear phases. The ruthenium, phosphine, ethylene glycol, 1,2-propanediol, and 1,2-butanediol partition coefficients (abbreviated as P(Ru), P(Phos), P(EG), P(PDO), and P(BDO)) are summarized in Table 4A.

The above procedure was repeated with Feed 4 (F-4), with the Triphos-Ru catalyst. In Experiments 3-21 to 3-40, water was added to Feed 4 (F-4) to give the water content specified in Table 4A. In addition, 1 weight percent (on an undiluted reactor effluent basis) of PDO was added to F-4. The resulting mixtures were contacted with a solvent mixture comprising 2-ethylhexanol and heptane in the composition and S/F ratio specified in Table 4A.

TABLE 4A

Extraction of F-2 and F-4 with 2-EH and Heptane

| Ex. | S/F Ratio | Wt % Water in Feed Mix | Wt % Heptane in Solvent Mix | P(Ru) | P(Phos) | P(EG) | P(PDO) | P(BDO) |
|---|---|---|---|---|---|---|---|---|
| F-2 | | | | | | | | |
| 3-1 | 0.99 | 9.2% | 0% | 2.19 | 2.02 | 0.56 | 0.72 | 0.93 |
| 3-2 | 1.00 | 13.5% | 0% | 1.44 | 1.51 | 0.34 | 0.50 | 0.79 |
| 3-3 | 1.00 | 22.5% | 0% | 1.87 | 1.91 | 0.21 | 0.36 | 0.68 |
| 3-4 | 1.00 | 30.4% | 0% | 2.80 | 3.23 | 0.16 | 0.30 | 0.64 |
| 3-5 | 1.00 | 9.2% | 10% | 0.87 | 0.81 | 0.32 | 0.47 | 0.71 |
| 3-6 | 1.00 | 13.5% | 10% | 0.99 | 0.94 | 0.25 | 0.41 | 0.68 |
| 3-7 | 1.00 | 22.5% | 10% | 1.29 | 1.45 | 0.17 | 0.31 | 0.60 |
| 3-8 | 1.00 | 30.4% | 10% | 2.01 | 2.13 | 0.13 | 0.25 | 0.55 |
| 3-9 | 1.00 | 9.2% | 15% | 0.67 | 0.70 | 0.25 | 0.39 | 0.62 |
| 3-10 | 1.00 | 13.5% | 15% | 0.79 | 1.49 | 0.20 | 0.34 | 0.57 |
| 3-11 | 1.00 | 22.5% | 15% | 1.12 | 1.13 | 0.15 | 0.26 | 0.54 |
| 3-12 | 1.01 | 30.4% | 15% | 1.87 | 1.82 | 0.11 | 0.22 | 0.49 |
| 3-13 | 0.89 | 9.2% | 20% | 0.58 | 0.59 | 0.22 | 0.35 | 0.58 |
| 3-14 | 1.00 | 13.5% | 20% | 0.69 | 0.69 | 0.19 | 0.32 | 0.56 |
| 3-15 | 1.00 | 22.5% | 20% | 1.02 | 1.03 | 0.13 | 0.23 | 0.47 |
| 3-16 | 1.01 | 30.4% | 20% | 1.59 | 1.70 | 0.10 | 0.20 | 0.43 |
| 3-17 | 1.00 | 9.2% | 30% | 0.38 | 0.41 | 0.16 | 0.27 | 0.45 |
| 3-18 | 1.01 | 13.5% | 30% | 0.49 | 0.49 | 0.13 | 0.24 | 0.44 |
| 3-19 | 1.00 | 22.5% | 30% | 0.75 | 0.77 | 0.10 | 0.19 | 0.39 |
| 3-20 | 1.00 | 30.4% | 30% | 1.21 | 0.64 | 0.08 | 0.16 | 0.36 |

TABLE 4A-continued

Extraction of F-2 and F-4 with 2-EH and Heptane

| Ex. | S/F Ratio | Wt % Water in Feed Mix | Wt % Heptane in Solvent Mix | P(Ru) | P(Phos) | P(EG) | P(PDO) | P(BDO) |
|---|---|---|---|---|---|---|---|---|
| | | | | F-4 | | | | |
| 3-21 | 1.00 | 14.1% | 0% | 0.83 | (1) | 0.25 | 0.45 | (2) |
| 3-22 | 1.00 | 18.7% | 0% | 0.71 | (1) | 0.20 | 0.37 | (2) |
| 3-23 | 1.00 | 27.7% | 0% | 1.05 | (1) | 0.14 | 0.31 | (2) |
| 3-24 | 1.00 | 36.9% | 0% | 1.45 | (1) | 0.12 | 0.28 | (2) |
| 3-25 | 1.00 | 14.1% | 10% | 0.45 | (1) | 0.17 | 0.34 | (2) |
| 3-26 | 1.00 | 18.7% | 10% | 0.50 | (1) | 0.14 | 0.30 | (2) |
| 3-27 | 1.00 | 27.7% | 10% | 0.82 | (1) | 0.12 | 0.27 | (2) |
| 3-28 | 1.00 | 36.9% | 10% | 1.07 | (1) | 0.10 | 0.23 | (2) |
| 3-29 | 1.00 | 14.1% | 15% | 0.37 | (1) | 0.15 | 0.31 | (2) |
| 3-30 | 1.00 | 18.7% | 15% | 0.47 | (1) | 0.13 | 0.28 | (2) |
| 3-31 | 1.00 | 27.7% | 15% | 0.74 | (1) | 0.30 | 0.41 | (2) |
| 3-32 | 1.00 | 36.9% | 15% | 1.00 | (1) | 0.09 | 0.22 | (2) |
| 3-33 | 1.00 | 14.1% | 20% | 0.34 | (1) | 0.28 | 0.41 | (2) |
| 3-34 | 1.00 | 18.7% | 20% | 0.40 | (1) | 0.11 | 0.25 | (2) |
| 3-35 | 1.00 | 27.7% | 20% | 0.60 | (1) | 0.15 | 0.28 | (2) |
| 3-36 | 1.00 | 36.9% | 20% | 0.88 | (1) | 0.08 | 0.20 | (2) |
| 3-37 | 1.00 | 14.1% | 30% | 0.18 | (1) | 0.10 | 0.22 | (2) |
| 3-38 | 1.00 | 18.7% | 30% | 0.25 | (1) | 0.09 | 0.20 | (2) |
| 3-39 | 1.00 | 27.7% | 30% | 0.41 | (1) | 0.07 | 0.18 | (2) |
| 3-40 | 1.00 | 36.9% | 30% | 0.68 | (1) | 0.07 | 0.16 | (2) |

(1) Phosphorus was not measured for these examples.
(2) BDO was not added to the feed mix for these examples.

In Experiments 3-41 to 3-51 water was added to Feed 5 (F-5) to give the water content specified in Table 4B. The resulting mixtures were contacted with various solvents at the S/F ratios specified in Table 4B. Each mixture was held at 60° C. and allowed to separate into two clear phases. The ruthenium, phosphine, ethylene glycol, partition coefficients (abbreviated as P(Ru), P(Phos), and P(EG)) are summarized in Table 4B. An identical procedure was repeated for Experiments 3-52 to 3-60 using Feed 6 (F-6). The resulting partition coefficients and selectivities are summarized in Table 4B.

TABLE 4B

Extraction of F-5 and F-6 with Various Solvents

| Ex. | S/F Ratio | Wt % Water in Feed Mix | Wt % Solvent | P(Ru) | P(Phos) | P(EG) | Select. Ru/EG |
|---|---|---|---|---|---|---|---|
| | | | F-5 | | | | |
| 3-41 | 0.47 | 86.0% | Butanol (100%) | +17 | +9.5 | 0.47 | +36 |
| 3-42 | 1.00 | 71.0% | Ethyl Acetate (100%) | 1.34 | 1.59 | 0.09 | 14.7 |
| 3-43 | 1.00 | 71.0% | MIBK (100%) | 2.57 | 3.33 | 0.04 | 67.3 |
| 3-44 | 1.00 | 71.0% | MPK (100%) | 6.91 | 5.17 | 0.09 | 81.1 |
| 3-45 | 0.99 | 36.4% | 2-EH (100%) | 0.26 | 0.30 | 0.06 | 4.2 |
| 3-46 | 1.00 | 72.3% | 2-EH (100%) | 2.07 | 1.88 | 0.02 | 94.8 |
| 3-47 | 1.00 | 36.4% | Hexanol (100%) | 2.71 | 2.14 | 0.22 | 12.2 |
| 3-48 | 1.00 | 51.6% | Hexanol (100%) | 5.71 | 3.87 | 0.15 | 37.4 |
| 3-49 | 1.00 | 72.3% | Hexanol (100%) | 10.24 | 6.28 | 0.06 | 162.4 |
| 3-50 | 1.00 | 36.4% | Pentanol (100%) | 3.36 | 2.66 | 0.40 | 8.4 |
| 3-51 | 1.00 | 72.3% | Pentanol (100%) | 14.00 | 6.79 | 0.11 | 129.7 |
| | | | F-6 | | | | |
| 3-52 | 1.00 | 36.2% | 2-EH (100%) | 1.50 | 0.58 | 0.15 | 9.9 |
| 3-53 | 1.00 | 53.4% | 2-EH (100%) | 2.47 | 0.76 | 0.09 | 27.4 |
| 3-54 | 1.00 | 72.6% | 2-EH (100%) | 3.91 | 0.93 | 0.06 | 66.0 |
| 3-55 | 1.00 | 36.2% | Hexanol (100%) | 1.88 | 0.66 | 0.41 | 4.5 |
| 3-56 | 1.00 | 53.4% | Hexanol (100%) | 4.75 | 0.86 | 0.24 | 20.2 |
| 3-57 | 1.00 | 72.6% | Hexanol (100%) | 7.00 | 1.07 | 0.16 | 44.8 |
| 3-58 | 1.00 | 53.4% | Pentanol (100%) | 2.71 | 0.62 | 0.45 | 6.0 |
| 3-59 | 1.00 | 72.6% | Pentanol (100%) | 5.26 | 0.88 | 0.30 | 17.3 |
| 3-60 | 1.00 | 70.8% | Pentanol (1) | 7.03 | 1.32 | 0.29 | 24.2 |

(1) Pentanol saturated with water, contained 12.1 wt % water at 60° C.

In Experiments 3-61 to 3-67, water was added to Feed 4 (F-4) to give the water content specified in Table 4C. In addition, 1 weight percent (on an undiluted reactor effluent basis) of PDO was added to F-4. The resulting mixtures were contacted with a solvent mixture comprising 2-ethylhexanol and/or pentanol in the weight percent and S/F ratios specified in Table 4C. Mixtures 3-61 to 3-65 were held at 60° C., while mixtures 3-66 and 3-67 were held at 90° C. The mixtures were allowed to separate into two clear phases. The ruthenium, phosphine, ethylene glycol, and 1,2-propanediol, partition coefficients (abbreviated as P(Ru), P(Phos), P(EG), an P(PDO)) are summarized in Table 4C.

TABLE 4C

Extraction of F-4 with 2-EH and Pentanol

| Ex. | S/F Ratio | Wt % Water in Feed Mix | Wt % 2-EH | Wt % Pentanol | P(Ru) | P(Phos) | P(EG) | P(PDO) | Select. Ru/EG |
|---|---|---|---|---|---|---|---|---|---|
| 3-61 | 1.00 | 26.7% | 100% | 0% | 0.93 | 0.97 | 0.18 | 0.35 | 5.3 |
| 3-62 | 1.00 | 36.9% | 100% | 0% | 1.56 | 1.68 | 0.13 | 0.28 | 12.1 |
| 3-63 | 1.00 | 26.8% | 50% | 50% | 1.80 | 2.03 | 0.45 | 0.67 | 4.0 |
| 3-64 | 1.00 | 36.9% | 50% | 50% | 2.80 | 3.13 | 0.27 | 0.51 | 10.4 |
| 3-65 | 0.55 | 50.0% | 0% | 100% | 6.24 | 7.22 | 0.50 | 0.79 | 12.4 |
| 3-66 | 1.00 | 27.4% | 100% | 0% | 1.84 | 2.10 | 0.22 | 0.41 | 8.2 |
| 3-67 | 1.00 | 36.9% | 100% | 0% | 2.82 | 3.38 | 0.14 | 0.31 | 19.8 |

The hydrophobic solvent system described herein for the extraction of the catalyst-ligand complex from a hydrogenated glycolic acid stream also may be used for the extractive separation of diol hydrogenation by-products from a hydrogenated glycolic acid stream comprising ethylene glycol. As shown by the partition coefficients shown in Tables 3 and 4, the extraction process of the instant invention is useful for separating three- and four-carbon diols, e.g., 1,2-propanediol, and 1,2-butanediol, from ethylene glycol. Because of the lower capacity and selectivity for the extraction of diols, the solvent to feed ratio and/or number of extraction stages must be increased over that required for extraction of the catalyst-ligand complex.

Example 4

This example illustrates extractive recovery of a catalyst from a glycolic acid hydrogenation reaction effluent. Water was added to Feed 1 (F-1), containing BuO-triphos-Ru catalyst, such that the resulting mixture contained about 31 weight percent water. This feed mixture was subjected to cross-flow batch extractions at 60° C. using a solvent comprised of a mixture of 90 weight percent 2-ethylhexanol and 10 weight percent heptane as modifier. In Example 4-1, one extraction was carried out. In Example 4-2, three cross-flow extractions were completed in the following fashion.

The aqueous feed mixture was contacted with the specified solvent mixture at the given solvent to feed ratio, and the resulting aqueous ethylene glycol phase from the first extraction step was contacted with another portion of fresh solvent. This sequence was repeated an additional time for a total of three cross-flow extractions. The feed conditions for each set of extractions, the resulting Ru and P recovery into the extract phase, and the partition coefficient for ethylene glycol are summarized in Table 5.

TABLE 5

Extraction of F-1 with 2-EH and Heptane

| Ex. | Wt % 2-EH Alcohol in Solvent | Wt % Heptane in Solvent | Wt % Water in Feed | T, ° C. | No. Extr. Stages | S/F Ratio per Stage | % Ru Recov | % Phos Recov | P(EG) |
|---|---|---|---|---|---|---|---|---|---|
| 4-1 | 90.0% | 10.0% | 31% | 60 | 1 | 1.00 | 82% | 97% | 9.5 |
| 4-2 | 90.0% | 10.0% | 31% | 60 | 3 | 0.35 | 92% | 100% | 9.0 |

Example 5

This example illustrates back extraction of a BuO-triphos-Ru catalyst from the catalyst-rich extract mixture of Example 4-1 using the glycolic acid/ester extractant. The catalyst-rich extract mixture of Example 4-1, containing 8.6 weight percent heptane in 2-ethylhexanol, was divided into four portions. Additional heptane was added to three of the portions as set forth in Table 6. Each of these portions was subjected to cross-flow batch extractions at 60° C. using the glycolic acid/ester extractant at the solvent to feed ratio and number of cross-flow extractions specified in Table 6. The resulting heptane/2-ethylhexanol phase from the first extraction step was contacted with another portion of fresh glycolic acid/ester extractant. The feed conditions for each set of extractions and the resulting Ru and P recovery into the glycolate acid/ester extract phase are summarized in Table 6.

TABLE 6

Back Extraction of Catalyst-Rich Extract Phase of Example 4-1 (F-1)

| Ex. | Wt % 2-EH in Feed | Wt % Heptane in Feed | T, ° C. | No. of Extraction Stages | S/F Ratio per Stage | % Recov. Ru | % Recov Phos |
|---|---|---|---|---|---|---|---|
| 5-1 | 91.4% | 8.6% | 60 | 2 | 0.71 | 74% | 85% |
| 5-2 | 80.4% | 19.6% | 60 | 2 | 0.71 | 83% | 89% |
| 5-3 | 71.8% | 28.2% | 60 | 2 | 0.72 | 94% | 92% |
| 5-4 | 62.5% | 37.5% | 60 | 2 | 0.71 | 99% | 96% |

Example 6

This example illustrates extractive recovery of a Triphos-Ru catalyst from a glycolic acid hydrogenation reaction effluent. Water was added to Feed 2 (F-2) to give a feed mixture containing about 30 weight percent water. This feed mixture was subjected to cross-flow batch extractions at 60° C. using a solvent comprised of a mixture of 89.9 weight percent 2-ethylhexanol and 10.1 weight percent heptane. In Example 6-1, one extraction was carried out. In Example 6-2, three cross-flow extractions were completed in the following fashion. The aqueous hydrogenation reaction effluent feed mixture was contacted with the specified solvent mixture at the given solvent to feed ratio, and the resulting aqueous ethylene glycol phase from the first extraction step was contacted with another portion of fresh solvent. This sequence was repeated an additional time for a total of three cross-flow extractions. The feed conditions for each set of extractions, the resulting Ru and phosphorus recovery into the extract phase, and the partition coefficient for ethylene glycol, P(EG), are summarized in Table 7.

In Experiments 6-3 and 6-4, water was added to Feed 4 (F-4), containing Triphos-Ru catalyst, to give the water content specified in Table 7. In addition, 1 weight percent (on an undiluted reactor effluent basis) of PDO was added to F-4. The resulting mixtures were contacted with a solvent mixture comprising 2-ethylhexanol and held at 60° C. The feed conditions for each set of extractions, the resulting Ru and phosphorus recovery in the extract phase, and the partition coefficient for ethylene glycol, P(EG), are summarized in Table 7.

Example 7

This example illustrates back extraction of a Triphos-Ru catalyst from the catalyst-rich extract mixtures of Experiments 6-1 and 6-3. The catalyst-rich extract mixture of Experiment 6-1, comprising 7.1 weight percent heptane in 2-ethylhexanol, was divided into four portions, and additional heptane was added to three of the portions as outlined in Table 8, Experiments 7-1 to 7-4. Each of these portions was subjected to cross-flow batch extractions at 60° C. using the glycolic acid/ester extractant at the solvent to feed ratio specified in Table 8. The resulting heptane/2-ethylhexanol phase from the first extraction step was contacted with another portion of fresh glycolic acid/ester extractant. The feed conditions for each set of extractions and the resulting Ru and phosphorus recovery into the glycolic acid/ester extract phase are summarized in Table 8.

The catalyst-rich extract mixture of Experiment 6-3, comprising 3.6 weight percent water, 87.7 weight percent 2-ethylhexanol, and 8.7 weight percent EG and reaction by-products, was divided into six portions, and additional heptane was added to three of the portions as outlined in Table 8, Experiments 7-5 to 7-10. In Experiment 7-5 and 7-6, the resulting mixtures were contacted with an aqueous solvent mixture comprising 60 weight percent glycolic acid. In Experiments 7-7 and 7-8, the resulting mixtures were contracted with an aqueous solvent mixture comprising 85 weight percent glycolic acid. In Experiment 7-9 and 7-10, the resulting mixtures were contacted with the glycolic acid/ester extractant. The resulting heptane/2-ethylhexanol phase from the first extraction step was contacted with another portion of fresh extractant. The feed conditions, solvent, solvent to feed ratio, and temperature for each set of extractions and the resulting Ru and phosphorus recovery into the extract phase are summarized in Table 8.

TABLE 7

Extraction of F-1 and F-4 with 2-EH and Heptane

| Ex. | Wt % 2-EH in Solvent | Wt % Heptane in Solvent | Wt % Water in Feed | T, ° C. | No. of Extract. Stages | S/F Ratio per Stage | % Recov Ru | % Recov Phos | P (EG) |
|---|---|---|---|---|---|---|---|---|---|
| F-2 | | | | | | | | | |
| 6-1 | 89.9% | 10.1% | 30% | 60 | 1 | 1.00 | 54% | 59% | 0.12 |
| 6-2 | 89.9% | 10.1% | 30% | 60 | 3 | 0.35 | 82% | 81% | 0.13 |
| F-4 | | | | | | | | | |
| 6-3 | 100% | 0% | 37% | 60 | 1 | 1.00 | 62.4 | 59.4 | 0.15 |
| 6-4 | 100% | 0% | 37% | 60 | 1 | 2.00 | 73.9 | 71.8 | 0.15 |

TABLE 8

Back Extraction of Extract from Examples 6-1 and 6-3

| Ex. | Wt % Heptane in Feed | Solvent | T, ° C. | No. of Extr. Stages | S/F Ratio per Stage | % Recov Ru | % Recov Phos |
|---|---|---|---|---|---|---|---|
| | | | Example 6-1 (F-2) | | | | |
| 7-1 | 7.1% | GA/ester | 60 | 2 | 0.71 | 94.3% | 91% |
| 7-2 | 18.9% | GA/ester | 60 | 2 | 0.71 | 95.1% | 94% |
| 7-3 | 26.5% | GA/ester | 60 | 2 | 0.72 | 96.5% | 89% |
| 7-4 | 36.2% | GA/ester | 60 | 2 | 0.71 | 96.7% | 87% |
| | | | Example 6-3 (F-4) | | | | |
| 7-5 | 0.0% | 60 wt % GA | 60 | 1 | 1.00 | 14.39% | 16% |
| 7-6 | 30.0% | 60 wt % GA | 60 | 1 | 1.00 | 23.05% | 36% |
| 7-7 | 0.0% | 85 wt % GA | 60 | 1 | 1.00 | 57.51% | 24% |
| 7-8 | 30.0% | 85 wt % GA | 60 | 1 | 1.00 | 38.31% | 69% |
| 7-9 | 0.0% | GA/ester | 100 | 1 | 1.00 | 66.95% | 58% |
| 7-10 | 30.00% | GA/ester | 100 | 1 | 1.00 | 86.17% | 82% |

Example 8

This example illustrates extractive recovery of an Ethyl-triphos-Ru catalyst from a glycolic acid hydrogenation reaction effluent. Various levels of water were added to Feed 3 (F-3) as shown in Table 9. These feed mixtures were subjected to a cross-flow batch extraction at 60° C. using an extractant (solvent) containing a mixture of 90 weight percent 2-ethylhexanol and 10 weight percent heptane. The feed conditions for each set of extractions and the resulting Ru and phosphorus recovery into the extract phase are summarized in Table 9.

Example 8 using the glycolic acid/ester extractant. The catalyst-rich extract mixtures of Experiment 8-1, 8-2, and 8-3 were each divided into four portions, and additional heptane was added to three of the portions as outlined in Table 10. Each of these portions was subjected to a cross-flow batch extractions at 60° C. using the glycolic acid/ester extractant at the solvent to feed ratio specified in Table 10. The feed conditions for each set of extractions and the resulting Ru and phosphorus recoveries into the extract phase are summarized in Table 10.

TABLE 9

Extraction of F-3 with 2-EH and Heptane

| Ex. | Wt % 2-EH in Solvent | Wt % Heptane in Solvent | Wt % Water in Feed | T, ° C. | No. of Extraction Stages | S/F Ratio per Stage | % Recov Ru | % Recov Phos | P(EG) |
|---|---|---|---|---|---|---|---|---|---|
| 8-1 | 90% | 10% | 6.30% | 60 | 1 | 1.00 | 33.2% | 31.8% | 0.34 |
| 8-2 | 90% | 10% | 24.95% | 60 | 1 | 1.00 | 10.4% | 9.86% | 0.18 |
| 8-3 | 90% | 10% | 44.93% | 60 | 1 | 1.00 | 5.8% | 6.77% | 0.06 |

Example 9

This example illustrates back extraction of an Ethyl-triphos-Ru catalyst from the catalyst-rich extract mixtures of

TABLE 10

Back Extraction of Extract from Examples 8-1 to 8-3 (F-3)

| Ex. | Extract Sample | Wt % 2-EH in Feed | wt % Heptane in Feed | T, ° C. | Number of Extr. Stages | S/F Ratio per Stage | % Recov. of Ru | % Recov. of Phos |
|---|---|---|---|---|---|---|---|---|
| 9-1 | 8-1 | 93.7% | 6.4% | 60 | 1 | 1.00 | 97.6% | 86.4% |
| 9-2 | 8-1 | 83.5% | 16.5% | 60 | 1 | 1.00 | 99.9% | 85.3% |
| 9-3 | 8-1 | 72.6% | 27.4% | 60 | 1 | 1.00 | 100.0% | 82.7% |
| 9-4 | 8-1 | 62.3% | 37.7% | 60 | 1 | 1.01 | 100.0% | 79.6% |
| 9-5 | 8-2 | 91.4% | 8.6% | 60 | 1 | 1.00 | 96.3% | 91.5% |
| 9-6 | 8-2 | 81.4% | 18.6% | 60 | 1 | 1.00 | 100.0% | 90.2% |
| 9-7 | 8-2 | 70.7% | 29.3% | 60 | 1 | 0.99 | 100.0% | 100.0% |
| 9-8 | 8-2 | 60.9% | 39.1% | 60 | 1 | 1.00 | 100.0% | 100.0% |
| 9-9 | 8-3 | 92.7% | 7.3% | 60 | 1 | 0.99 | 96.5% | 94.3% |
| 9-10 | 8-3 | 82.7% | 17.3% | 60 | 1 | 1.00 | 100.0% | 100.0% |
| 9-11 | 8-3 | 71.8% | 28.2% | 60 | 1 | 1.01 | 100.0% | 100.0% |
| 9-12 | 8-3 | 61.9% | 38.1% | 60 | 1 | 1.00 | 100.0% | 100.0% |

Example 10

This example illustrates back extraction of a BuO-triphos-Ru catalyst from a catalyst-rich extract mixture with various hydrophilic solvents. The catalyst-rich extract mixture was prepared by adding water to a portion of Feed 1 (F-1) so that the resulting mixture contained about 31 weight percent water. This feed mixture was subjected to a cross-flow batch extraction at 60° C. using an extractant containing a mixture of 90 weight percent 2-ethylhexanol and 10 weight percent decane as modifier. The solvent to feed weight ratio was 1.03:1. The top phase, a catalyst-rich extract mixture, comprising 9.3 weight percent decane in 2-ethylhexanol, other extracted components, and 86% of the BuO-triphos-Ru catalyst present in the original feed, was divided into nine portions, and additional decane was added to six of the portions as outlined in Table 11. Each of these portions was subjected to a cross-flow batch extractions, at the specified temperature and solvent to feed weight ratio, using a hydrophilic solvent containing one of the following: 1) water; 2) glycolic acid ester dimers and related oligomers; 3) glycolic acid, 85 weight percent in water. Results are summarized in Table 11.

TABLE 11

Back Extraction of Extract from F-1 extraction with 2-EH and decane

| Ex. | T, ° C. | Solvent | S/F Ratio | % Decane in Solvent Mix | P(Ru) | P(EG) |
|---|---|---|---|---|---|---|
| 10-1 | 60° C. | Water | 1.00 | 9.3% | 16.67 | 0.04 |
| 10-2 | 60° C. | Water | 1.00 | 24.4% | 33.33 | 0.03 |
| 10-3 | 60° C. | Water | 1.01 | 39.4% | 12.50 | 0.02 |
| 10-4 | 100° C. | GA dimers | 1.00 | 9.3% | 0.25 | (1) |
| 10-5 | 100° C. | GA dimers | 1.01 | 24.5% | 0.22 | (1) |
| 10-6 | 100° C. | GA dimers | 1.00 | 39.5% | 0.36 | (1) |
| 10-7 | 60° C. | 85% GA | 1.00 | 9.3% | 1.43 | 0.30 |
| 10-8 | 60° C. | 85% GA | 1.00 | 24.5% | 0.59 | 0.25 |
| 10-9 | 60° C. | 85% GA | 1.00 | 39.6% | 0.18 | 0.14 |

(1) Amount of EG in each phase was not measured in these experiments.

Example 11

This example illustrates back extraction of a Triphos-Ru catalyst from a catalyst-rich hydrophobic extract mixture with various hydrophilic solvents. The catalyst-rich extract mixture was prepared as follows. Water was added to a portion of Feed 2 (F-2) so that the resulting mixture contained about 31 weight percent water. This feed mixture was subjected to a cross-flow batch extraction at 60° C. using a extractant containing a mixture of 90 weight percent 2-ethylhexanol and 10 weight percent decane as modifier. The solvent to feed weight ratio was 1.03:1. The top phase, a catalyst-rich extract mixture, comprising 9.3 weight percent decane in 2-ethylhexanol, other extracted components, and 59% of the Triphos-Ru catalyst present in the original feed, was divided into nine portions, and additional decane was added to six of the portions as outlined in Table 12. Each of these portions was subjected to a cross-flow batch extraction, at the specified temperature and solvent to feed weight ratio, using a hydrophilic solvent comprised of one of the following: 1) water; 2) glycolic acid ester dimers and related oligomers; 3) glycolic acid, 85 weight percent in water. Results are summarized in Table 12.

TABLE 12

Back Extraction of F-2 Extract (2-EH and Decane) with Various Solvents

| Ex. | T, ° C. | Solvent | S/F Ratio | % Decane in Solvent Mix | P(Ru) | P(EG) |
|---|---|---|---|---|---|---|
| 11-1 | 60° C. | water | 1.00 | 9.3% | ∞ | 0.04 |
| 11-2 | 60° C. | water | 1.00 | 24.5% | 50.00 | 0.03 |
| 11-3 | 60° C. | water | 1.00 | 39.5% | 14.29 | 0.02 |
| 11-4 | 100° C. | GA dimers | 1.00 | 9.3% | 3.33 | Not meas. |
| 11-5 | 100° C. | GA dimers | 1.00 | 24.6% | 1.75 | Not meas. |
| 11-6 | 100° C. | GA dimers | 1.00 | 39.6% | 3.85 | Not meas. |
| 11-7 | 60° C. | 85% GA | 0.99 | 9.3% | 14.29 | 0.40 |
| 11-8 | 60° C. | 85% GA | 1.00 | 24.7% | 4.35 | 0.24 |
| 11-9 | 60° C. | 85% GA | 1.00 | 30.00% | 1.59 | 0.17 |

Example 12

Figure 2:
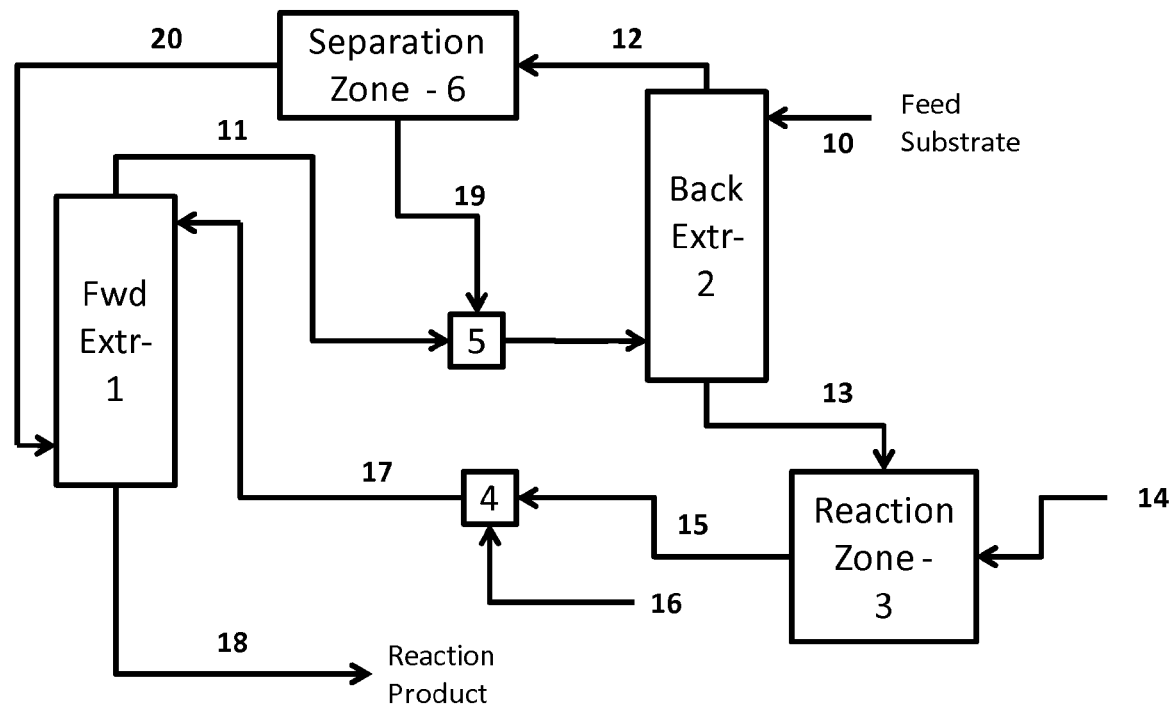
FIG. 2 is a schematic flow diagram for another embodiment of the invention in which a hydrophobic solvent from the back extractor is recovered in a separation zone and combined with the catalyst-rich hydrophobic extract from the forward extractor.
Figure 3:
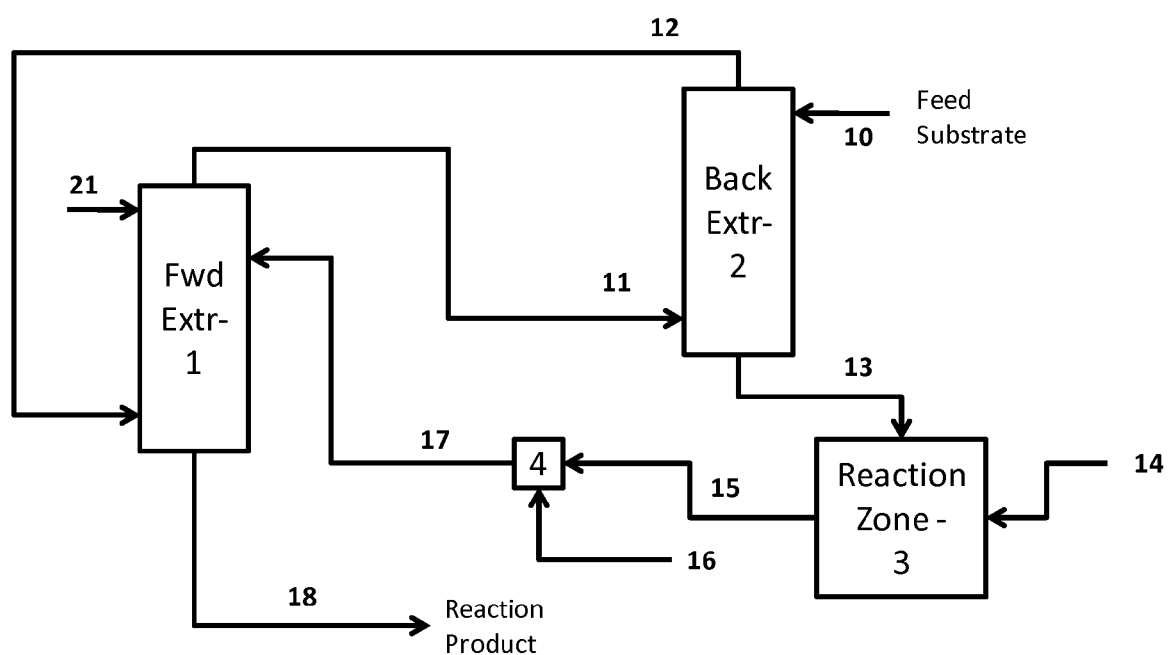
FIG. 3 is a schematic flow diagram illustrating another embodiment of the invention in which the forward extraction zone is operated as a fractional countercurrent extraction.

This example illustrates a computer-generated material balance for an embodiment of the instant invention that is illustrated in FIG. 2 for the extractive recovery of the Triphos-Ru catalyst from a glycolic acid hydrogenation reaction effluent. The glycolic acid hydrogenation reaction effluent composition taken from Feed 2 (F-2). Stream ID's are as shown in FIG. 2. The extractant stream 20 for the forward extraction contains 10 weight percent heptane in 2-ethylhexanol. The feed substrate extractant stream 10 for the back extraction is a mixture of glycolic acid/ester described above. The remainder of the extractant stream enters Reaction Zone 3 via stream 14. The system was modeled using the Kremser method, as described in Treybal, *Liquid Extraction*, 2$^{nd}$ Ed., McGraw Hill, 1963, pp. 248-252, for both the forward and back extractions, with partition coefficients correlated from the data of Examples 1 and 3. Material balance data is given in Table 13A. Heptane was added to the extract stream 11 of Forward Extractor 1 via stream 19 and later removed from the raffinate stream 12 of Back Extractor 2 via Separation Zone 6. The reaction product stream 18 comprises 46034 kg/hr of ethylene glycol. A summary of the resulting extractor column design parameters are given in Table 13B.

TABLE 13A

Calculated Material Balances for a Recovery Process Illustrated by FIG. 2
(All values in kg/hr)

| Stream ID | Ru | P | EG | H$_2$O | 2-EH | Heptane | EG glycolates | Total |
|---|---|---|---|---|---|---|---|---|
| 10 | | | 1238 | 236 | | | 43134 | 44608 |
| 11 | 3.84 | 3.85 | 7533 | 1587 | 69253 | 7695 | 220 | 87040 |
| 12 | 0.00 | 0.00 | 50 | 1 | 68475 | 19773 | | 88565 |
| 13 | 3.84 | 3.84 | 8721 | 1822 | 778 | 11 | 43833 | 55173 |
| 14 | | | 35 | 7 | | | 3629 | 3671 |
| 15 | 3.85 | 3.85 | 53568 | 17562 | | | 2158 | 76948 |
| 16 | | | | 0 | | | | 0 |
| 17 | 3.85 | 3.85 | 53568 | 17562 | 0 | 0 | 2158 | 76948 |
| 18 | 0.00 | 0.00 | 46034 | 15976 | 0 | 0 | 1939 | 66857 |
| 19 | | | | | | 12089 | | 12089 |
| 20 | | | | | 69253 | 7695 | | 76948 |

TABLE 13B

Extractor Column Design Parameters

| | S/F Ratio | Stages | Diameter (M) | % Ru Recov | Total Flow, (kg/hr) | EG Prod. (kg/hr) | % EG Glycolates to Back Extr | Heptane Distilled, (kg/hr) |
|---|---|---|---|---|---|---|---|---|
| Fwd | 1.00 | 12 | 2.6 | 99.92% | 153897 | 46034 | | |
| Back | 0.45 | 8 | 2.6 | 99.99% | 143738 | | 92% | 12089 |

Example 13

This example illustrates a computer-generated material balance for another embodiment of the instant invention that can be illustrated in FIG. 2 for the extractive recovery of a BuO-triphos-Ru catalyst from a glycolic acid hydrogenation effluent as exemplified Feed 3 (F-3). Stream ID's are as shown in FIG. 2. The extractant stream 20 for the forward extraction is 10 weight percent heptane in 2-ethylhexanol. The feed substrate extractant stream 10 for the back extraction is a mixture of glycolic acid and glycolate esters of ethylene glycol as exemplified in Example 9 and by the glycolic acid/ester extractant mixture described above. The remainder of the bis-glycolates enters Reaction Zone 3 via stream 14. The system was modeled using the Kremser method, as described in in Treybal, *Liquid Extraction*, 2$^{nd}$ Ed., McGraw Hill, 1963, pp. 248-252, for both the forward and back extractions, with partition coefficients correlated from the data of Examples 2 and 6. Material balance data is given in Table 14A. Heptane was added to the extract stream 11 of Forward Extractor 1 via stream 19 and later removed from the raffinate stream 12 of Back Extractor 2 via Separation Zone 6. The reaction product stream 18 comprises 46034 kg/hr of ethylene glycol. A summary of the resulting extractor column design parameters are given in Table 14B.

TABLE 14A

Calculated Material Balances for a Recovery Process Illustrated by FIG. 2
(All values in kg/hr)

| Steam ID | Ru | P | EG | H2O | 2-EH | Heptane | EG glycolates | Total |
|---|---|---|---|---|---|---|---|---|
| 10 | | | 1145 | 218 | | | 39874 | 41236 |
| 11 | 3.51 | 3.51 | 2819 | 597 | 25554 | 2839 | 82 | 32177 |
| 12 | 0.00 | 0.00 | 0 | 0 | 24611 | 10932 | | 35543 |
| 13 | 3.51 | 3.51 | 3964 | 815 | 943 | 20 | 40234 | 45983 |
| 14 | | | 131 | 25 | | | 13705 | 13861 |
| 15 | 3.51 | 3.51 | 48854 | 16017 | | | 1969 | 70177 |
| 16 | | | | 0 | | | | 0 |
| 17 | 3.51 | 3.51 | 48854 | 16017 | 0 | 0 | 1969 | 70177 |
| 18 | 0.00 | 0.00 | 46034 | 15420 | 0 | 0 | 1886 | 66393 |
| 19 | | | | | | 8112 | | 8112 |
| 20 | | | | | 25554 | 2839 | | 28394 |

TABLE 14B

Extractor Column Design Parameters

|  | S/F Ratio | Stages | Diameter (M) | % Ru Recov | Total Flow (kg/hr) | EG Prod. (kg/hr) | % Bis Glycolates to Back Extr | Heptane Distilled (kg/hr) |
|---|---|---|---|---|---|---|---|---|
| Fwd | 0.40 | 8 | 2.0 | 99.92% | 98570 | 46034 |  |  |
| Back | 1.02 | 12 | 1.9 | 99.99% | 81526 |  | 75% | 8112 |

Example 14

This example illustrates a computer-generated material balance for an embodiment of the instant invention that can be illustrated in FIG. 4 for the extractive recovery of a Triphos-Ru catalyst from a glycolic acid hydrogenation product effluent as Feed 2 (F-2). Stream ID's are as shown in FIG. 4. The extractant stream 20 for the forward extraction is 15 weight percent heptane in 2-ethylhexanol at a solvent to feed ratio of 0.70. Water wash enters Forward Extractor 1 via stream 21 at a ratio of 0.2 kg per kg of solvent. The feed substrate extractant stream 10 for the back extraction is a mixture of glycolic acid and glycolate esters of ethylene glycolates as exemplified in Example 3 and by the glycolic acid/ester extractant mixture described above. The system was modeled using the Kremser method, as described in Treybal, *Liquid Extraction*, $2^{nd}$ Ed., McGraw Hill, 1963, pp. 248-252, for both the forward and back extractions, with partition coefficients correlated from the data of Examples 3 and 7. Material balance data is given in Table 15A. No heptane was added to the extract stream 11 of Forward Extractor 1. The reaction product stream 18 comprises 77,369 kg/hr of ethylene glycol. A summary of the resulting extractor column design parameters are given in Table 15B.

Example 15

This example illustrates a computer-generated material balance for an embodiment of the instant invention that can be illustrated by FIG. 4 for the extractive recovery of the BuO-triphos-Ru catalyst from a glycolic acid hydrogenation effluent Feed 1 (F-1). Stream ID's are as shown in FIG. 4. The solvent stream 20 for the forward extraction is 15 weight percent heptane in 2-ethylhexanol at a solvent to feed ratio of 1.5. Water wash enters Forward Extractor 1 via stream 21 at a ratio of 0.2 kg per kg of solvent. The feed substrate solvent stream 10 for the back extraction is a mixture of glycolate esters of ethylene glycol as exemplified in Example 7 and by the glycolic acid/ester extractant mixture described above. The system was modeled using the Kremser method, as described in Treybal, *Liquid Extraction*, $2^{nd}$ Ed., McGraw Hill, 1963, pp. 248-252, for both the forward and back extractions, with partition coefficients correlated from the data of Examples 7 and 11. Material balance data is given in Table 16A. No heptane was added to the extract stream 11 of Forward Extractor 1. The reaction product stream 18 comprises 77,369 kg/hr of ethylene glycol. A summary of the resulting extractor column design parameters are given in Table 16B.

TABLE 15A

Calculated Material Balances for a Recovery Process Illustrated by FIG. 4
(All values in kg/hr)

| Stream ID | Ru | P | EG | H$_2$O | 2-EH | Heptane | EG glycolates | Other Polar Compounds |
|---|---|---|---|---|---|---|---|---|
| 10 | 0.000 | 0.000 | 5,471 | 3,230 | 0 | 0 | 54,034 | 10,322 |
| 11 | 4.518 | 4.519 | 160 | 1,088 | 47,913 | 8,736 | 0 | 171 |
| 12 | 0.004 | 0.003 | 962 | 404 | 44,905 | 8,709 | 2,900 | 5,709 |
| 13 | 4.515 | 4.516 | 4,669 | 3,914 | 3,009 | 27 | 51,134 | 23,866 |
| 14 | 0.000 | 0.000 | 0 | 0 | 0 | 0 | 0 | 0 |
| 15 | 4.517 | 4.517 | 76,567 | 9,760 | 940 | 0 | 428 | 9,626 |
| 16 | 0.000 | 0.000 | 0 | 0 | 0 | 0 | 0 | 0 |
| 17 | 4.517 | 4.517 | 76,567 | 9,760 | 940 | 0 | 428 | 9,626 |
| 18 | 0.002 | 0.001 | 77,369 | 22,684 | 2,664 | 24 | 3,328 | 15,164 |
| 19 | 0.000 | 0.000 | 0 | 0 | 0 | 0 | 0 | 0 |
| 20 | 0.004 | 0.003 | 962 | 404 | 49,638 | 8,760 | 2,900 | 5,709 |
| 21 | 0.00 | 0.00 | 0 | 13,608 | 0 | 0 | 0 | 0 |

TABLE 15B

Extractor Column Design Parameters

|  | S/F Ratio | W/S Ratio | Stages | Diam. (M) | % Ru Recov | Total Flow, (kg/hr) | EG Prod. (kg/hr) | % EG Glycolates to Back Extr | Heptane Distilled, (kg/hr) |
|---|---|---|---|---|---|---|---|---|---|
| Fwd | 0.70 | 0.20 | 12 | 2.8 | 99.95% | 179,310 | 77,369 | 100% | 0 |
| Back | 1.59 |  | 10 | 2.5 | 99.92% | 150,217 |  |  |  |

TABLE 16A

Calculated Material Balances for a Recovery Process Illustrated by FIG. 4
(All values in kg/hr)

| Stream ID | Ru | P | EG | $H_2O$ | 2-EH | Heptane | EG glycolates | Other Polar Compounds |
|---|---|---|---|---|---|---|---|---|
| 10 | 0.000 | 0.000 | 5,471 | 3,230 | 0 | 0 | 54,034 | 10,322 |
| 11 | 4.515 | 4.514 | 292 | 3,056 | 123,358 | 21,884 | 0 | 366 |
| 12 | 0.000 | 0.000 | 2,470 | 1,047 | 120,332 | 21,857 | 7,561 | 11,834 |
| 13 | 4.514 | 4.513 | 3,293 | 5,239 | 3,027 | 27 | 46,474 | 17,936 |
| 14 | 0.000 | 0.000 | 0 | 0 | 0 | 0 | 0 | 0 |
| 15 | 4.517 | 4.517 | 76,567 | 9,760 | 940 | 0 | 428 | 9,626 |
| 16 | 0.000 | 0.000 | 0 | 0 | 0 | 0 | 0 | 0 |
| 17 | 4.517 | 4.517 | 76,567 | 9,760 | 940 | 0 | 428 | 9,626 |
| 18 | 0.002 | 0.003 | 78,746 | 41,295 | 1,677 | 15 | 7,988 | 21,094 |
| 19 | 0.000 | 0.000 | 0 | 0 | 0 | 0 | 0 | 0 |
| 20 | 0.000 | 0.000 | 2,470 | 1,047 | 124,095 | 21,899 | 7,561 | 11,834 |
| 21 | 0.00 | 0.00 | 0 | 33,544 | 0 | 0 | 0 | 0 |

TABLE 16B

Extractor Column Design Parameters

| | S/F Ratio | W/S Ratio | Stages | Diam. (M) | % Ru Recov | Total Flow, (kg/hr) | EG Prod. (kg/hr) | % EG Glycolates to Back Extr | Heptane Distilled, (kg/hr) |
|---|---|---|---|---|---|---|---|---|---|
| Fwd | 1.74 | 0.20 | 12 | 3.7 | 99.95% | 299,779 | 78,746 | 100% | 0 |
| Back | 0.62 | | 5 | 3.3 | 99.99% | 241,104 | | | |

Example 16

This example illustrates the extractive recovery of the Triphos-Ru catalyst from glycolic acid hydrogenation effluents, Feed 4 through Feed 7 (F-4, F-5, F-6, and F-7). Water was added to the reactor effluents as shown in Table 17. These feed mixtures were subjected either to one or more cross-flow extractions or to a cascaded series of cross-flow batch extractions that simulate a multistage continuous counter-current extraction process. Cross-flow extractions were completed in the following fashion. The aqueous hydrogenation reaction effluent feed mixture was contacted with the specified solvent mixture at the given solvent to feed ratio, and the resulting aqueous ethylene glycol phase from the first extraction step was contacted with another portion of fresh solvent. This sequence was repeated until a desired number of cross-flow stages were achieved as shown in Table 17. Simulated multistage continuous counter-current extractions were completed in the following fashion. A portion of a given glycolic acid hydrogenation effluent and water feed mixture was first contacted with fresh solvent in a series of cross-flow extractions to simulate the desired number of stages. The solvent-rich phase from the first cross-flow extraction was then contacted with another portion of fresh hydrogenation effluent mixture. The aqueous phase from this extraction was then contacted with the solvent-rich phase from the second cross-flow extraction. This cascaded pattern was then extended to all cross-flow extractions and cycled 5 to 6 times to approach equilibrium conditions. The simulated counter-current extraction technique used herein is well-known to those skilled in the art and is laid out in detail in Treybal ("Liquid Extraction," 2nd Ed., McGraw-Hill Book Company, New York, N.Y., 1963, pp. 349-366). The feed mixtures and final cross-flow and multistage extract and raffinate streams were analyzed by GC and ICP methods. The feed conditions for each set of extractions, the solvent used, the extraction pattern, the number of stages, the S/F ratios, the extraction temperature, and the resulting Ru and phosphorus recovery into the extract phase, are summarized in Table 17.

TABLE 17

Cross-flow and Simulated Multi-stage, Continuous, Counter-Current Extractions

| Ex. | Feed | Solvent | Wt % Water in Feed | Extraction pattern | No. Extr. Stages | S/F Ratio(1) | Temp (° C.) | % Ru Recov | % Phos Recov |
|---|---|---|---|---|---|---|---|---|---|
| 16-1 | F-4 | 2-EH | 37.1% | Cross-flow | 1 | 1.00 | 60 | 61.1% | 62.6% |
| 16-2 | F-4 | 2-EH | 37.1% | Cross-flow | 3 | 1.00 | 60 | 89.6% | 91.8% |
| 16-3 | F-4 | 2-EH | 37.0% | Multistage | 6 | 1.00 | 60 | 89.8% | 93.1% |
| 16-4 | F-5 | 2-EH | 71.0% | Cross-flow | 3 | 1, 1.06, 1.13 | 60 | 88.7% | 85.6% |
| 16-5 | F-5 | Pentanol | 71.0% | Cross-flow | 3 | 1, 1.3, 1.9 | 60 | 98.8% | 96.7% |
| 16-6 | F-5 | Pentanol | 71.0% | Multistage | 3 | 1.00 | 60 | 96.2% | 90.8% |
| 16-7 | F-6 | 2-EH (sat.) | 27.6% | Cross-flow | 6 | 1, 1.2, 1.4, 1.6, 1.9, 2.3 | 60 | 84.5% | 66.6% |
| 16-8 | F-6 | Hexanol (sat.) | 27.6% | Cross-flow | 1 | 1.00 | 60 | 78.5% | 67.9% |

TABLE 17-continued

Cross-flow and Simulated Multi-stage, Continuous, Counter-Current Extractions

| Ex. | Feed | Solvent | Wt % Water in Feed | Extraction pattern | No. Extr. Stages | S/F Ratio(1) | Temp (° C.) | % Ru Recov | % Phos Recov |
|---|---|---|---|---|---|---|---|---|---|
| 16-9 | F-6 | Hexanol (sat.) | 53.4% | Cross-flow | 6 | 1, 1.2, 1.4, 1.6, 1.8, 2 | 60 | 91.1% | 66.6% |
| 16-10 | F-6 | Hexanol (sat.) | 67.8% | Cross-flow | 6 | 1, 1.1, 1.2, 1.3, 1.4, 1.5 | 60 | 92.4% | 63.3% |
| 16-11 | F-6 | Pentanol (sat.) | 73.0% | Multistage | 6 | 1.00 | 60 | 95.9% | 65.2% |
| 16-12 | F-7 | Pentanol | 50.0% | Multistage | 3 | 1.00 | 25 | 100.0% | 95.2% |

Figure 7:
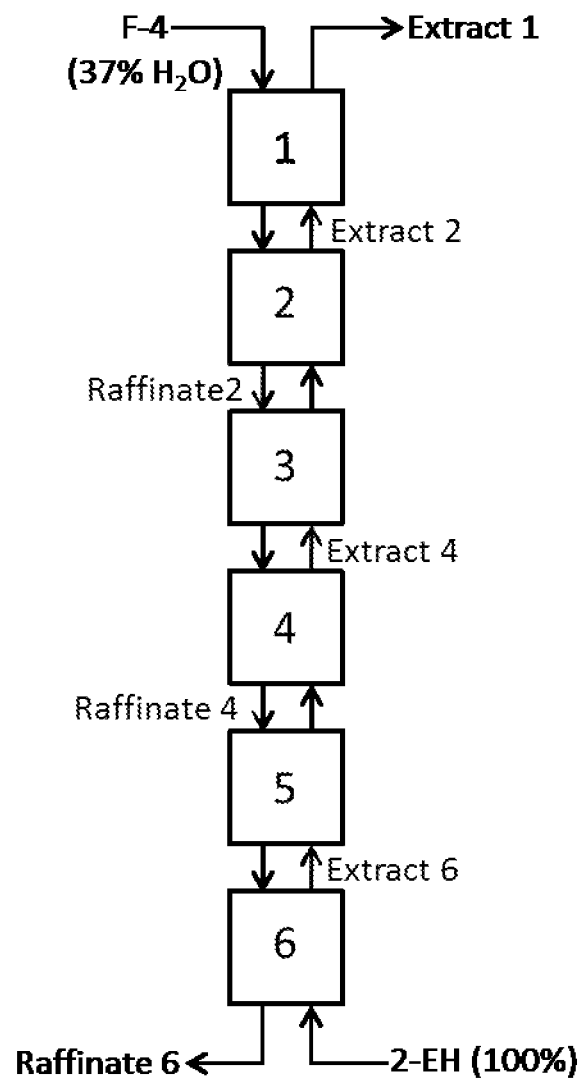
FIG. 7 is a schematic flow diagram of a multi-stage extractor.

(1) When one S/F ratio is given and the number of stages is greater than one, each stage had the same S/F ratio. When more than one S/F ratio is given, they are given in the order of stage numbers as shown in FIG. 7.

The concentration profile of Ru and phosphorus in a simulated multistage continuous counter-current extraction is shown in Table 18 for Experiment 16-3 (Table 17). The simulated stage numbers are as identified in FIG. 7. The glycolic acid hydrogenation effluent, F-4, was mixed with water to contain 37 weight percent water and entered stage 1. The extractant, 2-ethylhexanol, entered below stage 6. The solvent-rich phase (extract) flowed from stage 6 to 1, while the aqueous hydrogenation effluent mixture flowed from 1 to 6.

TABLE 18

Simulated Multi-Stage Extraction - Ru and Phosphorus Concentration Profiles

| Stream | Stage | Stream wt, grams | Ru (ppm) | Phos (ppm) |
|---|---|---|---|---|
| F-4 (37% $H_2O$) | above 1 | 10.00 | 330 | 321 |
| 2-EH (100%) | below 6 | 10.00 | 0 | 0 |
| Raffinate | 2 | 10.12 | 128 | 124 |
| Raffinate | 4 | 10.20 | 59.8 | 55.1 |
| Raffinate | 6 | 9.03 | 37.8 | 25.8 |
| Extract | 1 | 11.15 | 266 | 269 |
| Extract | 2 | 11.14 | 123 | 132 |
| Extract | 4 | 11.10 | 55.2 | 63.6 |
| Extract | 6 | 10.93 | 11.5 | 20 |

Example 17

This experiment shows the use of a single stage distillation as a means for separating the extractant from the catalyst system. The extract products from each cycle of the simulation multi-stage extraction of Experiment 16-6 (Table 17) were combined in a round bottom flask and distilled in a single-stage distillation apparatus. The pot was initially heated to 70° C. while pressure was carefully brought down to 50 torr. To maintain a steady boil-up rate, the pot temperature was then slowly raised until it reached 110° C. The mass, composition, and recoveries of both extraction (results of extract and raffinate phase from the final cycle) and distillation are shown in Table 19.

TABLE 19

Extraction Followed by Single-Stage Distillation

| | ID | Liquid-liquid Extraction | | | | Distillation | | | Recoveries | |
|---|---|---|---|---|---|---|---|---|---|---|
| | | Feed | Solvent | Extract | Raffinate | Feed | Pot | Distil | Extract | Distil |
| | Mass (g) | 13.00 | 13.00 | 16.34 | 9.21 | 95.06 | 9.26 | 81.37 | | |
| | Ru (ppm) | 22 | | 16.8 | 1 | 17 | 182 | — | 96.0% | — |
| | Phos (ppm) | 24.9 | | 17.8 | 2.6 | 17.9 | 190 | — | 89.9% | — |
| GC Results, wt % | 1-Pentanol | | 100 | 80.0 | 2.9 | 78.7 | 12.4 | 89.5 | 100.5% | 97% |
| | Water | 70.32 | | 14.9 | 69.4 | 14.8 | 2.3 | 11.8 | 26.6% | 68% |
| | EG | 3.22 | | 0.9 | 3.6 | 1.4 | 8.6 | 0.5 | 36.7% | 31% |
| | DEG | 0.62 | | 0.2 | 0.6 | 0.3 | 2.7 | 0.0 | 41.7% | 4% |
| | TEG | 0.09 | | 0.0 | 0.1 | 0.0 | 0.4 | | 32.8% | 0% |
| | G1 | 6.23 | | 2.1 | 6.4 | 2.8 | 22.6 | 0.1 | 43.0% | 4% |
| | G2 | 0.50 | | 0.1 | 0.4 | 0.1 | 1.7 | | 29.5% | 0% |
| | HGEgH | 7.67 | | 1.8 | 6.2 | 1.4 | 16.0 | 0.0 | 30.0% | 2% |
| | HGEg2H | 0.90 | | 0.2 | 0.7 | 0.1 | 2.1 | | 28.2% | 0% |
| | HGEgG'H | 1.64 | | 0.3 | 1.2 | 0.1 | 2.0 | | 21.5% | 0% |
| | HG2EgH | 1.32 | | 0.3 | 1.1 | 0.2 | 2.4 | | 28.3% | 0% |
| | HGEg2G'H | 0.34 | | 0.0 | 0.3 | 0.0 | 0.4 | | 17.2% | 0% |
| | HG2EgG'H | 0.52 | | 0.1 | 0.4 | 0.0 | 0.6 | | 19.5% | 0% |
| | 1,2,3-Butanetriols | 0.11 | | 0.0 | 0.1 | 0.1 | 2.6 | | 31.2% | 0% |
| | Other Knowns | 0.60 | | 0.1 | 0.5 | 0.2 | 1.1 | 0.1 | 28.1% | 51% |
| | Unknown | 1.99 | | 1.4 | 1.9 | 2.0 | 9.8 | 1.4 | 89.9% | 59% |
| | Total | 96.08 | | 102.6 | 95.7 | 102.3 | 87.6 | 103.5 | | |

We claim:

1. A process for recovering a homogeneous catalyst, comprising
(A) extracting a feed comprising:
(i) a glycolic acid hydrogenation effluent, comprising
(a) about 10 to about 99 weight percent ethylene glycol, about 0.5 to about 50 weight percent water, and about 0.5 to about 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of said glycolic acid hydrogenation effluent; and
(b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes; and
(ii) additional water whereby said feed comprises about 5 to about 50 weight percent water based on the total weight of said glycolic acid hydrogenation effluent and said additional water;
with a first extractant, comprising
(i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
(ii) optionally, a hydrophilic solvent;
to form a first raffinate phase comprising a major amount of said ethylene glycol and a minor amount of said catalyst composition contained in said glycolic acid hydrogenation effluent and a first extract phase comprising a major amount of said catalyst composition and a minor amount of said ethylene glycol contained in said glycolic acid hydrogenation effluent;
(B) separating said first raffinate phase and said first extract phase; and
(C) recovering said catalyst composition from said first extract phase of step (B) by:
(i) extracting said first extract phase of step (B) with a second extractant comprising water, ethylene glycol, glycolate esters of ethylene glycol, glycolic acid, glycolic acid oligomers, or mixtures thereof to form a second extract phase comprising a major amount of said catalyst composition contained in said first extract phase of step (B) and a second raffinate phase comprising a minor amount of said catalyst composition contained in said first extract phase of step (B); or
(ii) distilling said first extract phase of step (B) to form a distillate comprising a major amount of said hydrophobic solvent contained in said first extract phase of step (B) and a bottoms comprising a major amount of said catalyst composition contained in said first extract phase of step (B).

2. The process according to claim 1 wherein said glycolic acid hydrogenation effluent comprises about 40 to about 99 weight percent ethylene glycol, about 0.5 to about 40 weight percent water, and about 0.5 to about 40 weight percent of said one or more reaction by-products.

3. The process according to claim 1 wherein said glycolic acid hydrogenation effluent comprises about 80 to about 95 weight percent ethylene glycol, about 1 to about 15 weight percent water, and about 1 to about 15 weight percent of said one or more reaction by-products.

4. The process according to claim 1 wherein said feed comprises about 10 to about 30 weight percent water based on the total weight of said glycolic acid hydrogenation effluent and said additional water.

5. The process according to claim 1 wherein said tridentate ligand comprises 1,1,1-tris(diphenylphosphinomethyl)methane, 1,1,1-tris(diphenylphosphinomethyl)ethane, (2-(butoxymethyl)-2-((diphenylphosphino)methyl)propane-1,3-diyl)bis(diphenylphosphine), (2-(benzyloxymethyl)-2-((diphenylphosphino)methyl)propane-1,3-diyl)bis(diphenylphosphine), 1,1,1-tris(diphenylphosphinomethyl)propane, 1,1,1-tris(diphenylphosphinomethyl)butane, 1,1,1-tris(diphenylphosphinomethyl)-2,2-dimethylpropane, 1,1,1-tris(diphenylphosphinomethyl)cyclohexane, 1,1,1-tris(dicyclohexylphosphinomethyl)ethane, 1,1,1-tris(dimethylphosphinomethyl)ethane, 1,1,1-tris(diethylphosphinomethyl)ethane, or mixtures thereof.

6. The process according to claim 1 wherein said tridentate ligand comprises 1,1,1-tris(diphenylphosphinomethyl)ethane.

7. The process according to claim 1 wherein said hydrophobic solvent is selected from 2-ethylhexanol, butanol, pentanol, hexanol, heptanol, octanol, nonanol, decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof.

8. The process according to claim 1 wherein said hydrophobic solvent further comprises a hydrocarbon having from 5 to 20 carbon atoms.

9. The process according to claim 8 wherein said hydrocarbon is selected from hexane, heptane, octane, decane, benzene, toluene, xylenes, methyl napththalenes, isoparaffinic mixed hydrocarbons having a boiling range between 90 and 325° C., and mixtures thereof.

10. The process according to claim 1 wherein said first extractant comprises a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having from 2 to 6 carbon atoms, acetic acid, formic acid, α-hydroxy carboxylic acids having from 4 to 6 carbon atoms, glycolic acid oligomers having from 2 to 6 repeat units, polyol and diol esters of glycolic acid, and mixtures thereof.

11. The process according to claim 2 wherein said catalyst composition is recovered by extracting said first extract phase of step (B), and wherein said second extractant comprises mono- and diglycolate esters of ethylene glycol.

12. The process according to claim 11 wherein said tridentate ligand comprises 1,1,1-tris(diphenylphosphinomethyl)ethane and said hydrophobic solvent comprises 2-ethylhexanol and heptane.

13. The process according to claim 1 further comprising passing said second extract phase or said bottoms of step (C) to a process for the preparation of ethylene glycol by hydrogenation of glycolic acid, glycolate esters, glycolic acid oligomers, or mixtures thereof to ethylene glycol.

14. The process according to claim 1 further comprising combining said second raffinate phase of step (C) with said first extractant of step (A), distilling said second raffinate phase of step (C) to produce a hydrophobic solvent distillate and combining said hydrophobic solvent distillate with said first extractant of step (A), or combining said distillate of step (C) with said first extractant of step (A).

15. The process according to claim 1 wherein said catalyst composition is recovered by extracting said first extract phase of step (B) and wherein step (A) and/or step (C) are carried out by fractional countercurrent extraction.

16. A process for recovering a homogeneous catalyst, comprising
(A) extracting a feed comprising:
  (i) a glycolic acid hydrogenation effluent, comprising
    (a) about 40 to about 99 weight percent ethylene glycol, about 0.5 to about 40 weight percent water, and about 0.5 to about 40 weight percent of one or more reaction by-products selected from glycolic acid, glycolic acid oligomers, ethylene glycol oligomers, glycolate esters, 1,2-propanediol, 1,2-butanediol, and polyols, each based on the total weight of said glycolic acid hydrogenation effluent; and
    (b) a catalyst composition comprising ruthenium and 1,1,1-tris(diphenylphosphinomethyl)ethane; and
  (ii) additional water whereby said feed comprises about 5 to about 40 weight percent water based on the total weight of said glycolic acid hydrogenation effluent and said additional water;
  with a first extractant, comprising about 60 to 100 weight percent 2-ethylhexanol, pentanol, isobutyl isobutyrate, undecanone, methylisobutyl ketone, diisopropyl ether, or mixtures thereof and 0 to about 40 weight percent of a hydrocarbon having from 5 to 20 carbon atoms, each based on the total weight of said first extractant, to form a first raffinate phase comprising a major amount of said ethylene glycol and a minor amount of said catalyst composition contained in said glycolic acid hydrogenation effluent and a first extract phase comprising a major amount of said catalyst composition and a minor amount of said ethylene glycol contained in said glycolic acid hydrogenation effluent;
(B) separating said first raffinate phase and said first extract phase;
(C) extracting said first extract phase of step (B) with a second extractant comprising water, ethylene glycol, glycolate esters of ethylene glycol, glycolic acid, glycolic acid oligomers, or mixtures thereof to form a second extract phase comprising a major amount of said catalyst composition contained in said first extract phase of step (B) and a second raffinate phase comprising a minor amount of said catalyst composition contained in said first extract phase of step (B); and
(D) combining said second raffinate phase of step (C) with said first extractant of step (A), or distilling said second raffinate phase of step (C) to produce a hydrophobic solvent distillate and combining said hydrophobic solvent distillate with said first extractant of step (A).

17. The process according to claim 16 wherein said glycolic acid hydrogenation effluent comprises about 80 to about 95 weight percent ethylene glycol, about 1 to about 15 weight percent water, and about 1 to about 15 weight percent of said one or more reaction by-products, and wherein said feed comprises about 10 to about 30 weight percent water based on the total weight of said glycolic acid hydrogenation effluent and said additional water.

18. The process according to claim 16 wherein said hydrophobic solvent comprises 2-ethylhexanol and heptane, and further comprising passing said second extract phase of step (C) to a process for the preparation of ethylene glycol by hydrogenation of glycolic acid, glycolate esters, glycolic acid oligomers, or mixtures thereof to ethylene glycol.

19. A process for recovering a homogeneous catalyst, comprising
(A) contacting an aqueous mixture comprising glycolic acid, glycolate esters, methyl glycolate, oligomers of glycolic acid, or mixtures thereof, with hydrogen in the presence of a catalyst composition comprising ruthenium and 1,1,1-tris(diphenylphosphinomethyl)ethane to form a glycolic acid hydrogenation effluent comprising about 80 to about 95 weight percent ethylene glycol, about 0.5 to about 15 weight percent water, and about 0.5 to about 15 weight percent of one or more reaction by-products selected from glycolic acid, glycolic acid oligomers, ethylene glycol oligomers, glycolate esters, 1,2-propanediol, 1,2-butanediol, and polyols, each based on the total weight of said glycolic acid hydrogenation effluent, and said catalyst composition;
(B) extracting a feed comprising said glycolic acid hydrogenation effluent and additional water whereby said feed comprises about 10 to about 30 weight percent water, based on the total weight of said glycolic acid hydrogenation effluent and said additional water, with a first extractant comprising about 60 to 100 weight percent 2-ethylhexanol and 0 to about 40 weight percent of a hydrocarbon having from 5 to 20 carbon atoms, each based on the total weight of said first extractant, to form a first raffinate phase comprising a major amount of said ethylene glycol contained in said glycolic acid hydrogenation effluent and a first extract phase comprising a major amount of said catalyst composition contained in said glycolic acid hydrogenation effluent;
(C) separating said first raffinate phase and said first extract phase;
(D) extracting said first extract phase of step (C) with a second extractant comprising water, ethylene glycol, glycolate esters of ethylene glycol, glycolic acid, glycolic acid oligomers, or mixtures thereof to form a second extract phase comprising a major amount of said catalyst composition contained in said first extract phase of step (C) and a second raffinate phase comprising a minor amount of said catalyst composition contained in said first extract phase of step (C); and
(E) combining said second extract phase of step (D) with said aqueous mixture of step (A).

20. A process for recovering a homogeneous catalyst, comprising
(A) extracting a feed comprising:
  (i) a glycolic acid hydrogenation effluent, comprising
    (a) about 0.5 to about 50 weight percent ethylene glycol, about 0.5 to about 50 weight percent water, and about 25 to about 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of said glycolic acid hydrogenation effluent; and
    (b) a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes; and
  (ii) additional water whereby said feed comprises about 5 to about 95 weight percent water based on the total weight of said glycolic acid hydrogenation effluent and said additional water;

with a first extractant, comprising
(i) a hydrophobic solvent selected from alkanols having from 4 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
(ii) optionally, a hydrophilic solvent;
to form a first raffinate phase comprising a major amount of said one or more reaction by-products and a minor amount of said catalyst composition contained in said glycolic acid hydrogenation effluent and a first extract phase comprising a major amount of said catalyst composition and a minor amount of said one or more reaction by-products contained in said glycolic acid hydrogenation effluent;
(B) separating said first raffinate phase and said first extract phase; and
(C) recovering said catalyst composition from said first extract phase of step (B) by:
(i) extracting said first extract phase of step (B) with a second extractant comprising water, ethylene glycol, glycolate esters of ethylene glycol, glycolic acid, glycolic acid oligomers, or mixtures thereof to form a second extract phase comprising a major amount of said catalyst composition contained in said first extract phase of step (B) and a second raffinate phase comprising a minor amount of said catalyst composition contained in said first extract phase of step (B); or
(ii) distilling said first extract phase of step (B) to form a distillate comprising a major amount of said hydrophobic solvent contained in said first extract phase of step (B) and a bottoms comprising a major amount of said catalyst composition contained in said first extract phase of step (B).

21. The process according to claim 20 wherein said glycolic acid hydrogenation effluent comprises about 0.5 to about 30 weight percent ethylene glycol, about 0.5 to about 30 weight percent water, and about 40 to about 99 weight percent of said one or more reaction by-products.

22. The process according to claim 20 wherein said glycolic acid hydrogenation effluent comprises about 0.5 to about 20 weight percent ethylene glycol, about 0.5 to about 20 weight percent water, and about 70 to about 99 weight percent of said one or more reaction by-products.

23. The process according to claim 20 wherein said feed comprises about 10 to about 85 weight percent water based on the total weight of said glycolic acid hydrogenation effluent and said additional water.

24. The process according to claim 20 wherein said tridentate ligand comprises 1,1,1-tris(diphenylphosphinomethyl) methane, 1,1,1-tris(diphenylphosphinomethyl)ethane, (2-(butoxymethyl)-2-((diphenylphosphino)methyl)propane-1, 3-diyl)bis(diphenylphosphine), (2-(benzyloxymethyl)-2-((diphenylphosphino)methyl)propane-1,3-diyl)bis (diphenylphosphine), 1,1,1-tris(diphenylphosphinomethyl) propane, 1,1,1-tris(diphenylphosphinomethyl)butane, 1,1,1-tris(diphenylphosphinomethyl)-2,2-dimethylpropane, 1,1,1-tris(diphenylphosphinomethyl)cyclohexane, 1,1,1-tris (dicyclohexylphosphinomethyl)ethane, 1,1,1-tris (dimethylphosphinomethyl)ethane, 1,1,1-tris (diethylphosphinomethyl)ethane, or mixtures thereof.

25. The process according to claim 20 wherein said tridentate ligand comprises 1,1,1-tris(diphenylphosphinomethyl) ethane.

26. The process according to claim 20 wherein said hydrophobic solvent is selected from 2-ethylhexanol, butanol, pentanol, hexanol, heptanol, octanol, nonanol, decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof.

27. The process according to claim 20 wherein said hydrophobic solvent further comprises a hydrocarbon having from 5 to 20 carbon atoms.

28. The process according to claim 27 wherein said hydrocarbon is selected from hexane, heptane, octane, decane, benzene, toluene, xylenes, methyl napththalenes, isoparaffinic mixed hydrocarbons having a boiling range between 90 and 325° C., and mixtures thereof.

29. The process according to claim 20 wherein said first extractant comprises a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having from 2 to 6 carbon atoms, acetic acid, formic acid, α-hydroxy carboxylic acids having from 4 to 6 carbon atoms, glycolic acid oligomers having from 2 to 6 repeat units, polyol and diol esters of glycolic acid, and mixtures thereof.

30. The process according to claim 21 wherein said catalyst composition is recovered by extracting said first extract phase of step (B), and wherein said second extractant comprises mono- and diglycolate esters of ethylene glycol.

31. The process according to claim 20 wherein said tridentate ligand comprises 1,1,1-tris(diphenylphosphinomethyl) ethane and said hydrophobic solvent comprises pentanol and heptane, and wherein said catalyst composition is recovered by distilling said first extract phase of step (B).

32. The process according to claim 20 further comprising passing said second extract phase or said bottoms of step (C) to a process for the preparation of ethylene glycol by hydrogenation of glycolic acid, glycolate esters, glycolic acid oligomers, or mixtures thereof to ethylene glycol.

33. The process according to claim 20 further comprising combining said second raffinate phase of step (C) with said first extractant of step (A), distilling said second raffinate phase of step (C) to produce a hydrophobic solvent distillate and combining said hydrophobic solvent distillate with said first extractant of step (A), or combining said distillate of step (C) with said first extractant of step (A).

34. The process according to claim 20 wherein said catalyst composition is recovered by extracting said first extract phase of step (B), and wherein step (A) and/or step (C) are carried out by fractional countercurrent extraction.

35. A process for recovering a homogeneous catalyst, comprising
(A) extracting a feed comprising:
(i) a glycolic acid hydrogenation effluent, comprising
(a) about 0.5 to about 30 weight percent ethylene glycol, about 0.5 to about 30 weight percent water, and about 40 to about 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of said glycolic acid hydrogenation effluent; and
(b) a catalyst composition comprising ruthenium and 1,1,1-tris(diphenylphosphinomethyl)ethane; and (ii) additional water whereby said feed comprises about 10 to about 90 weight percent water based on the total weight of said glycolic acid hydrogenation effluent and said additional water;
with a first extractant, comprising about 60 to 100 weight percent 2-ethylhexanol, butanol, pentanol isobutyl isobutyrate, undecanone, methylisobutyl ketone, diisopropyl ether, or mixtures thereof, and 0 to about 40 weight percent of a hydrocarbon having from 5 to 20 carbon atoms, each based on the total weight of said first extractant, to form a first raffinate phase comprising a major amount of said one or more reaction by-products and a minor amount of said catalyst composition contained in said glycolic acid hydrogenation effluent and a first extract phase comprising a major amount of said catalyst composition and a minor amount of said one or more reaction by-products contained in said glycolic acid hydrogenation effluent;
(B) separating said first raffinate phase and said first extract phase;
(C) distilling said first extract phase of step (B) to form a distillate comprising a major amount of said hydrophobic solvent contained in said first extract phase of step (B) and a bottoms comprising a major amount of said catalyst composition contained in said first extract phase of step (B); and
(D) combining said distillate of step (C) with said first extractant of step (A).

36. The process according to claim 35 wherein said glycolic acid hydrogenation effluent comprises about 0.5 to about 20 weight percent ethylene glycol, about 0.5 to about 20 weight percent water, and about 70 to about 99 weight percent of said one or more reaction by-products, and wherein said feed comprises about 10 to about 85 weight percent water based on the total weight of said glycolic acid hydrogenation effluent and said additional water.

37. The process according to claim 35 wherein said hydrophobic solvent comprises pentanol and heptane, and further comprising passing said bottoms to a process for the preparation of ethylene glycol by hydrogenation of glycolic acid, glycolate esters, glycolic acid oligomers, or mixtures thereof to ethylene glycol.

38. A process for recovering a homogeneous catalyst, comprising
(A) contacting an aqueous mixture comprising glycolic acid, glycolate esters, methyl glycolate, oligomers of glycolic acid, or mixtures thereof, with hydrogen in the presence of a catalyst composition comprising ruthenium and 1,1,1-tris(diphenylphosphinomethyl)ethane to form a glycolic acid hydrogenation product, concentrating said glycolic acid hydrogenation product to form a glycolic acid hydrogenation effluent comprising about 0.5 to about 20 weight percent ethylene glycol, about 0.5 to about 20 weight percent water, and about 70 to about 99 weight percent of one or more reaction by-products selected from glycolic acid, glycolic acid oligomers, ethylene glycol oligomers, glycolate esters, 1,2-propanediol, 1,2-butanediol, and polyols, each based on the total weight of said glycolic acid hydrogenation effluent, and said catalyst composition;
(B) extracting a feed comprising said glycolic acid hydrogenation effluent and additional water whereby said feed comprises about 10 to about 85 weight percent water, based on the total weight of said glycolic acid hydrogenation effluent and said additional water, with a first extractant, comprising about 60 to 100 weight percent pentanol and about 0 to about 40 weight percent of a hydrocarbon having from 5 to 20 carbon atoms, each based on the total weight of said first extractant, to form a first raffinate phase comprising a major amount of said one or more reaction by-products contained in said glycolic acid hydrogenation effluent and a first extract phase comprising a major amount of said catalyst composition contained in said glycolic acid hydrogenation effluent;
(C) separating said first raffinate phase and said first extract phase;
(D) distilling said first extract phase of step (C) to form a distillate comprising a major amount of said hydrophobic solvent contained in said first extract phase of step (C) and a bottoms comprising a major amount of said catalyst composition contained in said first extract phase of step (C); and
(E) combining said bottoms of step (D) with said aqueous mixture of step (A).

\* \* \* \* \*